United States Patent
Neisz et al.

(10) Patent No.: US 9,681,975 B2
(45) Date of Patent: Jun. 20, 2017

(54) DEVICES AND METHODS FOR GASTROINTESTINAL BYPASS

(71) Applicant: ValenTx, Inc., Carpinteria, CA (US)

(72) Inventors: Johann Neisz, Minneapolis, MN (US); James Wright, Carpinteria, CA (US); Christopher Thierfelder, Santa Barbara, CA (US)

(73) Assignee: ValenTx, Inc., Maple Grove, MN (US)

( * ) Notice: Subject to any disclaimer, the term of this patent is extended or adjusted under 35 U.S.C. 154(b) by 62 days.

(21) Appl. No.: 13/896,838

(22) Filed: May 17, 2013

(65) Prior Publication Data

US 2013/0331759 A1     Dec. 12, 2013

Related U.S. Application Data

(63) Continuation-in-part of application No. 13/743,285, filed on Jan. 16, 2013, now abandoned, and a
(Continued)

(51) Int. Cl.
*A61M 5/00* (2006.01)
*A61F 5/00* (2006.01)
(Continued)

(52) U.S. Cl.
CPC .............. *A61F 5/0076* (2013.01); *A61F 2/04* (2013.01); *A61F 5/0036* (2013.01); *A61B 17/0401* (2013.01); *A61B 17/064* (2013.01); *A61B 17/068* (2013.01); *A61B 90/39* (2016.02); *A61B 2017/00818* (2013.01); *A61B 2017/0404* (2013.01); *A61B 2017/047* (2013.01);
(Continued)

(58) Field of Classification Search
CPC .............. A61B 17/1114; A61F 5/0076; A61F 2002/045; A61F 2002/044; A61F 5/0036
USPC ........................ 604/8, 9, 264; 623/23.64, 1.15
See application file for complete search history.

(56) References Cited

U.S. PATENT DOCUMENTS 3,357,432 A   12/1967  Sparks
3,589,356 A    6/1971  Silverman
(Continued)

FOREIGN PATENT DOCUMENTS

EP    0817598 B1   1/1998
EP    1237501 B1   9/2002
(Continued)

OTHER PUBLICATIONS

Figure 8 from KUO et al., Esophagus—anatomy and development, GI Motility online, 2006. http://www.nature.com/gimo/contents/pt1/full/gimo6.html#f8.
(Continued)

*Primary Examiner* — Leslie Deak
(74) *Attorney, Agent, or Firm* — Jinn Su

(57) ABSTRACT

Devices and methods for gastrointestinal bypass are described. A gastrointestinal bypass device includes a gastrointestinal cuff and a gastrointestinal sleeve. The cuff may be configured to be attached in the esophagus, and may be sufficiently flexible to expand and collapse to conform with the inside of the esophagus to allow the esophagus to function substantially normally. The sleeve is configured to be coupled to the cuff, and may be made of a material that is floppy or flaccid but does not substantially expand radially.

3 Claims, 75 Drawing Sheets

Related U.S. Application Data continuation-in-part of application No. 13/743,287, filed on Jan. 16, 2013, now Pat. No. 9,451,960, and a continuation-in-part of application No. 13/485,887, filed on May 31, 2012, now Pat. No. 8,956,318, and a continuation-in-part of application No. 13/485,889, filed on May 31, 2012, now Pat. No. 9,050,168, and a continuation-in-part of application No. 13/485,893, filed on May 31, 2012, now Pat. No. 9,039,649, and a continuation-in-part of application No. 13/485,896, filed on May 31, 2012, and a continuation-in-part of application No. 13/485,898, filed on May 31, 2012, now Pat. No. 9,173,759.

(51) Int. Cl.

| | | |
|---|---|---|
| *A61F 2/04* | (2013.01) | |
| *A61B 17/064* | (2006.01) | |
| *A61B 17/068* | (2006.01) | |
| *A61B 17/00* | (2006.01) | |
| *A61B 17/04* | (2006.01) | |
| *A61B 17/06* | (2006.01) | |
| *A61B 90/00* | (2016.01) | |

(52) U.S. Cl.
CPC ............ *A61B 2017/0409* (2013.01); *A61B 2017/0414* (2013.01); *A61B 2017/0417* (2013.01); *A61B 2017/0419* (2013.01); *A61B 2017/0464* (2013.01); *A61B 2017/0647* (2013.01); *A61B 2017/06052* (2013.01); *A61B 2090/395* (2016.02); *A61B 2090/3908* (2016.02); *A61B 2090/3966* (2016.02); *A61F 2002/045* (2013.01); *A61F 2250/0097* (2013.01)

(56) References Cited

U.S. PATENT DOCUMENTS

| | | | |
|---|---|---|---|
| 3,982,544 | A | 9/1976 | Dyck |
| 4,006,747 | A | 2/1977 | Kronenthal et al. |
| 4,043,345 | A | 8/1977 | Kramann et al. |
| 4,109,659 | A | 8/1978 | Sheridan |
| 4,133,315 | A | 1/1979 | Berman et al. |
| 4,134,405 | A | 1/1979 | Smit |
| 4,217,664 | A | 8/1980 | Faso |
| 4,235,238 | A | 11/1980 | Ogiu et al. |
| 4,252,131 | A | 2/1981 | Hon et al. |
| 4,271,839 | A | 6/1981 | Fogarty et al. |
| 4,315,509 | A | 2/1982 | Smit |
| 4,329,995 | A | 5/1982 | Anthracite |
| 4,416,267 | A | 11/1983 | Garren et al. |
| 4,493,711 | A | 1/1985 | Chin et al. |
| 4,501,264 | A | 2/1985 | Rockey |
| 4,532,926 | A | 8/1985 | O'Holla |
| 4,606,347 | A | 8/1986 | Fogarty et al. |
| 4,613,323 | A | 9/1986 | Norton et al. |
| 4,630,609 | A | 12/1986 | Chin |
| 4,641,653 | A | 2/1987 | Rockey |
| 4,719,916 | A | 1/1988 | Ravo |
| 4,763,653 | A | 8/1988 | Rockey |
| 4,826,481 | A | 5/1989 | Sacks et al. |
| 4,846,836 | A | 7/1989 | Reich |
| 4,863,440 | A | 9/1989 | Chin |
| 4,905,693 | A | 3/1990 | Ravo |
| 4,946,440 | A | 8/1990 | Hall |
| 5,085,661 | A | 2/1992 | Moss |
| 5,104,399 | A | 4/1992 | Lazarus |
| RE34,021 | E | 8/1992 | Mueller et al. |
| 5,171,305 | A | 12/1992 | Schickling et al. |
| 5,236,423 | A | 8/1993 | Mix et al. |
| 5,269,809 | A | 12/1993 | Hayhurst et al. |
| 5,306,300 | A | 4/1994 | Berry |
| 5,314,473 | A | 5/1994 | Godin |
| 5,318,530 | A | 6/1994 | Nelson, Jr. |
| 5,411,508 | A | 5/1995 | Bessler et al. |
| 5,425,765 | A | 6/1995 | Tiefenbrun et al. |
| 5,431,666 | A | 7/1995 | Sauer et al. |
| 5,443,499 | A | 8/1995 | Schmitt |
| 5,458,573 | A | 10/1995 | Summers |
| 5,470,337 | A | 11/1995 | Moss |
| 5,503,634 | A | 4/1996 | Christy |
| 5,582,616 | A | 12/1996 | Bolduc et al. |
| 5,613,975 | A | 3/1997 | Christy |
| 5,645,568 | A | 7/1997 | Chervitz et al. |
| 5,676,688 | A | 10/1997 | Jaker et al. |
| 5,681,324 | A | 10/1997 | Kammerer et al. |
| 5,695,517 | A | 12/1997 | Marin et al. |
| 5,785,684 | A | 7/1998 | Zimmon |
| 5,807,303 | A | 9/1998 | Bays |
| 5,820,584 | A | 10/1998 | Crabb |
| 5,824,008 | A | 10/1998 | Bolduc et al. |
| 5,824,036 | A | 10/1998 | Lauterjung |
| 5,843,164 | A | 12/1998 | Frantzen et al. |
| 5,861,036 | A | 1/1999 | Godin |
| 5,887,594 | A | 3/1999 | LoCicero, III |
| 5,957,940 | A | 9/1999 | Tanner et al. |
| 5,972,023 | A | 10/1999 | Tanner et al. |
| 5,997,556 | A | 12/1999 | Tanner |
| 6,007,544 | A | 12/1999 | Kim |
| 6,066,146 | A | 5/2000 | Carroll et al. |
| 6,113,609 | A | 9/2000 | Adams |
| 6,159,158 | A | 12/2000 | Lowe |
| 6,193,733 | B1 | 2/2001 | Adams |
| 6,206,895 | B1 | 3/2001 | Levinson |
| 6,250,922 | B1 | 6/2001 | Bassett et al. |
| 6,254,642 | B1 | 7/2001 | Taylor |
| 6,264,700 | B1 | 7/2001 | Kilcoyne et al. |
| 6,285,897 | B1 | 9/2001 | Kilcoyne et al. |
| 6,302,917 | B1 | 10/2001 | Dua et al. |
| 6,309,343 | B1 | 10/2001 | Lentz et al. |
| 6,312,437 | B1 | 11/2001 | Kortenbach |
| 6,338,345 | B1 | 1/2002 | Johnson et al. |
| 6,387,104 | B1 | 5/2002 | Pugsley, Jr. et al. |
| 6,402,780 | B2 | 6/2002 | Williamson, IV et al. |
| 6,409,656 | B1 | 6/2002 | Sangouard et al. |
| 6,432,064 | B1 | 8/2002 | Hibner et al. |
| 6,447,533 | B1 | 9/2002 | Adams |
| 6,464,707 | B1 | 10/2002 | Bjerken |
| 6,494,888 | B1 | 12/2002 | Laufer et al. |
| 6,520,974 | B2 | 2/2003 | Tanner et al. |
| 6,535,764 | B2 | 3/2003 | Imran et al. |
| 6,544,291 | B2 | 4/2003 | Taylor |
| 6,558,400 | B2 | 5/2003 | Deem et al. |
| 6,558,429 | B2 | 5/2003 | Taylor |
| 6,592,596 | B1 | 7/2003 | Geitz |
| 6,595,911 | B2 | 7/2003 | LoVuolo |
| 6,626,916 | B1 | 9/2003 | Yeung et al. |
| 6,626,919 | B1 | 9/2003 | Swanstrom |
| 6,635,066 | B2 | 10/2003 | Tanner et al. |
| 6,675,809 | B2 | 1/2004 | Stack et al. |
| 6,692,506 | B1 | 2/2004 | Ory et al. |
| 6,699,263 | B2 | 3/2004 | Cope |
| 6,702,735 | B2 | 3/2004 | Kelly |
| 6,736,828 | B1 | 5/2004 | Adams et al. |
| 6,740,121 | B2 | 5/2004 | Geitz |
| 6,746,489 | B2 | 6/2004 | Dua et al. |
| 6,764,518 | B2 | 7/2004 | Godin |
| 6,773,452 | B2 | 8/2004 | Shaker |
| 6,790,237 | B2 | 9/2004 | Stinson |
| 6,845,776 | B2 | 1/2005 | Stack et al. |
| 6,946,002 | B2 | 9/2005 | Geitz |
| 6,994,095 | B2 | 2/2006 | Burnett |
| 7,025,791 | B2 | 4/2006 | Levine et al. |
| 7,037,344 | B2 | 5/2006 | Kagan et al. |
| 7,083,629 | B2 | 8/2006 | Weller et al. |
| 7,097,665 | B2 | 8/2006 | Stack et al. |
| 7,111,627 | B2 | 9/2006 | Stack et al. |
| 7,120,498 | B2 | 10/2006 | Imran et al. |
| 7,121,283 | B2 | 10/2006 | Stack et al. |
| 7,122,058 | B2 | 10/2006 | Levine et al. |
| 7,146,984 | B2 | 12/2006 | Stack et al. |

(56) References Cited

U.S. PATENT DOCUMENTS

| | | |
|---|---|---|
| 7,152,607 B2 | 12/2006 | Stack et al. |
| 7,160,312 B2 | 1/2007 | Saadat |
| 7,175,669 B2 | 2/2007 | Geitz |
| RE39,533 E | 3/2007 | Ranoux |
| 7,211,114 B2 | 5/2007 | Bessler et al. |
| 7,220,237 B2 | 5/2007 | Gannoe et al. |
| 7,220,284 B2 | 5/2007 | Kagan et al. |
| 7,229,428 B2 | 6/2007 | Gannoe et al. |
| 7,244,270 B2 | 7/2007 | Lesh |
| 7,267,694 B2 | 9/2007 | Levine et al. |
| 7,288,099 B2 | 10/2007 | Deem et al. |
| 7,288,101 B2 | 10/2007 | Deem et al. |
| 7,306,614 B2 | 12/2007 | Weller et al. |
| 7,309,341 B2 | 12/2007 | Ortiz et al. |
| 7,314,489 B2 | 1/2008 | McKenna et al. |
| 7,316,716 B2 | 1/2008 | Egan |
| 7,329,285 B2 | 2/2008 | Levine et al. |
| 7,338,505 B2 | 3/2008 | Belson |
| 7,347,868 B2 | 3/2008 | Burnett et al. |
| 7,347,875 B2 | 3/2008 | Levine et al. |
| 7,354,454 B2 | 4/2008 | Stack et al. |
| 7,361,180 B2 | 4/2008 | Saadat et al. |
| 7,371,215 B2 | 5/2008 | Colliou et al. |
| 7,390,329 B2 | 6/2008 | Westra et al. |
| 7,416,554 B2 | 8/2008 | Lam et al. |
| 7,431,725 B2 | 10/2008 | Stack et al. |
| 7,468,060 B2 | 12/2008 | Utley et al. |
| 7,476,256 B2 | 1/2009 | Meade et al. |
| 7,483,754 B2 | 1/2009 | Imran et al. |
| 7,509,175 B2 | 3/2009 | Sparks et al. |
| 7,520,884 B2 | 4/2009 | Swanstrom et al. |
| 7,571,729 B2 | 8/2009 | Saadat et al. |
| 7,615,064 B2 | 11/2009 | Bjerken |
| 7,628,821 B2 | 12/2009 | Stack et al. |
| 7,666,180 B2 | 2/2010 | Holsten et al. |
| 7,678,068 B2 | 3/2010 | Levine et al. |
| 7,678,135 B2 | 3/2010 | Maahs et al. |
| 7,682,330 B2 | 3/2010 | Meade et al. |
| 7,703,459 B2 | 4/2010 | Saadat et al. |
| 7,704,261 B2 | 4/2010 | Sakamoto et al. |
| 7,704,264 B2 | 4/2010 | Ewers et al. |
| 7,708,684 B2 | 5/2010 | Demarais et al. |
| 7,736,374 B2 | 6/2010 | Vaughan et al. |
| 7,736,378 B2 | 6/2010 | Maahs et al. |
| 7,753,870 B2 | 7/2010 | Demarais et al. |
| 7,766,973 B2 | 8/2010 | Levine et al. |
| 7,780,592 B2 | 8/2010 | Tronnes |
| 7,794,447 B2 | 9/2010 | Dann et al. |
| 7,815,589 B2 | 10/2010 | Meade et al. |
| 7,833,280 B2 | 11/2010 | Stack et al. |
| 7,837,669 B2 | 11/2010 | Dann et al. |
| 7,841,978 B2 | 11/2010 | Gertner |
| 7,846,138 B2 | 12/2010 | Dann et al. |
| 7,881,797 B2 | 2/2011 | Griffin et al. |
| 7,892,214 B2 | 2/2011 | Kagan et al. |
| 7,935,073 B2 | 5/2011 | Levine et al. |
| 7,942,884 B2 | 5/2011 | Vahid et al. |
| 7,981,162 B2 | 7/2011 | Stack et al. |
| 8,012,135 B2 | 9/2011 | Dann et al. |
| 8,012,140 B1 | 9/2011 | Kagan et al. |
| 8,020,741 B2 | 9/2011 | Cole et al. |
| 8,029,455 B2 | 10/2011 | Stack et al. |
| 8,034,063 B2 | 10/2011 | Binmoeller |
| 8,070,743 B2 | 12/2011 | Kagan et al. |
| 8,083,758 B2 | 12/2011 | Hsu et al. |
| 8,096,966 B2 | 1/2012 | Levine et al. |
| 8,100,925 B2 | 1/2012 | Hsu et al. |
| 8,105,342 B2 | 1/2012 | Onuki et al. |
| 8,118,767 B2 | 2/2012 | Laufer |
| 8,118,774 B2 | 2/2012 | Dann et al. |
| 8,147,441 B2 | 4/2012 | Gannoe et al. |
| 8,182,441 B2 | 5/2012 | Swain et al. |
| 8,182,459 B2 | 5/2012 | Dann et al. |
| 8,206,417 B2 | 6/2012 | Maahs et al. |
| 8,206,456 B2 | 6/2012 | Stack et al. |
| 8,211,186 B2 | 7/2012 | Belhe et al. |
| 8,257,374 B2 | 9/2012 | Hsu et al. |
| 8,282,598 B2 | 10/2012 | Belhe et al. |
| 8,298,291 B2 | 10/2012 | Ewers et al. |
| 8,303,669 B2 | 11/2012 | Meade et al. |
| 8,372,158 B2 | 2/2013 | Levy et al. |
| 8,376,981 B2 | 2/2013 | Laufer |
| 8,382,800 B2 | 2/2013 | Maahs et al. |
| 8,425,451 B2 | 4/2013 | Levine et al. |
| 8,444,657 B2 | 5/2013 | Saadat et al. |
| 8,702,641 B2 | 4/2014 | Belhe et al. |
| 8,808,270 B2 | 8/2014 | Dann et al. |
| 8,956,318 B2 | 2/2015 | Miller et al. |
| 8,968,270 B2 | 3/2015 | Kagan et al. |
| 9,039,649 B2 | 5/2015 | Neisz et al. |
| 9,050,168 B2 | 6/2015 | Neisz et al. |
| 9,060,844 B2 | 6/2015 | Kagan et al. |
| 9,173,759 B2 | 11/2015 | Nelson et al. |
| 9,265,596 B2 | 2/2016 | Shank et al. |
| 2001/0016748 A1 | 8/2001 | Tanner et al. |
| 2001/0020189 A1 | 9/2001 | Taylor |
| 2001/0020190 A1 | 9/2001 | Taylor |
| 2001/0044595 A1 | 11/2001 | Reydel et al. |
| 2001/0056282 A1 | 12/2001 | Sonnenschein et al. |
| 2002/0016607 A1 | 2/2002 | Bonadio et al. |
| 2002/0026214 A1 | 2/2002 | Tanner et al. |
| 2002/0035370 A1 | 3/2002 | Kortenbach |
| 2002/0040226 A1 | 4/2002 | Laufer et al. |
| 2002/0058960 A1 | 5/2002 | Hudson et al. |
| 2002/0082621 A1 | 6/2002 | Schurr et al. |
| 2002/0111658 A1 | 8/2002 | Greenberg et al. |
| 2002/0143387 A1 | 10/2002 | Soetikno et al. |
| 2002/0165589 A1 | 11/2002 | Imran et al. |
| 2002/0183768 A1 | 12/2002 | Deem et al. |
| 2002/0188344 A1 | 12/2002 | Bolea et al. |
| 2002/0188354 A1 | 12/2002 | Peghini |
| 2002/0198588 A1 | 12/2002 | Armstrong et al. |
| 2003/0014064 A1 | 1/2003 | Blatter |
| 2003/0018358 A1 | 1/2003 | Saadat |
| 2003/0040804 A1 | 2/2003 | Stack et al. |
| 2003/0040808 A1 | 2/2003 | Stack et al. |
| 2003/0055313 A1 | 3/2003 | Anderson et al. |
| 2003/0055442 A1 | 3/2003 | Laufer et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120285 A1 | 6/2003 | Kortenbach |
| 2003/0120292 A1 | 6/2003 | Park et al. |
| 2003/0130560 A1 | 7/2003 | Suzuki et al. |
| 2003/0130561 A1 | 7/2003 | Suzuki et al. |
| 2003/0139752 A1 | 7/2003 | Pasricha et al. |
| 2003/0171775 A1 | 9/2003 | Belson |
| 2003/0176912 A1 | 9/2003 | Chuter et al. |
| 2003/0181929 A1 | 9/2003 | Geitz |
| 2003/0191497 A1 | 10/2003 | Cope |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2004/0002734 A1 | 1/2004 | Fallin et al. |
| 2004/0006351 A1 | 1/2004 | Gannoe et al. |
| 2004/0024427 A1 | 2/2004 | Imran et al. |
| 2004/0039250 A1 | 2/2004 | Tholfsen et al. |
| 2004/0039452 A1 | 2/2004 | Bessler |
| 2004/0044364 A1 | 3/2004 | DeVries et al. |
| 2004/0059349 A1 | 3/2004 | Sixto, Jr. et al. |
| 2004/0059354 A1 | 3/2004 | Smith et al. |
| 2004/0082963 A1 | 4/2004 | Gannoe et al. |
| 2004/0087976 A1 | 5/2004 | DeVries et al. |
| 2004/0087977 A1 | 5/2004 | Nolan et al. |
| 2004/0088023 A1 | 5/2004 | Imran et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0097986 A1 | 5/2004 | Adams |
| 2004/0097987 A1 | 5/2004 | Pugsley et al. |

(56) References Cited

U.S. PATENT DOCUMENTS

| | | |
|---|---|---|
| 2004/0102855 A1 | 5/2004 | Shank |
| 2004/0107004 A1 | 6/2004 | Levine et al. |
| 2004/0116949 A1 | 6/2004 | Ewers et al. |
| 2004/0117031 A1 | 6/2004 | Stack et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0133089 A1 | 7/2004 | Kilcoyne et al. |
| 2004/0133147 A1 | 7/2004 | Woo |
| 2004/0133219 A1 | 7/2004 | Forsell |
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0138761 A1 | 7/2004 | Stack et al. |
| 2004/0143342 A1 | 7/2004 | Stack et al. |
| 2004/0147958 A1 | 7/2004 | Lam et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0172142 A1 | 9/2004 | Stack et al. |
| 2004/0176799 A1 | 9/2004 | Chanduszko et al. |
| 2004/0181242 A1 | 9/2004 | Stack et al. |
| 2004/0186514 A1 | 9/2004 | Swain et al. |
| 2004/0193190 A1 | 9/2004 | Liddicoat et al. |
| 2004/0199189 A1 | 10/2004 | Gifford, III et al. |
| 2004/0204768 A1 | 10/2004 | Geitz |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243195 A1 | 12/2004 | Imran et al. |
| 2004/0249362 A1 | 12/2004 | Levine et al. |
| 2004/0249367 A1 | 12/2004 | Saadat et al. |
| 2005/0033240 A1 | 2/2005 | Oishi et al. |
| 2005/0033330 A1 | 2/2005 | Vargas et al. |
| 2005/0033331 A1 | 2/2005 | Burnett et al. |
| 2005/0033332 A1 | 2/2005 | Burnett |
| 2005/0043749 A1 | 2/2005 | Breton et al. |
| 2005/0043757 A1 | 2/2005 | Arad et al. |
| 2005/0049718 A1* | 3/2005 | Dann .............. A61F 2/04 623/23.65 |
| 2005/0055039 A1 | 3/2005 | Burnett et al. |
| 2005/0065401 A1 | 3/2005 | Saadat et al. |
| 2005/0075653 A1 | 4/2005 | Saadat et al. |
| 2005/0075654 A1 | 4/2005 | Kelleher |
| 2005/0080431 A1 | 4/2005 | Levine et al. |
| 2005/0080444 A1 | 4/2005 | Kraemer et al. |
| 2005/0085787 A1 | 4/2005 | Laufer |
| 2005/0085900 A1 | 4/2005 | Case et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0101977 A1 | 5/2005 | Gannoe et al. |
| 2005/0125020 A1 | 6/2005 | Meade et al. |
| 2005/0125075 A1 | 6/2005 | Meade et al. |
| 2005/0143784 A1 | 6/2005 | Imran |
| 2005/0177181 A1 | 8/2005 | Kagan et al. |
| 2005/0187567 A1 | 8/2005 | Baker et al. |
| 2005/0192629 A1 | 9/2005 | Saadat et al. |
| 2005/0197714 A1 | 9/2005 | Sayet |
| 2005/0197715 A1 | 9/2005 | Kugler et al. |
| 2005/0203547 A1 | 9/2005 | Weller et al. |
| 2005/0222592 A1 | 10/2005 | Gannoe et al. |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0245948 A1 | 11/2005 | Khalaj |
| 2005/0247320 A1 | 11/2005 | Stack et al. |
| 2005/0250984 A1 | 11/2005 | Lam et al. |
| 2005/0251159 A1 | 11/2005 | Ewers et al. |
| 2005/0251176 A1 | 11/2005 | Swanstrom et al. |
| 2005/0251208 A1 | 11/2005 | Elmer et al. |
| 2005/0251209 A1 | 11/2005 | Saadat et al. |
| 2005/0256587 A1 | 11/2005 | Egan |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2005/0267595 A1 | 12/2005 | Chen et al. |
| 2006/0009858 A1 | 1/2006 | Levine et al. |
| 2006/0015125 A1 | 1/2006 | Swain |
| 2006/0020164 A1 | 1/2006 | Butler et al. |
| 2006/0020247 A1 | 1/2006 | Kagan et al. |
| 2006/0020254 A1 | 1/2006 | Hoffmann |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0135971 A1 | 6/2006 | Swanstrom et al. |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0173422 A1 | 8/2006 | Reydel et al. |
| 2006/0206063 A1 | 9/2006 | Kagan et al. |
| 2006/0206064 A1 | 9/2006 | Kagan et al. |
| 2006/0212052 A1 | 9/2006 | Shin et al. |
| 2006/0217762 A1 | 9/2006 | Maahs et al. |
| 2006/0235446 A1 | 10/2006 | Godin |
| 2006/0247718 A1 | 11/2006 | Starkebaum |
| 2006/0253126 A1 | 11/2006 | Bjerken et al. |
| 2006/0264982 A1 | 11/2006 | Viola et al. |
| 2006/0265021 A1 | 11/2006 | Herbert et al. |
| 2006/0265042 A1 | 11/2006 | Catanese, III et al. |
| 2006/0265082 A1 | 11/2006 | Meade et al. |
| 2006/0287734 A1 | 12/2006 | Stack et al. |
| 2006/0293742 A1 | 12/2006 | Dann et al. |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1* | 1/2007 | Dann et al. .......... 623/1.11 |
| 2007/0016244 A1 | 1/2007 | Behl et al. |
| 2007/0027548 A1 | 2/2007 | Levine et al. |
| 2007/0027549 A1 | 2/2007 | Godin |
| 2007/0032821 A1 | 2/2007 | Chin-Chen et al. |
| 2007/0032879 A1 | 2/2007 | Levine et al. |
| 2007/0083271 A1 | 4/2007 | Levine et al. |
| 2007/0100367 A1 | 5/2007 | Quijano et al. |
| 2007/0100368 A1 | 5/2007 | Quijano et al. |
| 2007/0106233 A1 | 5/2007 | Huang et al. |
| 2007/0106313 A1 | 5/2007 | Golden et al. |
| 2007/0129719 A1 | 6/2007 | Kendale et al. |
| 2007/0149994 A1 | 6/2007 | Sosnowski et al. |
| 2007/0156248 A1 | 7/2007 | Marco et al. |
| 2007/0178160 A1 | 8/2007 | Burnett |
| 2007/0198074 A1 | 8/2007 | Dann et al. |
| 2007/0208360 A1 | 9/2007 | Demarais et al. |
| 2007/0219571 A1 | 9/2007 | Balbierz et al. |
| 2007/0225555 A1 | 9/2007 | Stefanchik |
| 2007/0233162 A1 | 10/2007 | Gannoe et al. |
| 2007/0250132 A1 | 10/2007 | Burnett |
| 2007/0293716 A1 | 12/2007 | Baker et al. |
| 2007/0293885 A1 | 12/2007 | Binmoeller |
| 2008/0004606 A1 | 1/2008 | Swain et al. |
| 2008/0009888 A1 | 1/2008 | Ewers et al. |
| 2008/0033574 A1 | 2/2008 | Bessler et al. |
| 2008/0058840 A1 | 3/2008 | Albrecht et al. |
| 2008/0058887 A1 | 3/2008 | Griffin et al. |
| 2008/0082167 A1 | 4/2008 | Edidin et al. |
| 2008/0103604 A1 | 5/2008 | Levine et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |

(56) References Cited

U.S. PATENT DOCUMENTS

| | | |
|---|---|---|
| 2008/0208357 A1 | 8/2008 | Melanson et al. |
| 2008/0221597 A1 | 9/2008 | Wallace et al. |
| 2008/0228030 A1 | 9/2008 | Godin |
| 2008/0243071 A1 | 10/2008 | Quijano et al. |
| 2008/0249533 A1* | 10/2008 | Godin ................. A61F 2/04 606/108 |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0269797 A1 | 10/2008 | Stack et al. |
| 2008/0294179 A1 | 11/2008 | Balbierz et al. |
| 2009/0012356 A1 | 1/2009 | Dann et al. |
| 2009/0012541 A1 | 1/2009 | Dahl et al. |
| 2009/0012544 A1 | 1/2009 | Thompson et al. |
| 2009/0012553 A1 | 1/2009 | Swain et al. |
| 2009/0018603 A1 | 1/2009 | Mitelberg et al. |
| 2009/0024143 A1 | 1/2009 | Crews et al. |
| 2009/0062881 A1 | 3/2009 | Gross et al. |
| 2009/0125040 A1 | 5/2009 | Hambly et al. |
| 2009/0149871 A9 | 6/2009 | Kagan et al. |
| 2009/0177215 A1 | 7/2009 | Stack et al. |
| 2009/0182355 A1 | 7/2009 | Levine et al. |
| 2009/0182413 A1 | 7/2009 | Burkart et al. |
| 2009/0216337 A1 | 8/2009 | Egan et al. |
| 2010/0016988 A1 | 1/2010 | Stack et al. |
| 2010/0023130 A1 | 1/2010 | Henry et al. |
| 2010/0030017 A1 | 2/2010 | Baker et al. |
| 2010/0049224 A1 | 2/2010 | Vargas |
| 2010/0121462 A1 | 5/2010 | Sobrino-Serrano et al. |
| 2010/0217151 A1 | 8/2010 | Gostout et al. |
| 2010/0256775 A1 | 10/2010 | Belhe et al. |
| 2010/0276469 A1 | 11/2010 | Crews et al. |
| 2010/0280529 A1 | 11/2010 | Crews et al. |
| 2010/0331623 A1 | 12/2010 | Sauer et al. |
| 2011/0004229 A1 | 1/2011 | Priplata et al. |
| 2011/0082471 A1 | 4/2011 | Holcomb et al. |
| 2011/0098630 A1 | 4/2011 | Gagner et al. |
| 2011/0106273 A1 | 5/2011 | Belhe et al. |
| 2011/0125211 A1 | 5/2011 | Griffin et al. |
| 2011/0172584 A1 | 7/2011 | Chin |
| 2011/0213469 A1 | 9/2011 | Chin et al. |
| 2011/0245752 A1 | 10/2011 | Levine et al. |
| 2011/0245854 A1 | 10/2011 | Buxbaum et al. |
| 2011/0275912 A1 | 11/2011 | Boyden et al. |
| 2011/0276091 A1 | 11/2011 | Melanson et al. |
| 2011/0319980 A1 | 12/2011 | Ryan |
| 2012/0029413 A1 | 2/2012 | Meade et al. |
| 2012/0029535 A1 | 2/2012 | Swain |
| 2012/0029611 A1 | 2/2012 | Weidman et al. |
| 2012/0053504 A1 | 3/2012 | Kagan et al. |
| 2012/0065571 A1 | 3/2012 | Thompson et al. |
| 2012/0095384 A1 | 4/2012 | Babkes et al. |
| 2012/0184893 A1 | 7/2012 | Thompson et al. |
| 2012/0209164 A1 | 8/2012 | Kagan et al. |
| 2012/0215235 A1 | 8/2012 | Fogel |
| 2012/0232459 A1 | 9/2012 | Dann et al. |
| 2012/0245504 A1 | 9/2012 | Tzvetanov et al. |
| 2012/0253324 A1 | 10/2012 | Lee et al. |
| 2012/0259317 A1 | 10/2012 | Baldwin et al. |
| 2012/0296254 A1 | 11/2012 | Swain et al. |
| 2013/0030351 A1 | 1/2013 | Belhe et al. |
| 2013/0079603 A1 | 3/2013 | Vargas |
| 2013/0184723 A1 | 7/2013 | Swope et al. |
| 2013/0184808 A1 | 7/2013 | Hall et al. |
| 2013/0261368 A1 | 10/2013 | Schwartz |
| 2013/0324902 A1 | 12/2013 | Miller et al. |
| 2013/0324905 A1 | 12/2013 | Nelson et al. |
| 2013/0324926 A1 | 12/2013 | Nelson et al. |
| 2013/0331759 A1 | 12/2013 | Neisz et al. |
| 2014/0180192 A1 | 6/2014 | Ortiz et al. |
| 2014/0188245 A1 | 7/2014 | Neisz et al. |
| 2014/0358065 A1 | 12/2014 | Dann et al. |
| 2015/0238340 A1 | 8/2015 | Kagan et al. |
| 2015/0366693 A1 | 12/2015 | Kagan et al. |

FOREIGN PATENT DOCUMENTS

| | | |
|---|---|---|
| WO | WO 8000007 A1 | 1/1980 |
| WO | WO 9101117 A1 | 2/1991 |
| WO | WO 9629954 A1 | 10/1996 |
| WO | WO 9856440 A1 | 12/1998 |
| WO | WO 9921490 A1 | 5/1999 |
| WO | WO 9960931 A1 | 12/1999 |
| WO | WO 0012027 A1 | 3/2000 |
| WO | WO 0135834 A1 | 5/2001 |
| WO | WO 0143663 A1 | 6/2001 |
| WO | WO 0183017 A1 | 11/2001 |
| WO | WO 0185034 A1 | 11/2001 |
| WO | WO 02094132 A2 | 11/2002 |
| WO | WO 02102227 A2 | 12/2002 |
| WO | WO 03017882 A2 | 3/2003 |
| WO | WO 03086246 A1 | 10/2003 |
| WO | WO 03086247 A1 | 10/2003 |
| WO | WO 03094785 A1 | 11/2003 |
| WO | WO 2004017863 A2 | 3/2004 |
| WO | WO 2004021894 A1 | 3/2004 |
| WO | WO 2004041119 A2 | 5/2004 |
| WO | WO 2004041133 A1 | 5/2004 |
| WO | WO 2004047686 A1 | 6/2004 |
| WO | WO 2004049982 A2 | 6/2004 |
| WO | WO 2004064680 A1 | 8/2004 |
| WO | WO 2004064685 A1 | 8/2004 |
| WO | WO 2004080336 A2 | 9/2004 |
| WO | WO 2004086984 A1 | 10/2004 |
| WO | WO 2004087014 A2 | 10/2004 |
| WO | WO 2004087233 A2 | 10/2004 |
| WO | WO 2004103214 A1 | 12/2004 |
| WO | WO 2004103430 A2 | 12/2004 |
| WO | WO 2004105643 A1 | 12/2004 |
| WO | WO 2005011463 A2 | 2/2005 |
| WO | WO 2005011519 A2 | 2/2005 |
| WO | WO 2005032422 A1 | 4/2005 |
| WO | WO 2005037152 A1 | 4/2005 |
| WO | WO 2005060869 A1 | 7/2005 |
| WO | WO 2005060882 A1 | 7/2005 |
| WO | WO 2005110280 A2 | 11/2005 |
| WO | WO 2006044640 A1 | 4/2006 |
| WO | WO 2006055847 A2 | 5/2006 |
| WO | WO 2006130836 A2 | 12/2006 |
| WO | WO 2007056583 A1 | 5/2007 |
| WO | WO 2008121409 A1 | 10/2008 |
| WO | WO 2009011881 A1 | 1/2009 |
| WO | WO 2011031981 A1 | 3/2011 |

OTHER PUBLICATIONS

Mittal et al., Sphincter mechanisms at the lower end of the esophagus, GI Motility online, 2006. http://www.nature.com/gimo/contents/pt1/full/gimo14.html.

U.S. Appl. No. 14/987,398, filed Jan. 4, 2016, Thompson et al.

Awan et al., Endoscopic vertical band gastroplasty with an endoscopic sewing machine, Gastrointestinal Endoscopy, vol. 55, No. 2, pp. 254-256, Feb. 2002.

Berger et al., Progression rate of self-propelled feeding tubes in critically ill patients, Intensive Care Medicine, vol. 28, No. 12, pp. 1768-1774, Dec. 2002.

Boston Scientific Corp., Website, Microvasive Wallstent® Colonic & Duodenal Endoprosthesis, Sep. 2002.

C.R. Bard, Inc., Website, The Bard EndoCinch Procedure, 2002.

Chuttani, Endoscopic full-thickness plication: the device, technique, pre-clinical and early clinical experience, Gastrointestinal Endoscopy Clinics of North America, vol. 13, No. 1, pp. 109-116, Jan. 2003.

Cook Inc., Brochure, Cope Gastrointestinal Suture Anchor Set, 2000.

Cook Inc., Website, Geenen® Pancreatic Stent Sets, Sep. 2002.

Crampton et al., Silastic Ring Gastric Bypass: Results in 64 Patients, Obesity Surgery, vol. 7, No. 6, pp. 489-494, Dec. 1997.

De La Fuente et al., Evaluation of porcine-derived small intestine submucosa as a biodegradable graft for gastrointestinal healing, Journal of Gastrointestinal Surgery (abstract), vol. 7, No. 1, pp. 96-101, Jan. 2003.

(56) References Cited

OTHER PUBLICATIONS

Demeester, Microvasive gastric stapler: the device, technique, and preclinical results, Gastrointestinal Endoscopy Clinics of North America, vol. 13, No. 1, pp. 117-133, Jan. 2003.
Espinet-Coll et al., Current endoscopic techniques in the treatment of obesity, Revista Española de Enfermedades Digestivas, vol. 104, No. 2, pp. 72-87, Feb. 2012.
Felsher et al., A Novel Endolaparoscopic Intragastric Partitioning for Treatment of Morbid Obesity, Surgical Laparoscopy, Endoscopy & Percutaneous Techniques, vol. 14, No. 5, pp. 243-246, Oct. 2004.
Fennerty, Endoscopic suturing for treatment of GERD, Gastrointestinal Endoscopy, vol. 57, No. 3, pp. 390-395, Mar. 2003.
Fobi et al., Gastric Bypass Operation for Obesity, World Journal of Surgery, vol. 22, No. 9, pp. 925-935, Sep. 1998.
Fritscher-Ravens et al., A through-the-scope device for suturing and tissue approximation under EUS control, Gastrointestinal Endoscopy, vol. 56, No. 5, pp. 737-742, Nov. 2002.
Fritscher-Ravens et al., Abstract, Endoscopic Gastropexy and Crural Repair for Gastro-Esophageal Reflux: Transgastric Surgery Under Endoscopic Ultrasound Control II, Gastroenterology, vol. 124, No. 4, supp. 1, p. A38, Apr. 2003.
Fritscher-Ravens et al., Transgastric gastropexy and hiatal hernia repair for GERD under EUS control: a porcine model, Gastrointestinal Endoscopy, vol. 59, No. 1, pp. 89-95, Jan. 2004.
Gleason, Bioabsorbable Polymers, 1998.
Godin et al., Abstract, Endoscopic suturing of a novel gastroesophageal antireflux device (GARD) a preliminary report, Gastrointestinal Endoscopy, vol. 43, No. 4, p. 336, Apr. 1996.
Kadirkamanathan et al., Antireflux operations at flexible endoscopy using endoluminal stitching techniques: an experimental study, Gastrointestinal Endoscopy, vol. 44, No. 2, pp. 133-143, Aug. 1996.
Keyser et al., Double Closed Loop Obstruction and Perforation in a Previous Roux-en-Y Gastric Bypass, Obesity Surgery, vol. 8, No. 4, pp. 475-479, Aug. 1998.
Long et al., Abstract, Techniques for advancing guide wires and devices in the lumen of the gastrointestinal tract, Gastrointestinal Endoscopy, vol. 57, No. 5, p. AB177, Apr. 2003.
Merlini et al., [Development of a gastroplasty with variable diameter. Experimental study using artificial sphincters] (abstract), Helvetica Chirurgica Acta., vol. 58, No. 6, pp. 789-793, May 1992.
Middleton et al., Synthetic Biodegradable Polymers as Medical Devices, Medical Plastics and Biomaterials Magazine, Mar. 1998.
Nakamura et al., Experimental study on in situ tissue engineering of the stomach by an acellular collage sponge scaffold graft (abstract), ASAIO Journal, vol. 47, No. 3, pp. 206-210, May-Jun. 2001.
Oh et al., Weight Loss Following Transected Gastric Bypass with Proximal Roux-en-Y, Obesity Surgery, vol. 7, No. 2, pp. 142-147, Apr. 1997.
Oh et al., Repair of Full-Thickness Defects in Alimentary Tract Wall With Patches of Expanded Polytetrafluoroethylene, Annals of Surgery, vol. 235, No. 5, pp. 708-712, May 2002.
Paré Surgical, Inc., Brochure, Successful uses in approximation ligation & fixation using the Quik Stitch Endoscopic Suturing System, 2001.
Pories et al., Who Would Have Thought It? An Operation Proves to Be the Most Effective Therapy for Adult-Onset Diabetes Mellitus, Annals of Surgery, vol. 222, No. 3, pp. 339-352, Sep. 1995.
Redmond et al., Iatrogenic Intussusception: a Complication of Long Intestinal Tubes, American Journal of Gastroenterology, vol. 77, No. 1, pp. 39-42, Jan. 1982.
Rosen et al., Wilson-Cook sewing device: the device, technique, and preclinical studies, Gastrointestinal Endoscopy Clinics of North America, vol. 13, No. 1, pp. 103-108, Jan. 2003.
Rothstein et al., Endoscopic suturing for gastroesophageal reflux disease: clinical outcome with the Bard EndoCinch, Gastrointestinal Endoscopy Clinics of North America, vol. 13, No. 1, pp. 89-101, Jan. 2003.
Rubino et al., Effect of Duodenal-Jejunal Exclusion in a Non-obese Animal Model of Type 2 Diabetes, Annals of Surgery, vol. 239, No. 1, pp. 1-11, Jan. 2004.
Singh et al., Stents in the small intestine, Current Gastroenterology Reports (abstract), vol. 4, No. 5, pp. 383 391, Oct. 2002.
Stein et al., Three-dimensional pressure image and muscular structure of the human lower esophageal sphincter, Surgery, vol. 117, No. 6, pp. 692-698, Jun. 1995.
Sugermen et al., Weight Loss With Vertical Banded Gastroplasty and Roux-Y Gastric Bypass for Morbid Obesity With Selective Versus Random Assignment, The American Journal of Surgery, vol. 157, pp. 93 102, Jan. 1989.
Swain et al., An endoscopic stapling device: the development of a new flexible endoscopically controlled device for placing multiple transmural staples in gastrointestinal tissue, Gastrointestinal Endoscopy, vol. 35, No. 4, pp. 338-339, 1989.
Swain et al., Abstract, Design and testing of a new, small diameter, single stitch endoscopic sewing machine, Gastrointestinal Endoscopy, vol. 36, No. 2, pp. 213-214, Mar. 1990.
Swain et al., An endoscopically deliverable tissue-transfixing device for securing biosensors in the gastrointestinal tract, Gastrointestinal Endoscopy, vol. 40, No. 6, pp. 730-734, Nov. 1994.
Swain, Endoscopic suturing, Balliere's Clinical Gastroenterology, vol. 13, No. 1, pp. 97-108, 1999.
Swain et al., Bard EndoCinch: the device, the technique, and pre-clinical studies, Gastrointestinal Endoscopy Clinics of North America, vol. 13, No. 1, pp. 75-88, Jan. 2003.
Swain et al., Abstract, Radiocontrolled Movement of a Robot Endoscope in the Human Gastrointestinal Tract, Gastrointestinal Endoscopy, vol. 61, No. 5, p. AB101, Apr. 2005.
Yamamoto et al., A new method of enteroscopy—The double-balloon method, Canadian Journal of Gastroenterology, vol. 17, No. 4, pp. 273-274, Apr. 2003.
U.S. Appl. No. 10/698,148, Aug. 23, 2006 non-final office action.
U.S. Appl. No. 10/698,148, Jul. 24, 2007 final office action.
U.S. Appl. No. 10/698,148, Mar. 18, 2008 non-final office action.
U.S. Appl. No. 10/698,148, Jul. 21, 2008 final office action.
U.S. Appl. No. 10/698,148, Feb. 19, 2009 non-final office action.
U.S. Appl. No. 10/698,148, Jul. 9, 2009 final office action.
U.S. Appl. No. 10/698,148, Nov. 12, 2010 examiner's answer.
U.S. Appl. No. 10/698,148, Feb. 21, 2013 patent board decision.
U.S. Appl. No. 10/698,148, Jun. 6, 2013 non-final office action.
U.S. Appl. No. 10/698,148, Dec. 18, 2013 final office action.
U.S. Appl. No. 10/698,148, Feb. 18, 2015 notice of allowance.
EP patent application EP 03781672, Aug. 29, 2007 communication.
EP patent application EP 03781672, Jan. 9, 2009 communication.
PCT application PCT/US2003/034822, Apr. 2, 2004 ISR.
U.S. Appl. No. 10/998,424, Jun. 9, 2010 non-final office action.
U.S. Appl. No. 10/998,424, Nov. 14, 2010 final office action.
U.S. Appl. No. 14/738,597, Nov. 6, 2015 non-final office action.
U.S. Appl. No. 14/738,597, Sep. 21, 2016 notice of allowance.
U.S. Appl. No. 11/025,364, Nov. 17, 2006 non-final office action.
U.S. Appl. No. 11/025,364, Jan. 3, 2008 final office action.
U.S. Appl. No. 11/025,364, Feb. 12, 2009 non-final office action.
U.S. Appl. No. 11/025,364, Nov. 16, 2009 non-final office action.
U.S. Appl. No. 11/025,364, Aug. 6, 2010 final office action.
EP patent application EP 04816031, Sep. 22, 2008 supplemental search.
EP patent application EP 04816031, Feb. 19, 2009 communication.
EP patent application EP 04816031, Jun. 11, 2010 communication.
PCT application PCT/US2004/044049, May 30, 2007 ISR/WO.
U.S. Appl. No. 11/124,634, May 13, 2010 non-final office action.
U.S. Appl. No. 11/124,634, Nov. 30, 2010 final office action.
U.S. Appl. No. 11/124,634, Sep. 23, 2011 notice of allowance.
EP patent application EP 05747626, Sep. 18, 2008 supplemental search.
EP patent application EP 05747626, Aug. 25, 2009 communication.
EP patent application EP 05747626, Nov. 15, 2011 communication.
PCT application PCT/US2005/015795, Nov. 14, 2005 ISR/WO.
U.S. Appl. No. 11/400,724, Oct. 10, 2007 non-final office action.
U.S. Appl. No. 11/400,724, Mar. 24, 2008 final office action.
U.S. Appl. No. 11/400,724, Dec. 15, 2008 non-final office action.
U.S. Appl. No. 11/400,724, Jul. 9, 2009 non-final office action.
U.S. Appl. No. 11/400,724, Sep. 20, 2010 notice of allowance.
U.S. Appl. No. 11/548,605, Nov. 9, 2010 non-final office action.
U.S. Appl. No. 11/548,605, May 24, 2011 final office action.

(56) References Cited

OTHER PUBLICATIONS

U.S. Appl. No. 11/548,605, Mar. 15, 2012 notice of allowance.
EP patent application EP 07809011, Jun. 10, 2014 supplemental search.
PCT application PCT/US2007/008882, Dec. 26, 2007 ISR/WO.
U.S. Appl. No. 13/373,999, Jul. 9, 2012 non-final office action.
U.S. Appl. No. 13/373,999, May 24, 2013 final office action.
U.S. Appl. No. 13/373,999, Oct. 21, 2014 notice of allowance.
U.S. Appl. No. 14/634,548, Jul. 15, 2015 non-final office action.
U.S. Appl. No. 14/634,548, Jun. 15, 2016 final office action.
U.S. Appl. No. 13/476,884, Apr. 9, 2013 non-final office action.
U.S. Appl. No. 13/476,884, Dec. 24, 2013 non-final office action.
U.S. Appl. No. 13/476,884, Mar. 20, 2015 non-final office action.
U.S. Appl. No. 13/476,884, Jul. 20, 2015 final office action.
U.S. Appl. No. 13/476,884, Oct. 3, 2016 examiner's answer.
U.S. Appl. No. 11/431,040, Oct. 15, 2010 non-final office action.
U.S. Appl. No. 11/431,040, Jun. 21, 2011 notice of allowance.
U.S. Appl. No. 11/430,677, Apr. 2, 2009 non-final office action.
U.S. Appl. No. 11/430,677, Jan. 11, 2010 final office action.
U.S. Appl. No. 11/430,677, Sep. 23, 2010 notice of allowance.
U.S. Appl. No. 11/431,054, Oct. 27, 2010 non-final office action.
U.S. Appl. No. 11/430,275, Oct. 9, 2007 non-final office action.
U.S. Appl. No. 11/430,275, Sep. 16, 2008 final office action.
U.S. Appl. No. 11/430,275, Dec. 29, 2008 non-final office action.
U.S. Appl. No. 11/430,275, Jul. 21, 2009 final office action.
U.S. Appl. No. 11/430,275, Oct. 19, 2010 non-final office action.
U.S. Appl. No. 11/430,278, Jul. 3, 2007 non-final office action.
U.S. Appl. No. 11/430,278, Mar. 25, 2008 final office action.
U.S. Appl. No. 11/430,278, Jun. 4, 2008 non-final office action.
U.S. Appl. No. 11/430,278, Dec. 16, 2008 final office action.
U.S. Appl. No. 11/430,278, Oct. 20, 2009 non-final office action.
U.S. Appl. No. 11/430,278, Jul. 22, 2010 final office action.
U.S. Appl. No. 11/430,278, Jun. 20, 2011 notice of allowance.
U.S. Appl. No. 11/430,274, Oct. 5, 2009 non-final office action.
U.S. Appl. No. 11/430,274, May 11, 2010 final office action.
U.S. Appl. No. 11/430,274, Sep. 30, 2010 notice of allowance.
U.S. Appl. No. 11/429,934, May 26, 2010 non-final office action.
U.S. Appl. No. 11/429,934, Feb. 17, 2011 final office action.
U.S. Appl. No. 10/699,589, Dec. 13, 2004 non-final office action.
U.S. Appl. No. 10/699,589, Jun. 6, 2005 final office action.
U.S. Appl. No. 10/903,255, Aug. 23, 2006 non-final office action.
U.S. Appl. No. 10/903,255, Apr. 18, 2007 non-final office action.
U.S. Appl. No. 10/903,255, Sep. 24, 2007 final office action.
U.S. Appl. No. 10/903,255, Jan. 10, 2008 non-final office action.
U.S. Appl. No. 10/903,255, Nov. 14, 2008 final office action.
U.S. Appl. No. 10/903,255, Oct. 30, 2009 non-final office action.
U.S. Appl. No. 10/903,25, Feb. 22, 2010 non-final office action.
U.S. Appl. No. 10/903,255, Jun. 8, 2010 final office action.
U.S. Appl. No. 10/903,255, Jul. 27, 2010 notice of allowance.
U.S. Appl. No. 11/169,341, Dec. 13, 2006 non-final office action.
U.S. Appl. No. 11/236,212, Mar. 18, 2008 non-final office action.
U.S. Appl. No. 11/236,212, Oct. 7, 2009 final office action.
U.S. Appl. No. 11/236,212, Apr. 26, 2010 non-final office action.
U.S. Appl. No. 11/236,212, May 4, 2011 final office action.
U.S. Appl. No. 13/289,885, Aug. 15, 2012 non-final office action.
U.S. Appl. No. 11/123,889, May 24, 2010 non-final office action.
U.S. Appl. No. 11/123,889, Feb. 2, 2011 final office action.
U.S. Appl. No. 13/196,812, Jun. 18, 2012 non-final office action.
U.S. Appl. No. 13/196,812, Feb. 7, 2013 final office action.
U.S. Appl. No. 13/196,812, Oct. 17, 2013 non-final office action.
U.S. Appl. No. 13/196,812, May 5, 2014 final office action.
U.S. Appl. No. 11/125,820, May 30, 2008 non-final office action.
U.S. Appl. No. 11/125,820, Aug. 14, 2009 final office action.
U.S. Appl. No. 11/125,820, Feb. 4, 2010 non-final office action.
U.S. Appl. No. 11/125,820, Oct. 15, 2010 final office action.
U.S. Appl. No. 11/789,561, Mar. 29, 2010 non-final office action.
U.S. Appl. No. 11/789,561, Nov. 11, 2010 notice of allowance.
PCT application PCT/US2007/009956, Dec. 28, 2007 ISR/WO.
U.S. Appl. No. 13/018,179, Aug. 2, 2012 non-final office action.
U.S. Appl. No. 13/018,179, Mar. 12, 2013 final office action.
U.S. Appl. No. 13/018,179, Apr. 23, 2014 non-final office action.
U.S. Appl. No. 11/861,172, Nov. 10, 2008 non-final office action.
U.S. Appl. No. 11/861,172, Jul. 14, 2009 final office action.
U.S. Appl. No. 11/861,172, May 21, 2013 non-final office action.
U.S. Appl. No. 11/861,172, Apr. 11, 2014 notice of allowance.
U.S. Appl. No. 14/461,774, Apr. 17, 2015 final office action.
U.S. Appl. No. 14/461,774, Sep. 21, 2015 non-final office action.
U.S. Appl. No. 14/461,774, Apr. 29, 2016 final office action.
U.S. Appl. No. 11/861,156, Jun. 2, 2009 non-final office action.
U.S. Appl. No. 11/861,156, Dec. 31, 2009 final office action.
U.S. Appl. No. 11/861,156, Sep. 22, 2010 non-final office action.
U.S. Appl. No. 11/861,156, Jun. 23, 2011 final office action.
U.S. Appl. No. 11/861,156, Oct. 11, 2011 notice of allowance.
EP patent application EP 07843175, Oct. 1, 2013 supplemental search.
EP patent application EP 07843175, Jun. 11, 2014 communication.
PCT application PCT/US2007/079460, May 19, 2008 ISR/WO.
U.S. Appl. No. 12/136,003, Sep. 27, 2010 non-final office action.
U.S. Appl. No. 12/136,003, May 10, 2011 final office action.
U.S. Appl. No. 12/136,003, Mar. 13, 2012 notice of allowance.
EP patent application EP 08770415, Jul. 7, 2010 supplemental search.
PCT application PCT/US2008/066214, Oct. 1, 2008 ISR/WO.
U.S. Appl. No. 13/476,837, Oct. 14, 2014 non-final office action.
U.S. Appl. No. 12/135,989, Sep. 16, 2010 non-final office action.
U.S. Appl. No. 12/135,989, May 25, 2011 final office action.
U.S. Appl. No. 12/137,473, Sep. 29, 2010 non-final office action.
U.S. Appl. No. 12/137,473, May 31, 2011 final office action.
U.S. Appl. No. 12/137,473, Dec. 2, 2013 non-final office action.
U.S. Appl. No. 12/137,473, Jun. 25, 2014 final office action.
U.S. Appl. No. 12/137,473, Jan. 28, 2015 non-final office action.
EP patent application EP 08770736, May 23, 2011 supplemental search.
EP patent application EP 08770736, Mar. 23, 2015 communication.
PCT application PCT/US2008/066590, Dec. 5, 2008 ISR/WO.
U.S. Appl. No. 13/485,887, Aug. 6, 2013 non-final office action.
U.S. Appl. No. 13/485,887, Mar. 17, 2014 final office action.
U.S. Appl. No. 13/485,887, Oct. 2, 2014 notice of allowance.
U.S. Appl. No. 13/485,889, Aug. 8, 2013 non-final office action.
U.S. Appl. No. 13/485,893, Aug. 23, 2013 non-final office action.
U.S. Appl. No. 13/485,896, Mar. 5, 2015 non-final office action.
U.S. Appl. No. 13/485,896, Jul. 28, 2015 final office action.
U.S. Appl. No. 13/485,896, Apr. 26, 2016 notice of allowance.
U.S. Appl. No. 13/485,898, Jul. 3, 2013 non-final office action.
U.S. Appl. No. 13/485,898, Feb. 14, 2014 final office action.
U.S. Appl. No. 13/485,898, Jun. 6, 2014 non-final office action.
U.S. Appl. No. 13/485,898, Dec. 29, 2014 final office action.
U.S. Appl. No. 13/485,898, Jun. 18, 2015 notic eof allowance.
U.S. Appl. No. 13/743,285, Mar. 20, 2015 non-final office action.
U.S. Appl. No. 13/743,287, Mar. 23, 2015 non-final office action.
U.S. Appl. No. 13/743,287, Jul. 9, 2015 final office action.
EP patent application EP 13796584, Feb. 18, 2016 communication.
PCT application PCT/US2013/043741, Dec. 2, 2013 ISR/WO.
U.S. Appl. No. 14/315,330, Feb. 12, 2016 non-final office action.
U.S. Appl. No. 14/139,859, Jul. 17, 2015 non-final office action.
U.S. Appl. No. 15/000,959, Oct. 6, 2016 non-final office action.
U.S. Appl. No. 14/164,112, Jan. 14, 2016 non-final office action.
PCT application PCT/US2014/013069, Apr. 17, 2014 ISR/WO.
U.S. Appl. No. 14/208,642, Jan. 11, 2016 non-final office action.
U.S. Appl. No. 14/208,642, Nov. 16, 2016 notice of allowance.
U.S. Appl. No. 14/208,642, Feb. 7, 2017 notice of allowance.
PCT application PCT/US2015/058690, Mar. 17, 2016 ISR/WO.
PCT application PCT/US2015/058691, Jan. 27, 2016 ISR/WO.

* cited by examiner

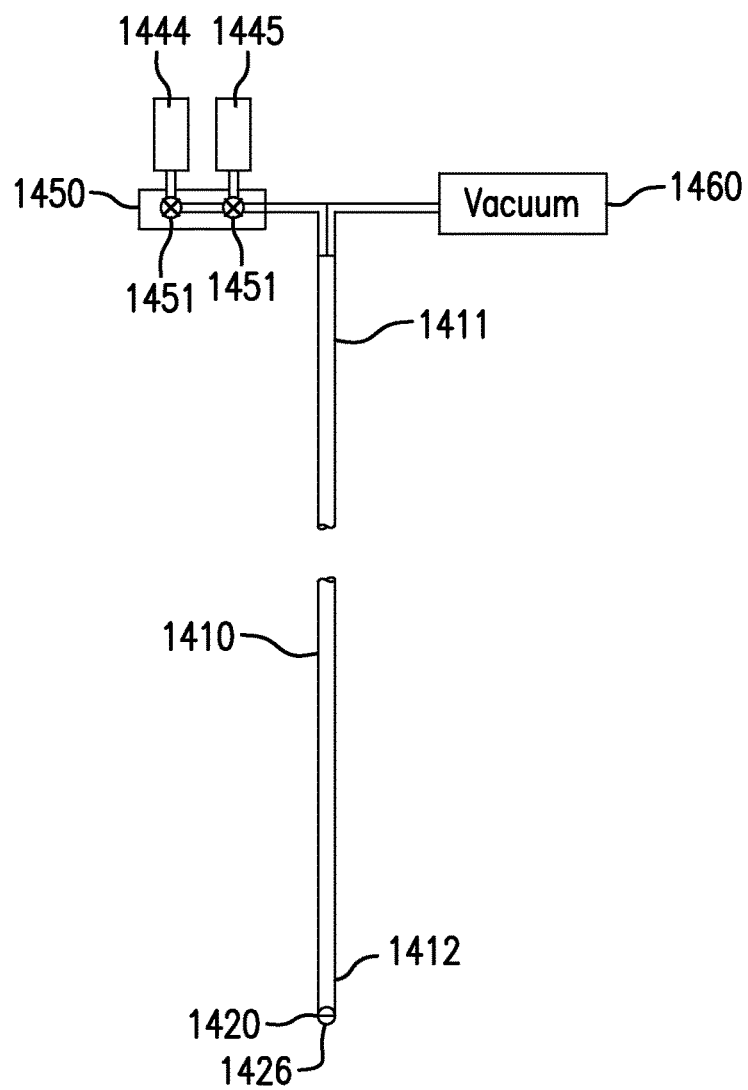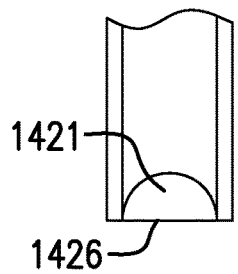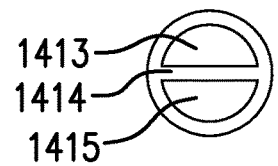
FIG.5A
FIG.5B
FIG.5C

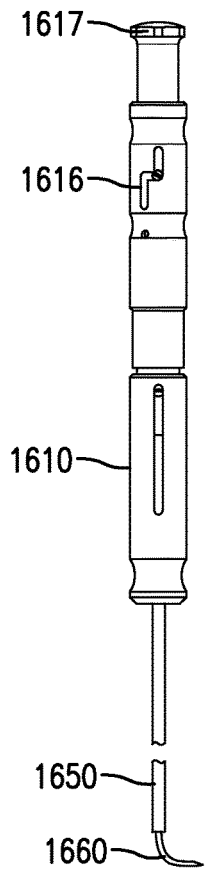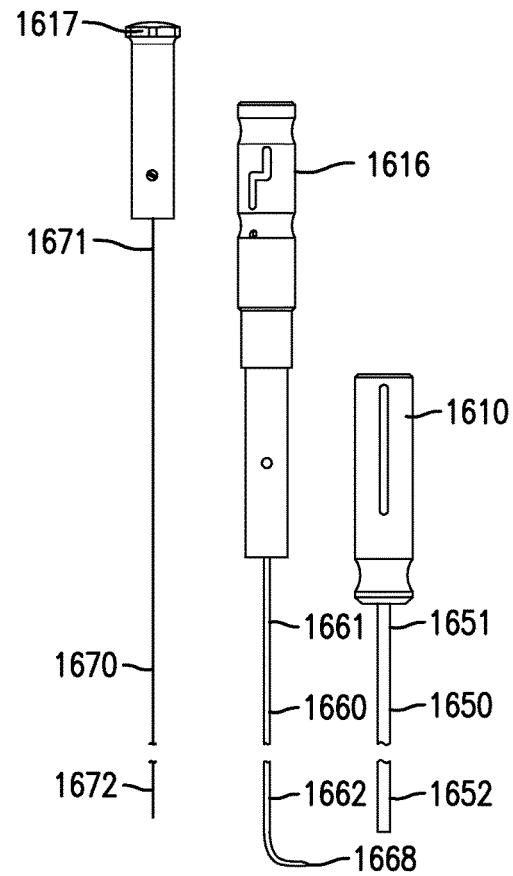
FIG.12A  FIG.12B
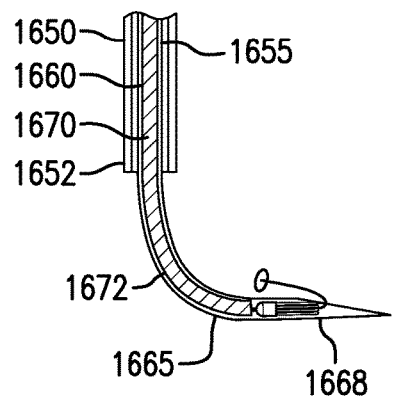
FIG.12C

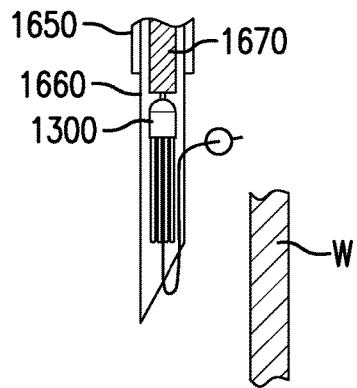
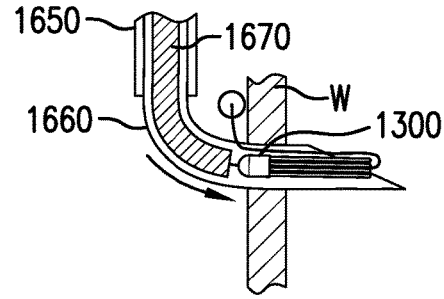
FIG.13A  FIG.13B
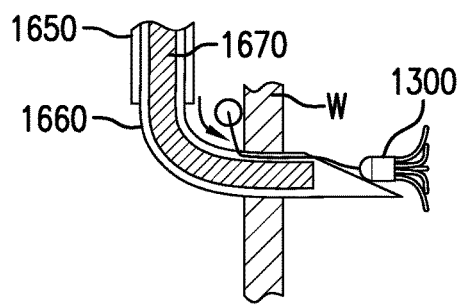
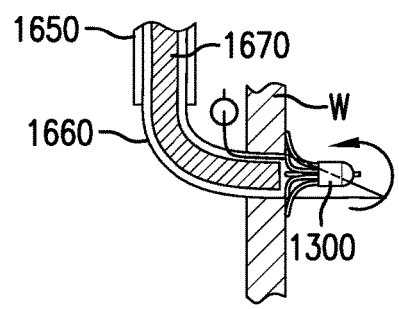
FIG.13C  FIG.13D
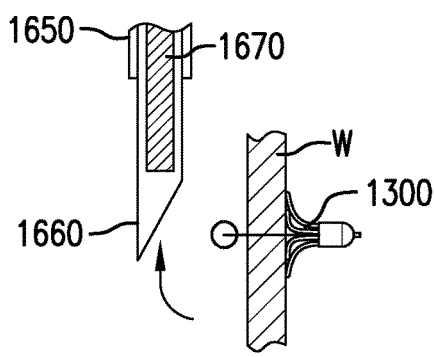
FIG.13E

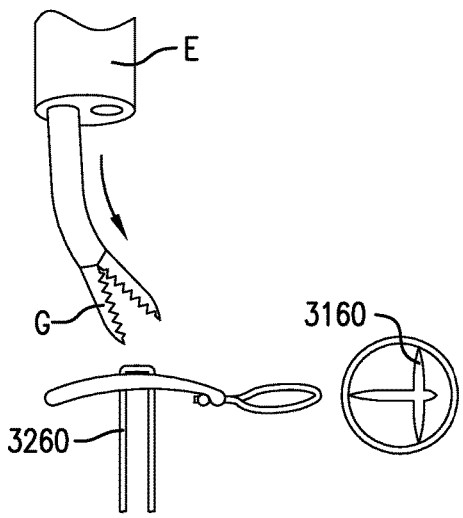
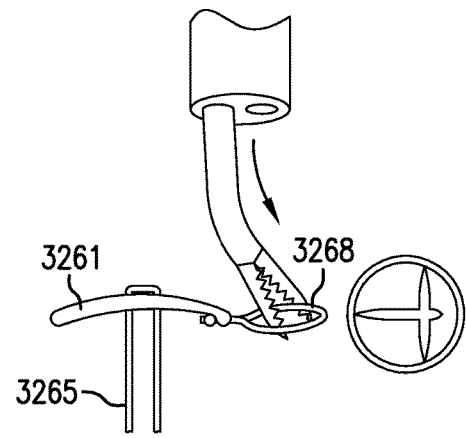
FIG.21A    FIG.21B
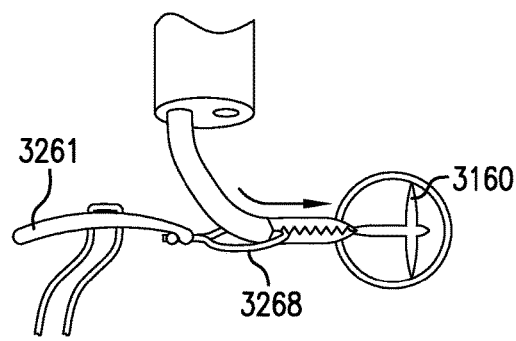
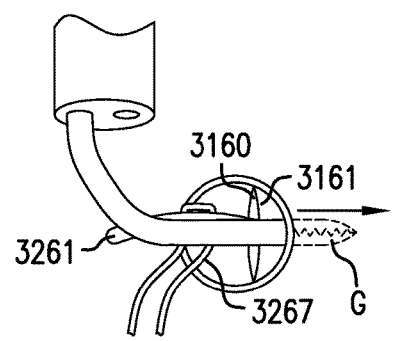
FIG.21C    FIG.21D

DEVICES AND METHODS FOR GASTROINTESTINAL BYPASS

CROSS-REFERENCE TO RELATED APPLICATIONS

This application is a continuation-in-part of U.S. patent application Ser. Nos. 13/485,887, 13/485,889, 13/485,893, 13/485,896, and 13/485,898, all filed on May 31, 2012. This application is also a continuation-in-part of U.S. patent application Ser. Nos. 13/743,285 and 13/743,287, both filed on Jan. 16, 2013. The applications listed above are hereby incorporated by reference in their entireties.

BACKGROUND

Diabetes, heart disease, and other obesity-related conditions may be treated surgically with bariatric procedures such as jejuno-ileal bypass, jejuno-colic bypass, biliopancreatic diversion, gastric bypass, and gastroplasty. These procedures may be effective for weight control and treatment of chronic conditions. However, these procedures carry with them substantial shortcomings, including the risk of infection and other risks accompanying surgery. Some of these procedures induce radical permanent changes to the gastrointestinal anatomy, thus foreclosing subsequent surgical intervention.

What is needed are devices and methods that use non-surgical techniques that avoid the risks associated with gastrointestinal bypass surgery. What is also needed are devices and methods for gastrointestinal bypass that allow for additional or revision procedures to be performed. What is also needed are devices and methods for gastrointestinal bypass that are reversible.

SUMMARY

A method of treating a patient is described. In one embodiment, the method comprises providing a gastrointestinal bypass device including a gastrointestinal cuff and a gastrointestinal sleeve. A distal portion of the gastrointestinal cuff may be coupled to a proximal portion of the gastrointestinal sleeve. The method also comprises delivering the gastrointestinal sleeve to position a distal portion of the gastrointestinal sleeve in an intestine of the patient, positioning a proximal portion of the gastrointestinal cuff in an esophagus of the patient, and providing a tissue anchor. The tissue anchor may include a tension element, a proximal retention element coupled to a proximal portion of the tension element, and a distal retention element coupled to a distal portion of the tension element. The proximal retention element may be configured to be coupled to the gastrointestinal cuff. The distal retention element may be configured to be deployed on a distal side of a wall of the esophagus. The method also comprises delivering the distal retention element through the gastrointestinal cuff and through a wall of the esophagus at an attachment point to anchor the gastrointestinal cuff to the wall of the esophagus.

BRIEF DESCRIPTION OF THE DRAWINGS

FIGS. 5A-5C show one embodiment of a tissue marking device 1400.

FIGS. 12A-12C show one embodiment of an anchor delivery device 1600.

FIGS. 13A-13E show one embodiment of a method for using anchor delivery device 1600.

FIGS. 20E-20G, 20H-20I, and 20J-20K show various embodiments of an attachment element 3260.

FIGS. 21A-21F show one embodiment of a method for using attachment element 3260 to attach a device through an attachment opening 3160 formed in a wall.

DESCRIPTION

Figure 1A:
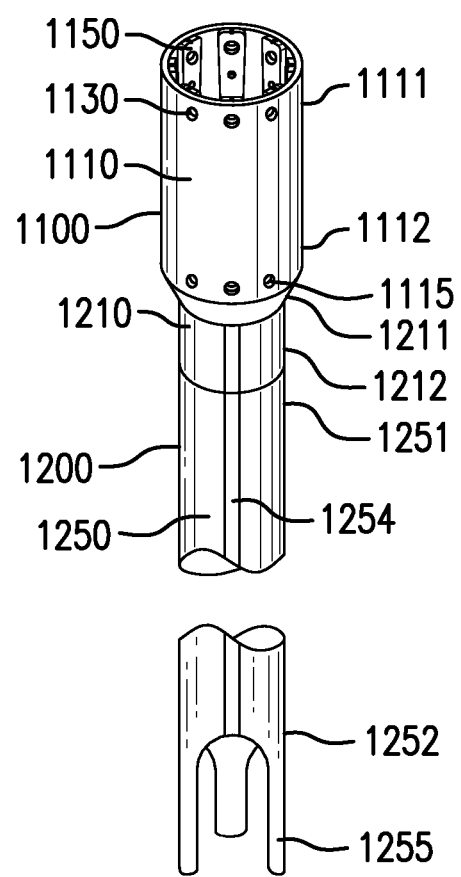
FIGS. 1A-1C show one embodiment of a gastrointestinal bypass device 1000.
Figure 1B:
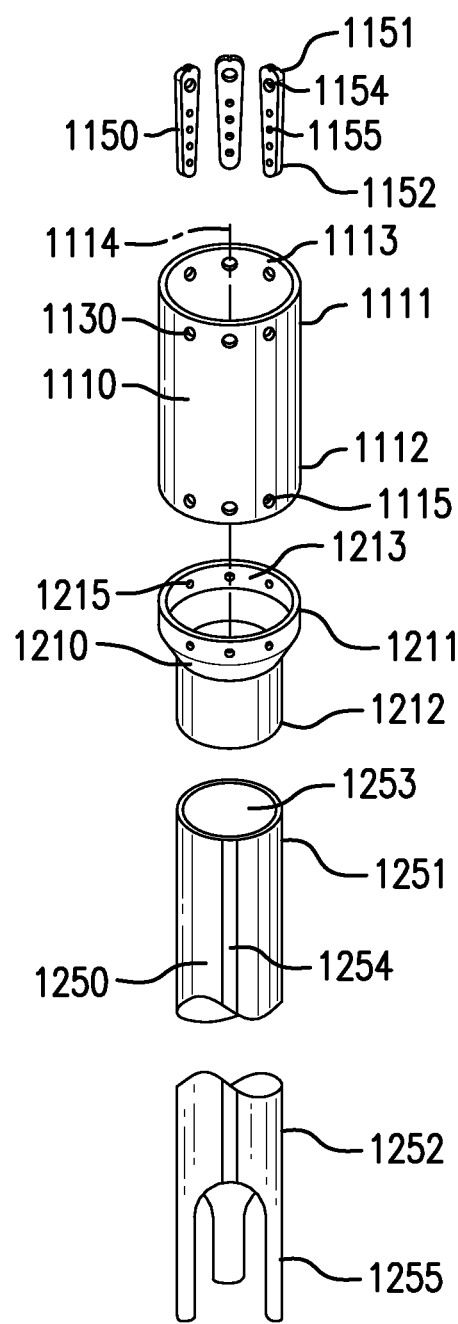
Figure 1C:
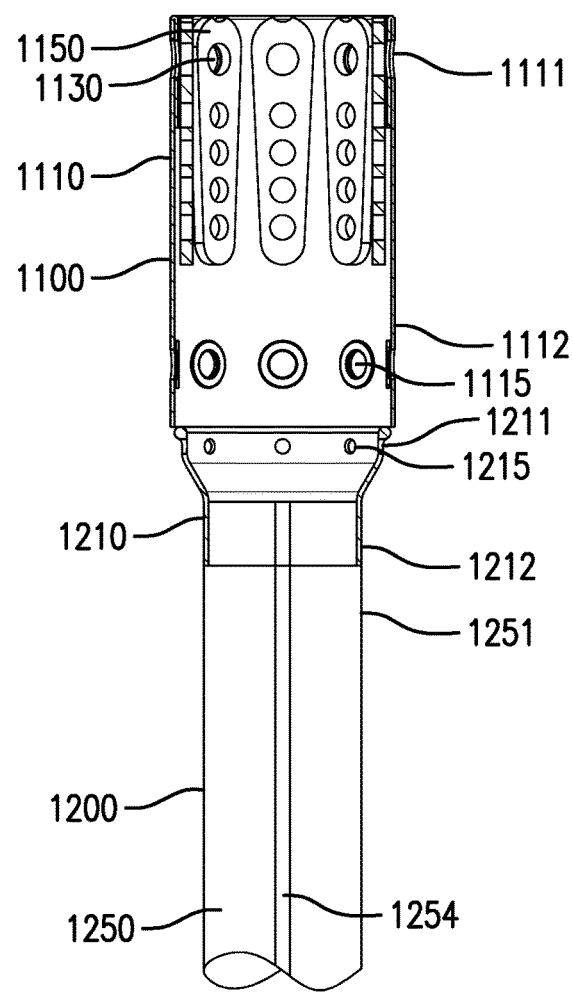
Figure 1C:
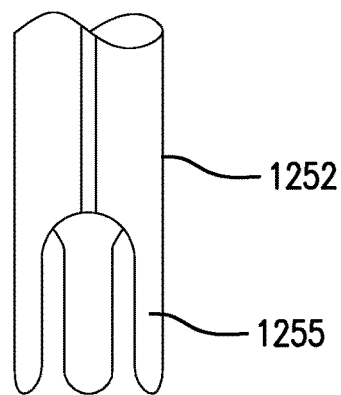
Figure 1D:
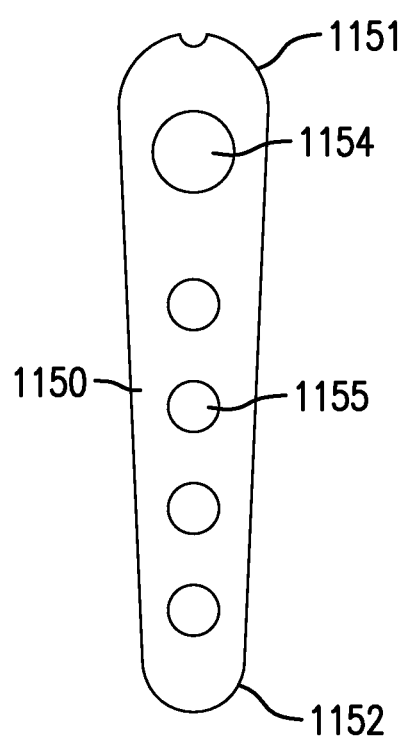
FIG. 1D shows an enlarged view of a strut 1150.

FIGS. 1A-1C show one embodiment of a gastrointestinal bypass device 1000. FIG. 1A shows a perspective view of gastrointestinal bypass device 1000. FIG. 1B shows an exploded view of gastrointestinal bypass device 1000. FIG. 1C shows a cross-sectional view of gastrointestinal bypass device 1000. FIG. 1D shows an enlarged view of a strut 1150.

Gastrointestinal bypass device 1000 may include a gastrointestinal cuff 1100 and a gastrointestinal sleeve 1200.

Cuff 1100 may be configured to be attached in the esophagus. Cuff 1100 may be attached at or near the gastroesophageal junction. Alternatively, cuff 1100 may be attached proximal to the gastroesophageal junction, in the proximal stomach, or at some other location. For example, cuff 1100 may be attached within about 3 cm, 2.5 cm, 2 cm, 1.5 cm, 1 cm, 0.5 cm, above, below, or at the GEJ or squamocolumnar junction (SCJ or Z-line). As another example, cuff 1100 may be attached up to 5 cm above the diaphragm. Some non-limiting locations for attachment can be found, for example, in U.S. Pat. Pub. No. 2007/0198174 to Dann et al., which is hereby incorporated by reference in its entirety (e.g., at paras. [0131] to [0147]). Cuff 1100 may be sufficiently flexible to expand and collapse to conform with the inside of the esophagus. Cuff 1100 directs food and liquids into sleeve 1200, and provides a structure to which sleeve 1200 may be attached. Cuff 1100 may be attached using tissue anchors.

Cuff 1100 may include a liner 1110, a plurality of anchor holes 1130, and a plurality of struts 1150.

Liner 1110 may include a proximal portion 1111, a distal portion 1112, a lumen 1113, and a longitudinal axis 1114. Liner 1110 may be tubular and may have a uniform width. Alternatively, liner 1110 may taper or change in width. Liner 1110 may be made of material that is flexible. This flexibility allows the attachment area, such as the lower esophageal sphincter, to open and close substantially normally. Liner 1110 may be made of a material that is thin, allowing it to collapse into a smaller profile. This smaller profile allows the attachment area, such as the lower esophageal sphincter, to close substantially normally, and also helps liner 1110 to be collapsed for delivery. Liner 1110 may include a single layer of material. Alternatively, liner 1110 may include a plurality of layers. Liner 1110 may be at least semi-permeable to liquids and/or solids. This semi-permeability may allow some food to reach the stomach, and may help the stomach maintain some residual functionality. This semi-permeability may allow medications to reach the stomach. Liner 1110 may be made of DACRON or any other suitable material. In one embodiment, liner 1110 may have a length of approximately 20 mm to 80 mm. Liner 1110 may include a sleeve-coupling element, e.g., suture holes 1115 formed at distal portion 1112.

A coupling mechanism, e.g., anchor holes 1130 may be formed at or near proximal portion 1111 of liner 1110. Anchor holes 1130 are configured to receive tissue anchors. Anchor holes 1130 may be marked with a contrasting color, radiopaque marker, or other means to aid visualization. Anchor holes 1130 may be marked with stitching, ink, or other suitable marking. Anchor holes 1130 may be used as a placement template for tissue anchors. Anchor holes 1130 may be evenly spaced about a circumference of liner 1110. Evenly spaced anchor holes 1130 may help to distribute forces among the tissue anchors, prevent concentration of forces in a small number of tissue anchors, and enhance conformance of liner 1110 to an inside (e.g., luminal wall) of the esophagus. Alternatively, anchor holes 1130 may be spaced in any manner about a circumference of liner 1110. Anchor holes 1130 may be substantially coplanar. Anchor holes 1130 may be arranged in a plane substantially perpendicular to longitudinal axis 1114, or angled to longitudinal axis 1114. A substantially coplanar arrangement may help to prevent concentration of forces in a small number of tissue anchors. Alternatively, anchor holes 1130 may be arranged in a staggered fashion.

Struts 1150 each include a proximal portion 1151 and a distal portion 1152. Struts 1150 may be elongate and substantially straight. Alternatively, struts 1150 may be curved or any other suitable shape. Struts 1150 may be coupled to an inner surface of liner 1110. Alternatively, struts 1150 may be coupled to an outer surface of liner 1110 or between layers of liner 1110 to reduce obstructions on an inner surface of liner 1110. Struts 1150 may be coupled to liner 1110 longitudinally. Alternatively, struts 1150 may be coupled to liner 1110 at an angle of 1 to 30 degrees or more with respect to longitudinal axis 1114 of liner 1110. Struts 1150 may include a first attachment element, e.g., an anchor hole 1154 at or near proximal portion 1151. Anchor holes 1154 of struts 1150 may be aligned with anchor holes 1130 of liner 1110. Anchor holes 1154 of struts 1150 may reinforce anchor holes 1130 of liner 1110 and prevent tissue anchors from pulling through. Struts 1150 may include a second attachment element, e.g., suture holes 1155, and struts 1150 may be coupled to liner 1110 with sutures stitched through suture holes 1155 and liner 1110. Alternatively, struts 1150 may be coupled to liner 1110 with adhesives, thermal bonding, ultrasonic or laser welding, pockets formed between layers of liner 1110, or other suitable ways. Struts 1150 may have a uniform cross-section. Alternatively, struts 1150 may have a non-uniform cross-section which varies wider, narrower, thicker, and/or thinner. For example, struts 1150 may each have a proximal portion 1151 and/or a distal portion 1152 which are thinner. This thinner cross-section allows proximal portion 1151 and/or distal portion 1152 to be more flexible. Struts 1150 may be made of a plastic such as PEEK, a metal, or any other suitable material.

Struts 1150 may reduce longitudinal stretching of liner 1110. Prograde forces such as peristaltic forces at distal portion 1112 of liner 1110 are transferred by struts 1150 to anchor holes 1154 and tissue anchors, to advantageously redistribute forces and minimize focal wear or failure points. Struts 1150 may also prevent inversion of liner 1110. Retrograde forces such as vomiting or retching forces at distal portion 1112 of liner 1110 are resisted by struts 1150, helping to maintain liner 1110 in proper implanted position.

Sleeve 1200 is configured to be coupled to cuff 1100, either in an integrally formed or removably coupled manner. Sleeve 1200 directs food and liquids into the intestine. Sleeve 1200 may include a coupling 1210 and a tube 1250.

Coupling 1210 directs food and liquids from cuff 1100 to tube 1250. Coupling 1210 includes a proximal portion 1211, a distal portion 1212, and a lumen 1213. A coupling element, e.g., suture holes 1215 may be formed at or near proximal portion 1211 to allow coupling 1210 be coupled with sutures to a complementary cuff-coupling element, e.g., suture holes 1115 in liner 1110. Proximal portion 1211 may have a width that is the same or substantially the same as liner 1110, or in some embodiments taper down in width to restrict the flow of food and liquids through coupling 1210, which may help to create a feeling of fullness. Distal portion 1212 may have a uniform width. Alternatively, proximal portion 1211 and distal portion 1212 may have a uniform width. Coupling 1210 may be made of a material that is flexible, but does not stretch substantially in a radial or longitudinal direction. Coupling 1210 may be made of a polyurethane elastomer such as PELLETHANE, or any other suitable material.

Tube 1250 includes a proximal portion 1251, a distal portion 1252, and a lumen 1253. Proximal portion 1251 of tube 1250 may be coupled to distal portion 1212 of coupling 1210 with an interference fit, heat bonded, and/or other suitable methods. Alternatively, tube 1250 may be formed integrally with coupling 1210. Tube 1250 may have a uniform width. Alternatively, tube 1250 may taper or change in width. Tube 1250 may allow food and liquids to bypass the stomach and/or part of the intestine. Tube 1250 may allow foods and liquids to be bypassed into the duodenum, jejunum, or other part of the intestine. In one embodiment, tube 1250 may have a length of approximately 80 cm to 450 cm, a diameter of approximately 15 mm to 25 mm, and/or a thickness of about 0.05 mm to about 0.5 mm, such as about 0.15 mm.

Tube 1250 may be made of a material that is floppy or flaccid, but does not stretch substantially in a radial direction. Thus, tube 1250 may be flexible and compliant inwardly to allow peristaltic forces to act on its contents, but will not balloon outwardly. Tube 1250 may also not stretch substantially in a longitudinal direction. Tube 1250 may be made of a polyurethane elastomer such as PELLETHANE, or any other suitable material. Tube 1250 may be impermeable or semi-permeable. Tube 1250 may allow nutrients and medications inside tube 1250 to pass outward. Alternatively or in addition, tube 1250 may allow digestive juices and hormones outside tube 1250 to pass inward. Tube 1250 or portions of tube 1250 may be biodegradable. Tube 1250 with a plurality of biodegradable portions may be configured such that each portion degrades at a different rate.

Tube 1250 may include one or more coatings to resist calcification, deliver medications, provide lubriciousness, and/or provide other desired properties. These coatings may include parylene, polyvinylpyrrolidone (PVP), and/or other suitable materials. Tube 1250 may include an electrical stimulation element to resist calcification and promote motility and satiety. Various electrical stimulation elements that can be utilized or modified for use with the systems and methods disclosed herein are described, for example, in U.S. Pat. No. 7,881,797 to Griffin et al., which is hereby incorporated by reference in its entirety. Tube 1250 may be made up of one or more sections which may be coupled or uncoupled to adjust a length of tube 1250. Tube 1250 may include one, two, or more additional lumens interior to, exterior to, or within walls of tube 1250 for delivery of medications, access for imaging devices for visual monitoring, and access for diagnostic sampling. Tube 1250 may have additional lumens which open at different points along the length of tube 1250 for targeted delivery or access.

Tube 1250 may include a radiopaque marker 1254. Radiopaque marker 1254 may be one or more longitudinal stripes which run along all or part of the length of tube 1250. Radiopaque marker 1254 may be configured to help prevent or reduce kinking and twisting of tube 1250. For example, radiopaque marker 1254 may be thicker and/or wider toward proximal portion 1251 of tube 1250, where kinking and twisting may be more pronounced. Alternatively, radiopaque marker 1254 may be a helical stripe, circumferential bands, or other suitable configuration. Radiopaque marker 1254 may be coupled to an inside surface of tube 1250 to help maintain at least some patency of lumen 1253 and prevent lumen 1253 from closing completely when tube 1250 is kinked or twisted. Alternatively, radiopaque marker 1254 may be coupled to an outside surface of tube 1250. Various embodiments, features, materials and parameters of cuffs, sleeves, anchors, and other components that can be used or modified for use with those disclosed herein are described, for example, in the following patents and publications, each of which are incorporated by reference in their entireties: U.S. Pat. Pub. No. 2007/0198074 to Dann et al., U.S. Pat. No. 8,070,743 to Kagan et al., U.S. Pat. Pub. No. 2009/0149871 to Kagan et al., U.S. Pat. Pub. No. 2004/0092892 to Kagan et al., U.S. Pat. Pub. No. 2006/0155375 to Kagan et al., U.S. Pat. Pub. No. 2006/0015125 to Swain, U.S. Pat. Pub. No. 2006/0020254 to von Hoffmann, U.S. Pat. No. 8,118,774 to Dann et al., U.S. Pat. Pub. No. 2009/0012553 to Swain et al., U.S. Pat. Pub. No. 2009/0012544 to Thompson et al., and U.S. Pat. Pub. No. 2009/0012541 to Dahl et al.

Tube 1250 may include one, two, three, or more tails 1255 at distal portion 1252. Tails 1255 may be folded over each other and cinched with a grasping element, such as a loop snare, to seal distal portion 1255 of tube 1250 during deployment of sleeve 1200. Tails 1255 may be as described, for example, in U.S. Pat. No. 8,118,774 to Dann et al., which is hereby incorporated by reference in its entirety.

Figure 2A:
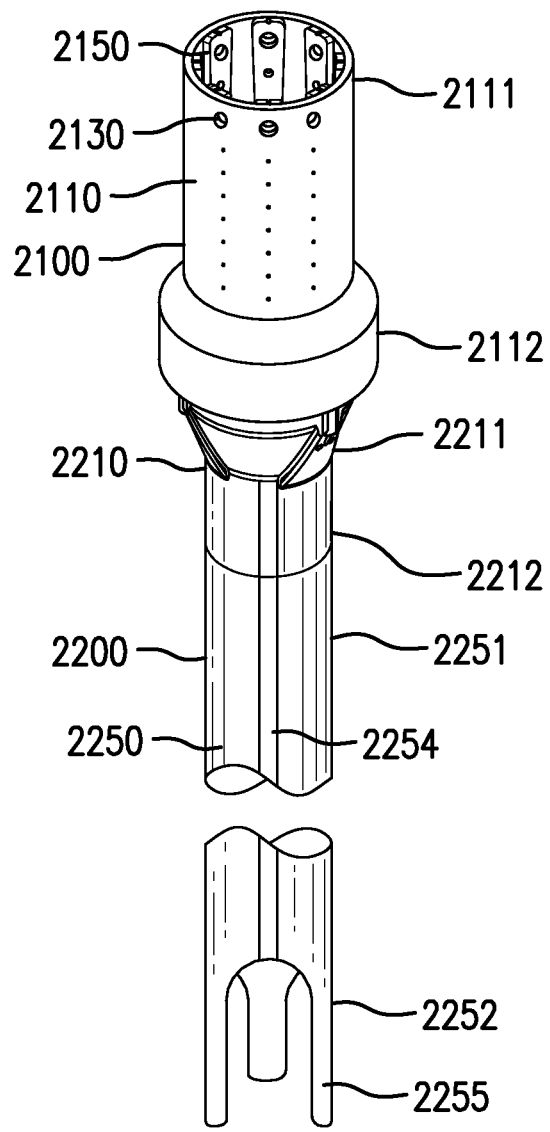
FIGS. 2A-2C show another embodiment of a gastrointestinal bypass device 2000.
Figure 2B:
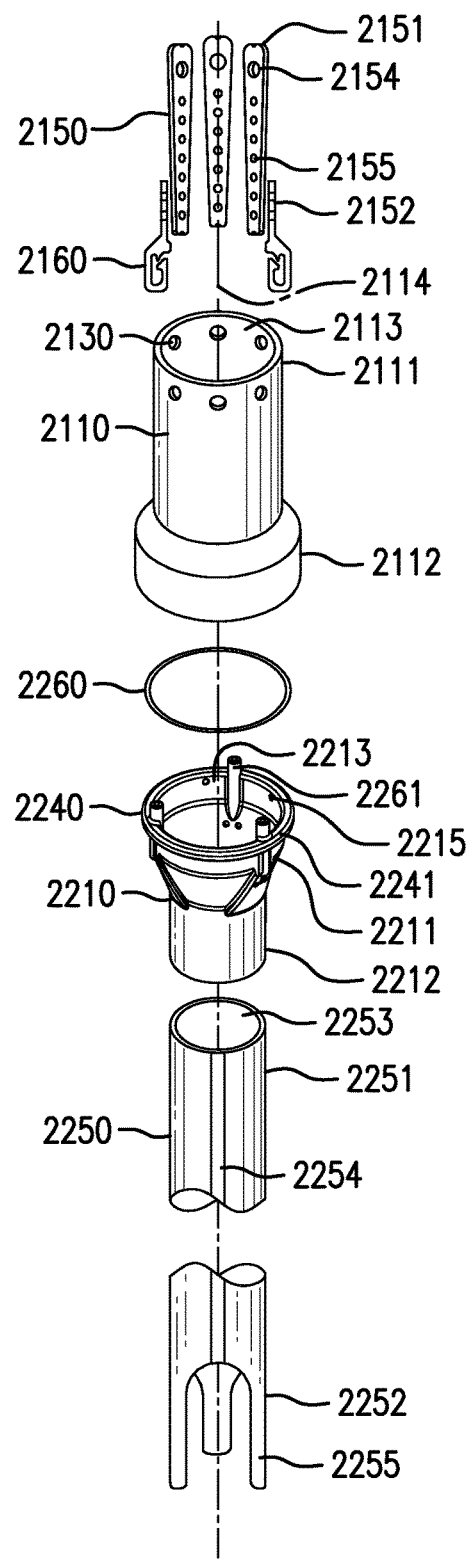
Figure 2C:
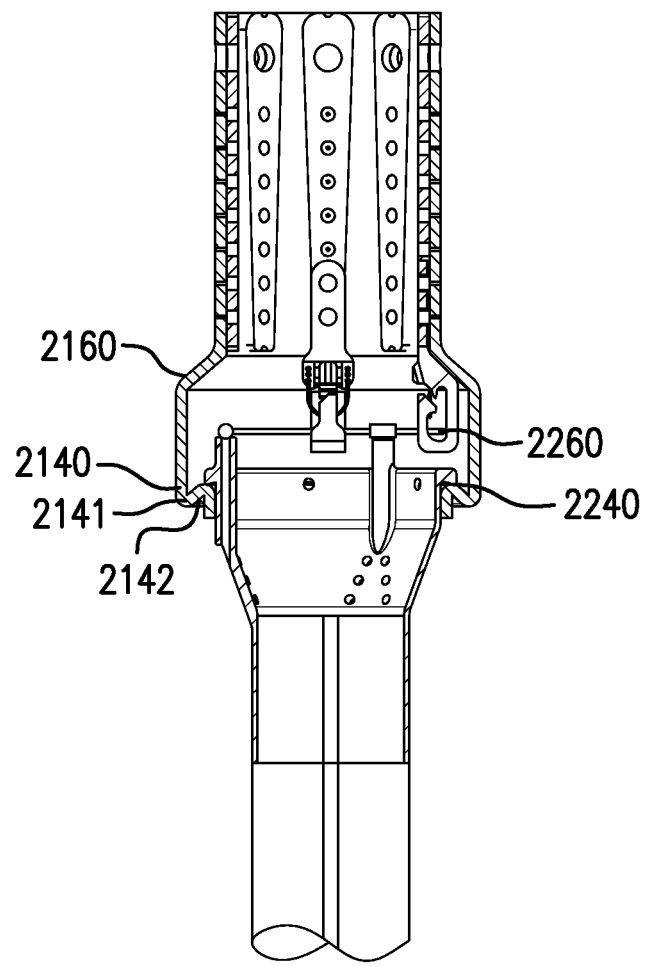
Figure 2C:
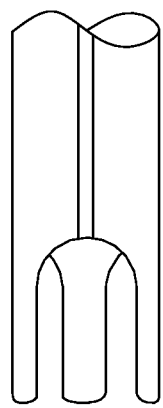
Figure 2D:
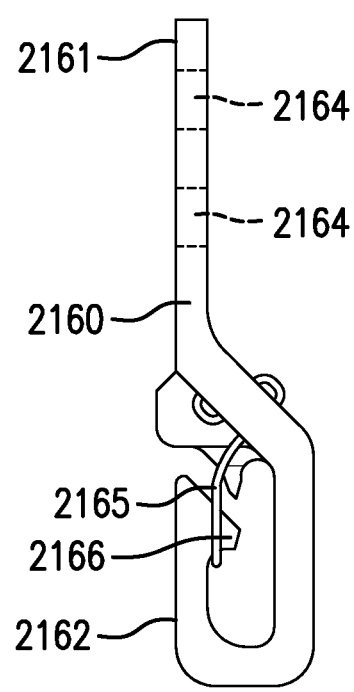
FIG. 2D shows an enlarged view of a hook 2160.

FIGS. 2A-2C show another embodiment of a gastrointestinal bypass device 2000. FIG. 2A shows a perspective view of gastrointestinal bypass device 2000. FIG. 2B shows an exploded view of gastrointestinal bypass device 2000. FIG. 2C shows a cross-sectional view of gastrointestinal bypass device 2000. FIG. 2D shows an enlarged view of a hook 2160.

Gastrointestinal bypass device 2000 may include a gastrointestinal cuff 2100 and a gastrointestinal sleeve 2200.

Cuff 2100 may be configured to be attached in the esophagus. Cuff 2100 may be attached at or near the gastroesophageal junction. Alternatively, cuff 2100 may be attached proximal to the gastroesophageal junction, in the proximal stomach, or at some other location. For example, cuff 2100 may be attached within about 3 cm, 2.5 cm, 2 cm, 1.5 cm, 1 cm, 0.5 cm, above, below, or at the GEJ or squamocolumnar junction (SCJ or Z-line). As another example, cuff 1100 may be attached up to 5 cm above the diaphragm. Some non-limiting locations for attachment can be found, for example, in U.S. Pat. Pub. No. 2007/0198174 to Dann et al., which is hereby incorporated by reference in its entirety (e.g., at paras. [0131] to [0147]). Cuff 2100 may be sufficiently flexible to expand and collapse to conform with the inside of the esophagus. Cuff 2100 directs food and liquids into sleeve 2200, and provides a structure to which sleeve 2200 may be attached. Cuff 2100 may be attached using tissue anchors.

Cuff 2100 may include a liner 2110, a plurality of anchor holes 2130, a retainer 2140, a plurality of struts 2150, and one or more hooks 2160.

Liner 2110 may include a proximal portion 2111, a distal portion 2112, a lumen 2113, and a longitudinal axis 2114. Liner 2110 may be tubular and may have a uniform width. Alternatively, liner 2110 may taper or change in width. Liner 2110 may be made of material that is flexible. This flexibility allows the attachment area, such as the lower esophageal sphincter, to open and close substantially normally. Liner 2110 may be made of a material that is thin, allowing it to collapse into a smaller profile. This smaller profile allows the attachment area, such as the lower esophageal sphincter, to close substantially normally, and also helps liner 2110 to be collapsed for delivery. Liner 2110 may include a single layer of material. Alternatively, liner 2110 may include a plurality of layers. Liner 2110 may be at least semi-permeable to liquids and/or solids. This semi-permeability may allow some food to reach the stomach, and may help the stomach maintain some residual functionality. This semi-permeability may allow medications to reach the stomach. Liner 2110 may be made of DACRON or any other suitable material. In one embodiment, liner 2110 may have a length of approximately 20 mm to 80 mm.

A coupling mechanism, e.g. anchor holes 2130 may be formed at or near proximal portion 2111 of liner 2110. Anchor holes 2130 are configured to receive tissue anchors. Anchor holes 2130 may be marked with a contrasting color, radiopaque marker, or other means to aid visualization. Anchor holes 2130 may be marked with stitching, ink, or other suitable marking. Anchor holes 2130 may be used as a placement template for tissue anchors. Anchor holes 2130 may be evenly spaced about a circumference of liner 2110. Evenly spaced anchor holes 2130 may help to distribute forces among the tissue anchors, prevent concentration of forces in a small number of tissue anchors, and enhance conformance of liner 2110 to an inside (e.g., luminal wall) of the esophagus. Alternatively, anchor holes 2130 may be spaced in any manner about a circumference of liner 2110. Anchor holes 2130 may be substantially coplanar. Anchor holes 2130 may be arranged in a plane substantially perpendicular to longitudinal axis 2114, or angled to longitudinal axis 2114. A substantially coplanar arrangement may help to prevent concentration of forces in a small number of tissue anchors. Alternatively, anchor holes 2130 may be arranged in a staggered fashion.

Retainer 2140 may be coupled to distal portion 2112 of liner 2110. Retainer 2140 may be collapsible radially inwardly but not expandable radially outwardly. Retainer 2140 may be a circumferential channel formed in distal portion 2112 of liner 2110 by one or more folds 2141. Folds 2141 may be secured by a suture 2142, adhesive, or other means. Folds 2141 may be made more rigid by applying a stiffening substance to distal portion 2112 and/or folds 2141. The stiffening substance may be silicone or other suitable substance. Alternatively, retainer 2140 may be made of plastic or other suitable material, and coupled to distal portion 2112 of liner 2110.

Struts 2150 each include a proximal portion 2151 and a distal portion 2152. Struts 2150 may be elongate and substantially straight. Alternatively, struts 2150 may be curved or any other suitable shape. Struts 2150 may be coupled to an inner surface of liner 2110. Alternatively, struts 2150 may be coupled to an outer surface of liner 2110 or between layers of liner 2110 to reduce obstructions on an inner surface of liner 2110. Struts 2150 may be coupled to liner 2110 longitudinally. Alternatively, struts 2150 may be coupled to liner 2110 at an angle of 1 to 30 degrees or more with respect to longitudinal axis 2114 of liner 2110. Struts 2150 may include a first attachment element, e.g., an anchor hole 2154 at or near proximal portion 2151. Anchor holes 2154 of struts 2150 may be aligned with anchor holes 2130 of liner 2110. Anchor holes 2154 of struts 2150 may reinforce anchor holes 2130 of liner 2110 and prevent tissue anchors from pulling through. Struts 2150 may include a second attachment element, e.g., suture holes 2155, and struts 2150 may be coupled to liner 2110 with sutures stitched through suture holes 2155 and liner 2110. Alternatively, struts 2150 may be coupled to liner 2110 with adhesives, thermal bonding, ultrasonic or laser welding, pockets formed between layers of liner 2110, or other suitable ways. Struts 2150 may have a uniform cross-section. Alternatively, struts 2150 may have a non-uniform cross-section which varies wider, narrower, thicker, and/or thinner. For example, struts 2150 may each have a proximal portion 2151 and/or a distal portion 2152 which are thinner. This thinner cross-section allows proximal portion 2151 and/or distal portion 2152 to be more flexible. Struts 2150 may be made of a plastic such as PEEK, a metal, or any other suitable material.

Struts 2150 may reduce longitudinal stretching of liner 2110. Prograde forces such as peristaltic forces at distal portion 2112 of liner 2110 are transferred by struts 2150 to anchor holes 2154 and tissue anchors, to advantageously redistribute forces and minimize focal wear or failure points. Struts 2150 may also prevent inversion of liner 2110. Retrograde forces such as vomiting or retching forces at distal portion 2112 of liner 2110 are resisted by struts 2150, helping to maintain liner 2110 in proper implanted position.

Hooks 2160 may each include a proximal portion 2161 and a distal portion 2162. Proximal portion 2161 may be coupled to distal portion 2152 of strut 2150. Hooks 2160 may include one or more suture holes 2164 for stitching to liner 2110 and/or distal portion 2152 of strut 2150. Alternatively, hooks 2160 may be coupled to liner 2110 or one or more struts 2150 with an adhesive or other suitable methods. Alternatively, hooks 2160 may be formed as part of one or more struts 2150. Hooks 2160 may each include a retainer 2165 and a barb 2166. Distal portions 2162 may be configured so that they do not substantially protrude beyond struts 2150 into an interior of liner 2110. Distal portion 2112 of liner 2110 may be enlarged in diameter or otherwise configured to accommodate hooks 2160.

Sleeve 2200 is configured to be coupled to cuff 2100, either in an integrally formed or removably coupled manner. Sleeve 2200 directs food and liquids into the intestine. Sleeve 2200 may include a coupling 2210, a ring 2240, a tube 2250, and a halo 2260.

Coupling 2210 directs food and liquids from cuff 2100 to tube 2250. Coupling 2210 includes a proximal portion 2211, a distal portion 2212, and a lumen 2213. Drawstring holes 2215 may be formed at or near proximal portion 2211. Proximal portion 2211 may have a width that is the same or substantially the same as liner 2110, or in some embodiments taper down in width to restrict the flow of food and liquids through coupling 2210, which may help to create a feeling of fullness. Distal portion 2212 may have a uniform width. Alternatively, proximal portion 2211 and distal portion 2212 may have a uniform width. Coupling 2210 may be made of a material that is flexible, but does not stretch substantially in a radial or longitudinal direction. Coupling 2210 may be made of a polyurethane elastomer such as PELLETHANE, or any other suitable material.

Ring 2240 may be coupled to proximal portion 2211 of coupling 2210. Ring 2240 may be a thickened portion of coupling 2210, or a separate structure operably attached to coupling 2210. Ring 2240 may be sufficiently flexible to deform inwardly, but sufficiently rigid to spring back to its original shape. Ring 2240 is configured to interface with retainer 2140. Ring 2240 may have an interference fit with retainer 2140, or other form of attachment. Sleeve 2200 is thus coupled to cuff 2100 by ring 2240 and retainer 2140. Ring 2240 may deform when sleeve 2200 is pulled distally to allow sleeve 2200 some travel, provide some shock absorption, and more evenly distribute forces to tissue anchors. Sleeve 2200 can be exchanged for a new, second sleeve having the same or one, two, or more differing properties by inwardly deforming ring 2240 and removing sleeve 2200. Ring 2240 may be inwardly deformed using a drawstring 2241 threaded through drawstring holes 2215. Other properties of sleeves, cuffs, cuff-sleeve attachment interfaces, and sleeve exchange methods can be found, for example, in U.S. Pat. Pub. No. 2007/0198074 to Dann et al., and U.S. Pat. No. 8,070,743 to Kagan et al., each of which are hereby incorporated by reference in their entireties.

Tube 2250 includes a proximal portion 2251, a distal portion 2252, and a lumen 2253. Proximal portion 2251 of tube 2250 may be coupled to distal portion 2212 of coupling 2210 with an interference fit, heat bonded, and/or other suitable methods. Alternatively, tube 2250 may be formed integrally with coupling 2210. Tube 2250 may have a uniform width. Alternatively, tube 2250 may taper or change in width. Tube 2250 may allow food and liquids to bypass the stomach and/or part of the intestine. Tube 2250 may allow foods and liquids to be bypassed into the duodenum, jejunum, or other part of the intestine. In one embodiment, tube 2250 may have a length of approximately 80 cm to 450 cm, a diameter of approximately 15 mm to 25 mm, and/or a thickness of about 0.05 mm to about 0.5 mm, such as about 0.15 mm.

Tube 2250 may be made of a material that is floppy or flaccid, but does not stretch substantially in a radial direction. Thus, tube 2250 may be flexible and compliant inwardly to allow peristaltic forces to act on its contents, but will not balloon outwardly. Tube 2250 may also not stretch substantially in a longitudinal direction. Tube 2250 may be made of a polyurethane elastomer such as PELLETHANE, or any other suitable material. Tube 2250 may be impermeable or semi-permeable. Tube 2250 may allow nutrients and medications inside tube 2250 to pass outward. Alternatively or in addition, tube 2250 may allow digestive juices and hormones outside tube 2250 to pass inward. Tube 2250 or portions of tube 2250 may be biodegradable. Tube 2250 with a plurality of biodegradable portions may be configured such that each portion degrades at a different rate.

Tube 2250 may include one or more coatings to resist calcification, deliver medications, provide lubriciousness, and/or provide other desired properties. These coatings may include parylene, polyvinylpyrrolidone (PVP), and/or other suitable materials. Tube 2250 may include an electrical stimulation element to resist calcification and promote motility and satiety. Various electrical stimulation elements that can be utilized or modified for use with the systems and methods disclosed herein are described, for example, in U.S. Pat. No. 7,881,797 to Griffin et al., which is hereby incorporated by reference in its entirety. Tube 2250 may be made up of one or more sections which may be coupled or uncoupled to adjust a length of tube 2250. Tube 2250 may include one, two, or more additional lumens interior to, exterior to, or within walls of tube 2250 for delivery of medications, access for imaging devices for visual monitoring, and access for diagnostic sampling. Tube 2250 may have additional lumens which open at different points along the length of tube 2250 for targeted delivery or access.

Tube 2250 may include a radiopaque marker 2254. Radiopaque marker 2254 may be one or more longitudinal stripes which run along all or part of the length of tube 2250. Radiopaque marker 2254 may be configured to help prevent or reduce kinking and twisting of tube 2250. For example, radiopaque marker 2254 may be thicker and/or wider toward proximal portion 2251 of tube 2250, where kinking and twisting may be more pronounced. Alternatively, radiopaque marker 2254 may be a helical stripe, circumferential bands, or other suitable configuration. Radiopaque marker 2254 may be coupled to an inside surface of tube 2250 to help maintain at least some patency of lumen 2253 and prevent lumen 2253 from closing completely when tube 2250 is kinked or twisted. Alternatively, radiopaque marker 2254 may be coupled to an outside surface of tube 2250. Various embodiments, features, materials and parameters of cuffs, sleeves, anchors, and other components that can be used or modified for use with those disclosed herein are described, for example, in the following patents and publications, each of which are incorporated by reference in their entireties: U.S. Pat. Pub. No. 2007/0198074 to Dann et al., U.S. Pat. No. 8,070,743 to Kagan et al., U.S. Pat. Pub. No. 2009/0149871 to Kagan et al., U.S. Pat. Pub. No. 2004/0092892 to Kagan et al., U.S. Pat. Pub. No. 2006/0155375 to Kagan et al., U.S. Pat. Pub. No. 2006/0015125 to Swain, U.S. Pat. Pub. No. 2006/0020254 to von Hoffmann, U.S. Pat. No. 8,118,774 to Dann et al., U.S. Pat. Pub. No. 2009/0012553 to Swain et al., U.S. Pat. Pub. No. 2009/0012544 to Thompson et al., and U.S. Pat. Pub. No. 2009/0012541 to Dahl et al.

Tube 2250 may include one, two, three, or more tails 2255 at distal portion 2252. Tails 2255 may be folded over each other and cinched with a grasping element, such as a loop snare, to seal distal portion 2255 of tube 2250 during deployment of sleeve 2200. Tails 2255 may be as described, for example, in U.S. Pat. No. 8,118,774 to Dann et al., which is hereby incorporated by reference in its entirety.

Halo 2260 may be coupled to proximal portion 2211 of coupling 2210 by one or more standoffs 2261. Standoffs 2261 may be coupled to proximal portion 2211 of coupling 2210 using an adhesive or other suitable methods. Halo 2260 may be made of suture or other suitable material. Halo 2260 is configured to be coupled to hooks 2160. Halo 2260 and hooks 2160 may provide a primary or backup coupling between sleeve 2200 and cuff 2100. Halo 2260 and hooks 2160 are configured to keep sleeve 2200 coupled to cuff 2100 if the coupling between retainer 2140 and ring 2240 should fail. Halo 2260 may be cut between standoffs 2261 to release sleeve 2200 for removal or exchange. Distal portion 2112 of liner 2110 may be enlarged in diameter or otherwise configured to accommodate halo 2260 and standoffs 2261.

Figure 3A:
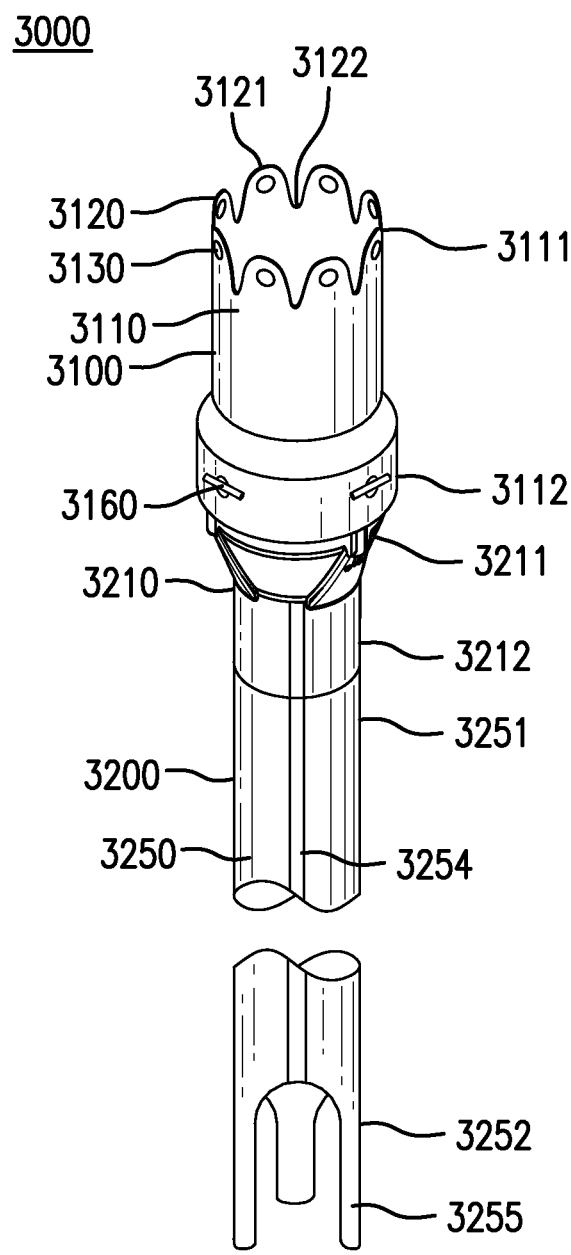
FIGS. 3A-3C show yet another embodiment of a gastrointestinal bypass device 3000.
Figure 3B:
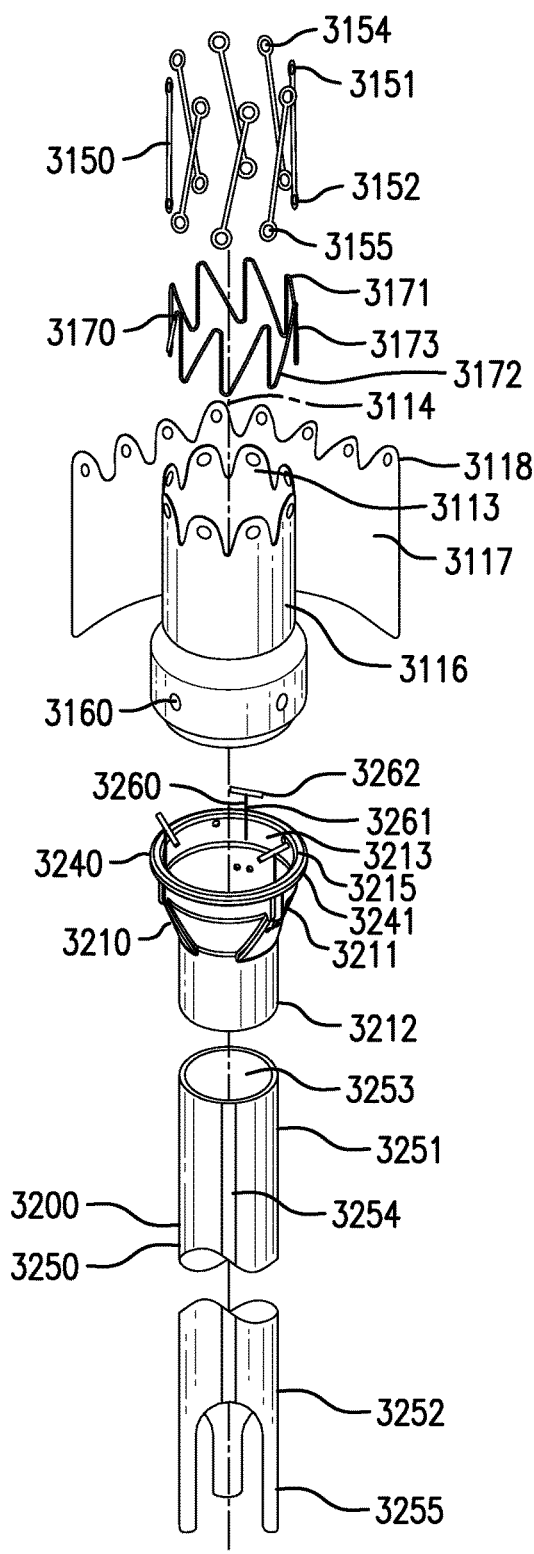
Figure 3C:
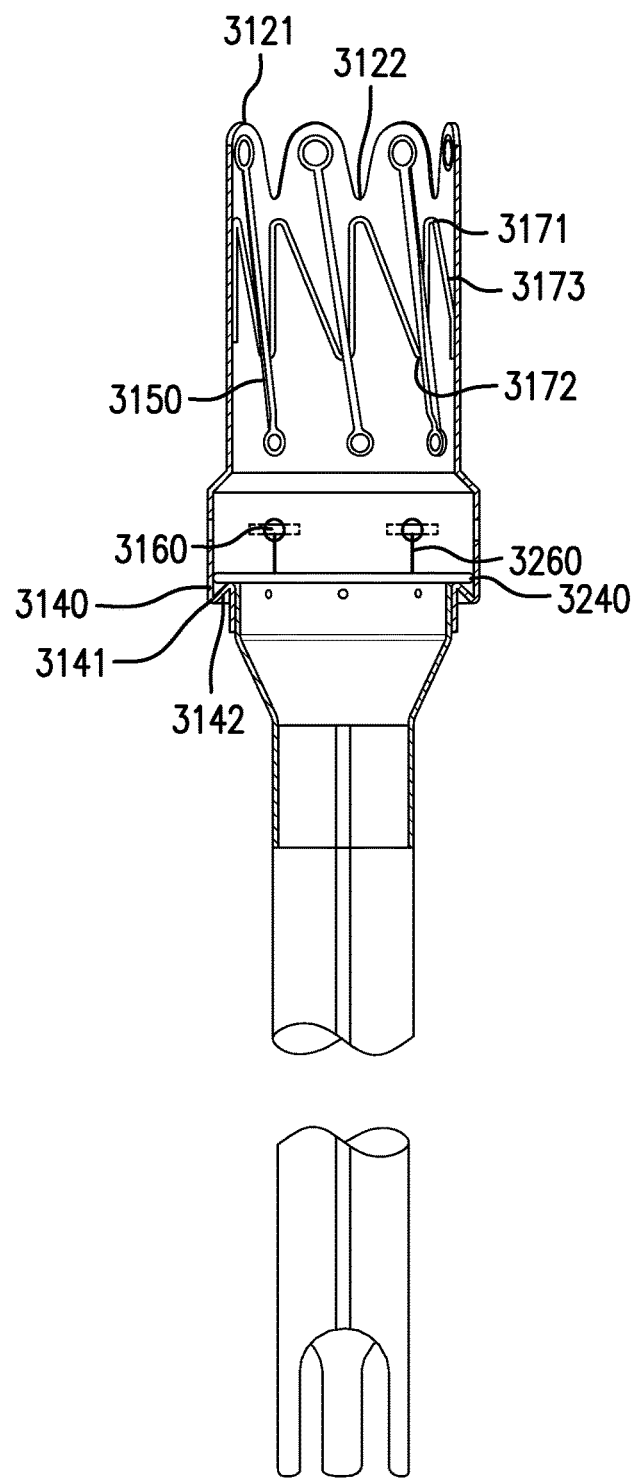
Figure 3D:
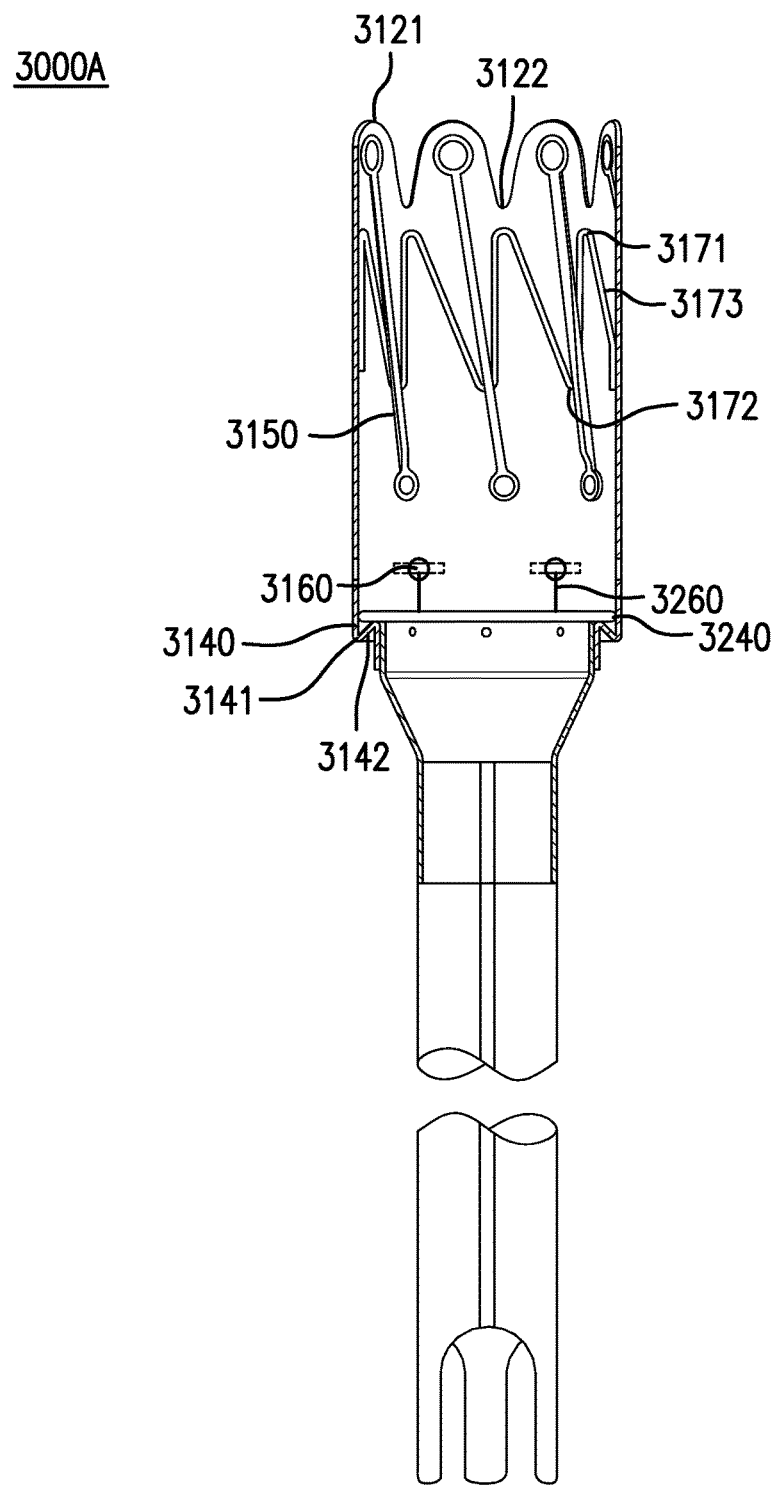
FIG. 3D shows still another embodiment of a gastrointestinal bypass device 3000A.
Figure 3E:
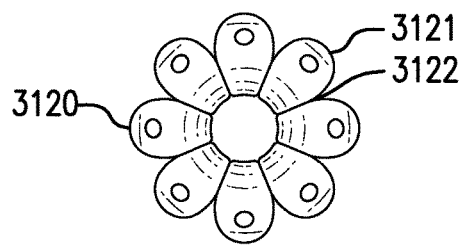
FIGS. 3E-3F show top views of cuff 3100 in an open and a closed position.
Figure 3F:
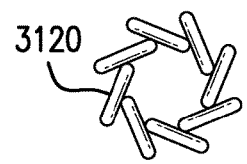

FIGS. 3A-3C show yet another embodiment of a gastrointestinal bypass device 3000. FIG. 3A shows a perspective view of gastrointestinal bypass device 3000. FIG. 3B shows an exploded view of gastrointestinal bypass device 3000. FIG. 3C shows a cross-sectional view of gastrointestinal bypass device 3000. FIG. 3D shows still another embodiment of a gastrointestinal bypass device 3000A. FIGS. 3E-3F show top views of cuff 3100 in an open and a closed position. FIGS. 3G-3H show enlarged views of strut 3150.

Figure 3I:
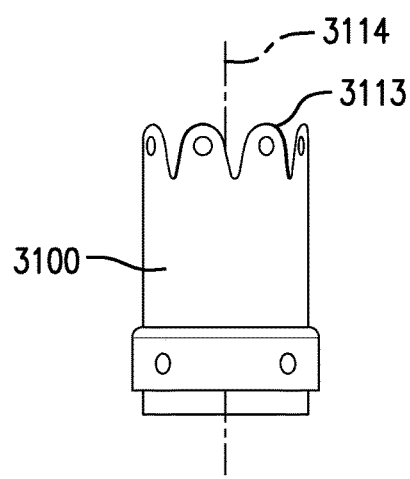
FIGS. 3I-3J show side views of cuff 3100 normally and subjected to a retrograde force.
Figure 3J:
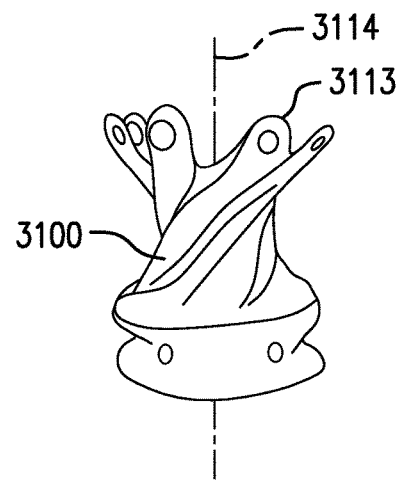
Figure 3G:
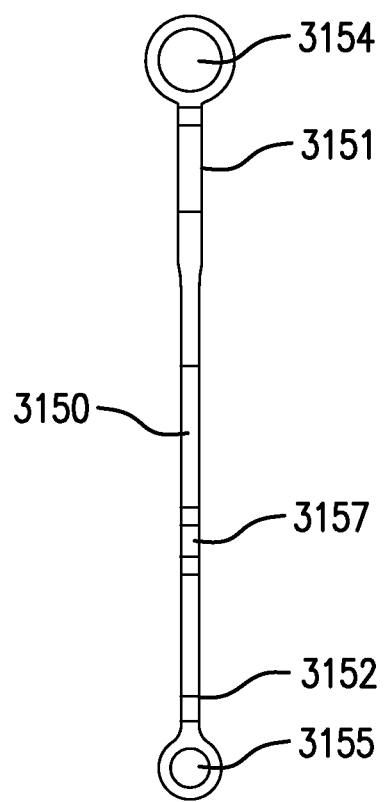
FIGS. 3G-3H show enlarged views of strut 3150.
Figure 3H:
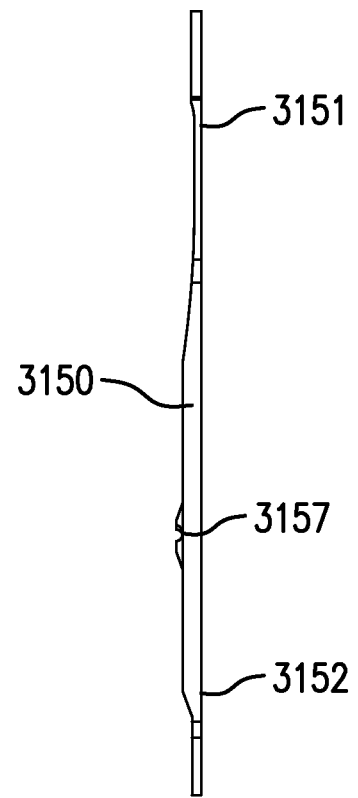
Figure 3K:
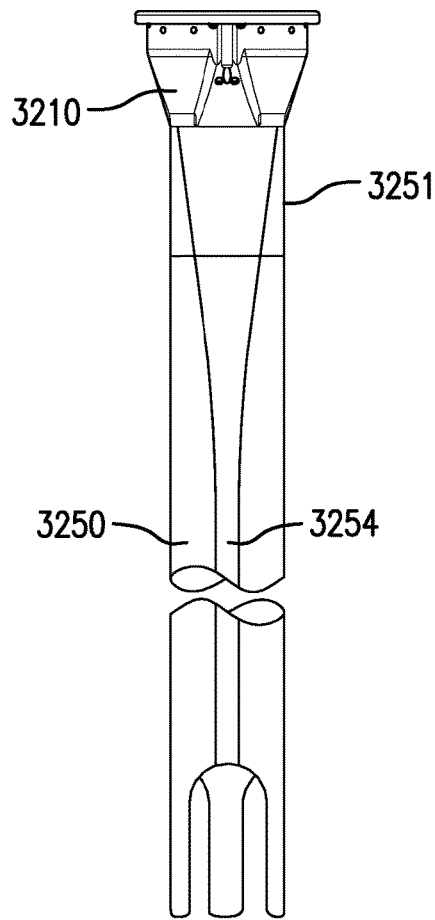
FIGS. 3K-3L show other embodiments of sleeve 3200.
Figure 3L:
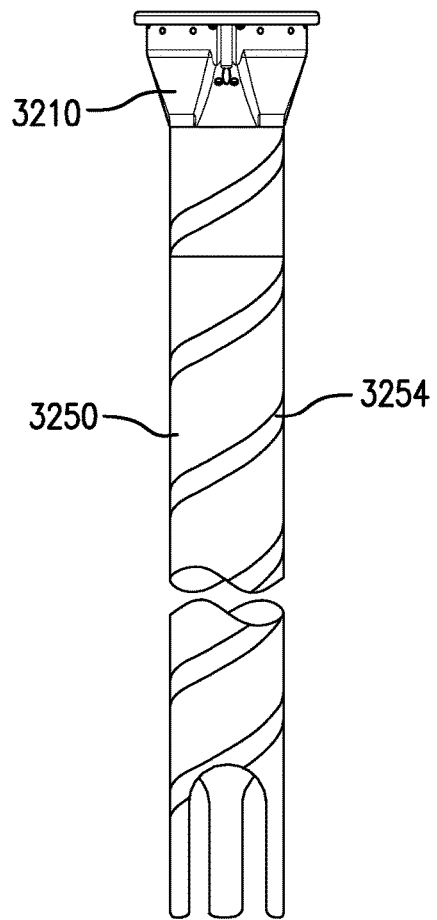

FIGS. 3I-3J show side views of cuff 3100 normally and subjected to a retrograde force. FIGS. 3K-3L show other embodiments of sleeve 3200.

Gastrointestinal bypass device 3000 may include a gastrointestinal cuff 3100 and a gastrointestinal sleeve 3200.

Cuff 3100 may be configured to be attached in the esophagus. Cuff 3100 may be attached at or near the gastroesophageal junction. Alternatively, cuff 3100 may be attached proximal to the gastroesophageal junction, in the proximal stomach, or at some other location. For example, cuff 3100 may be attached within about 3 cm, 2.5 cm, 2 cm, 1.5 cm, 1 cm, 0.5 cm, above, below, or at the GEJ or squamocolumnar junction (SCJ or Z-line). As another example, cuff 1100 may be attached up to 5 cm above the diaphragm. Some non-limiting locations for attachment can be found, for example, in U.S. Pat. Pub. No. 2007/0198174 to Dann et al., which is hereby incorporated by reference in its entirety (e.g., at paras. [0131] to [0147]). Cuff 3100 may be sufficiently flexible to expand and collapse to conform with the inside of the esophagus. Cuff 3100 directs food and liquids into sleeve 3200, and provides a structure to which sleeve 3200 may be attached. Cuff 3100 may be attached using tissue anchors.

Cuff 3100 may include a liner 3110, an edge with one, two, or more projections, e.g., a scalloped edge 3120, a plurality of anchor holes 3130, a retainer 3140, a plurality of struts 3150, one or more attachment openings 3160, and a scaffold 3170.

Liner 3110 may include a proximal portion 3111, a distal portion 3112, a lumen 3113, and a longitudinal axis 3114. Liner 3110 may be tubular and may have a uniform width. Alternatively, liner 3110 may taper or change in width. Liner 3110 may be made of material that is flexible. This flexibility allows the attachment area, such as the lower esophageal sphincter, to open and close substantially normally. Liner 3110 may be made of a material that is thin, allowing it to collapse into a smaller profile. This smaller profile allows the attachment area, such as the lower esophageal sphincter, to close substantially normally, and also helps liner 3110 to be collapsed for delivery. Liner 3110 may include an inner layer 3116 and an outer layer 3117. Alternatively, liner 3110 may include a single layer of material, or any number of layers. Inner layer 3116 and outer layer 3117 may be sealed at proximal portion 3111 with an edge seal 3118. Edge seal 3118 may be silicone or other suitable material. Edge seal 3118 may be radiopaque. Alternatively, inner layer 3116 and outer layer 3117 may be formed from a single layer of material folded over Inner layer 3116 and outer layer 3117 may be at least partially coupled together by sutures, thermal bonding, ultrasonic or laser welding, or other ways. Liner 3110 may be at least semi-permeable to liquids and/or solids. This semi-permeability may allow some food to reach the stomach, and may help the stomach maintain some residual functionality. This semi-permeability may allow medications to reach the stomach. Liner 3110 may be made of DACRON or any other suitable material. In one embodiment, liner 3110 may have a length of approximately 20 mm to 80 mm.

Scalloped edge 3120 may include a plurality of peaks 3121 and valleys 3122 formed at the edge of proximal portion 3111 of liner 3110. Peaks 3121 and valleys 3122 may be of uniform shape and size. Alternatively, peaks 3121 and valleys 3122 may be of varying shapes and sizes. Scalloped edge 3120 allows peaks 3121 to open wider than the rest of liner 3110, as shown in FIG. 3E. This enhances conformance of scalloped edge 3120 to an inside of the esophagus and reduces the amount of food and liquids which pass outside of scalloped edge 3120 and into the stomach (and thus outside of the cuff and sleeve). Reducing the amount of food or liquid that passes outside of the cuff and sleeve can in some cases advantageously improve clinical endpoints (e.g., improved weight loss, improved glycemic, lipid profile, blood pressure, etc.). Valleys 3122 may include a webbing which may be thinner than liner 3110. Scalloped edge 3120 reduces bunching of liner 3110 when the esophagus is closed, and reduces the profile of liner 3110 when the esophagus is closed, as shown in FIG. 3F.

A coupling mechanism, e.g., anchor holes 3130 may be formed in the peaks 3121 of scalloped edge 3120. Anchor holes 3130 are configured to receive tissue anchors. Anchor holes 3130 may be marked with a contrasting color, radiopaque marker, or other means to aid visualization. Anchor holes 3130 may be marked with stitching, ink, or other suitable marking Anchor holes 3130 may be used as a placement template for tissue anchors. Anchor holes 3130 may be evenly spaced about a circumference of liner 3110. Evenly spaced anchor holes 3130 may help to distribute forces among the tissue anchors, prevent concentration of forces in a small number of tissue anchors, and enhance conformance of liner 3110 to an inside (e.g., luminal wall) of the esophagus. Alternatively, anchor holes 3130 may be spaced in any manner about a circumference of liner 3110. Anchor holes 3130 may be substantially coplanar. Anchor holes 3130 may be arranged in a plane substantially perpendicular to longitudinal axis 3114, or angled to longitudinal axis 3114. A substantially coplanar arrangement may help to prevent concentration of forces in a small number of tissue anchors. Alternatively, anchor holes 3130 may be arranged in a staggered fashion.

Retainer 3140 may be coupled to distal portion 3112 of liner 3110. Retainer 3140 may be collapsible radially inwardly but not expandable radially outwardly. Retainer 3140 may be a circumferential channel formed in distal portion 3112 of liner 3110 by one or more folds 3141. Folds 3141 may be secured by a suture 3142, adhesive, or other means. Folds 3141 may be made more rigid by applying a stiffening substance to distal portion 3112 and/or folds 3141. The stiffening substance may be silicone or other suitable substance. Alternatively, retainer 3140 may be made of plastic or other suitable material, and coupled to distal portion 3112 of liner 3110.

Struts 3150 each include a proximal portion 3151 and a distal portion 3152. Struts 3150 may be elongate and substantially straight. Alternatively, struts 3150 may be curved or any other suitable shape. Struts 3150 may be coupled to liner 3110 between layers of liner 3110. Alternatively, struts 3150 may be coupled to an inner surface or an outer surface of liner 3110. Struts 3150 may be coupled to liner 3110 at an angle of 1 to 30 degrees or more with respect to longitudinal axis 3114 of liner 3110. Alternatively, struts 3150 may be coupled to liner 3110 longitudinally without an angle. Struts 3150 may include a first attachment element, e.g., an anchor eyelet 3154 at proximal portion 3151. Struts 3150 may include a second attachment element, e.g., a suture eyelet 3155 at distal portion 3152. Anchor eyelets 3154 may be aligned with anchor holes 3130 of liner 3110 to reinforce anchor holes 3130 of liner 3110 and prevent tissue anchors from pulling through. Struts 3150 may be coupled to liner 3110 with pockets formed by stitching together layers of liner 3110, and stitching through suture eyelets 3155. Alternatively, struts 3150 may be coupled to liner 3110 with sutures, adhesives, thermal bonding, ultrasonic or laser welding, or other suitable ways. Struts 3150 may have a uniform cross-section. Alternatively, struts 3150 may have a non-uniform cross-section which varies wider, narrower, thicker, and/or thinner. For example, struts 3150 may have a proximal portion 3151 and/or a distal portion 3152 which are thinner and/or wider, as shown in FIGS. 3G-3H. This varying cross-section allows proximal portion 3151 and/or distal portion 3152 to be more flexible. Struts 3150 may include a notch 3157. Struts 3150 may be made of a plastic such as PEEK, a metal, or any other suitable material.

Struts 3150 may reduce longitudinal stretching of liner 3110. Prograde forces such as peristaltic forces at distal portion 3112 of liner 3110 are transferred by struts 3150 to anchor eyelets 3154 and tissue anchors, to advantageously redistribute forces and minimize focal wear or failure points. Struts 3150 may also prevent inversion of liner 3110. Retrograde forces such as vomiting or retching forces at distal portion 3112 of liner 3110 cause liner 3110 and angled struts 3150 to twist or corkscrew about longitudinal axis 3114 and prevents inversion of liner 3110, as shown in FIGS. 3I-3J, helping to maintain liner 3110 in proper implanted position. This twisting or corkscrewing may also at least partially close lumen 3113 of liner 3110.

Attachment openings 3160 may be formed at distal portion 3112 of liner 3110. Attachment openings 3160 may be marked with a contrasting color to aid visualization. Attachment openings 3160 may be marked with stitching, ink, or other suitable marking.

Scaffold 3170 may be coupled to liner 3110 between layers of liner. Alternatively, scaffold may be coupled to an inner surface or an outer surface of liner 3110. Scaffold 3170 may be coupled to liner 3110 with sutures, adhesives, or other suitable ways. Scaffold 3170 may have any desired wall pattern, and in some embodiments resemble a sawtooth wave, sine wave, square wave, triangle wave, or other wave. Scaffold 3170 may include a plurality of proximal segments 3171 and a plurality of distal segments 3172 connected by a plurality of connecting segments 3173. Alternatively, scaffold 3170 may be a mesh, ring, or other suitable device. Scaffold 3170 may be coupled to struts 3150, or formed integrally with struts 3150. Scaffold 3170 may cross each strut 3150 through notch 3157.

Scaffold 3170 provides an outward bias to enhance conformance of liner 3110 to the luminal wall of the esophagus. This outward bias may be large enough to open liner 3110 when the esophagus opens, but not so large as to prevent the esophagus from closing. Scaffold 3170 is not necessarily meant to hold cuff 3100 in the esophagus. Scaffold 3170 may have a geometry, such as length and thickness, selected to create a desired amount of outward bias. Scaffold 3170 may be made of a material selected to create a desired amount of outward bias. Scaffold 3170 may be made of plastic such as PEEK, metal, or any other suitable material. Proximal segments 3171 may be placed at or near valleys 3122. This placement positions outward bias at valleys 3122. Any portion of scaffold 3170 may be placed across struts 3150. The placement of scaffold 3170 across struts 3150 may be selected to create a desired amount of outward bias. For example, distal segments 3172 may be placed across struts 3150. This placement provides a pivot point for connecting segments 3173 of scaffold 3170. This placement may also fold or rotate peaks 3121 when liner 3110 closes, resulting in a smaller closed profile, as shown in FIGS. 3E-3F.

Sleeve 3200 is configured to be coupled to cuff 3100, either in an integrally formed or removably coupled manner. Sleeve 3200 directs food and liquids into the intestine. Sleeve 3200 may include a coupling 3210, a ring 3240, a tube 3250, and one or more attachment elements 3260.

Coupling 3210 directs food and liquids from cuff 3100 to tube 3250. Coupling 3210 includes a proximal portion 3211, a distal portion 3212, and a lumen 3213. Drawstring holes 3215 may be formed at or near proximal portion 3211. Proximal portion 3211 may have a width that is the same as or substantially the same as liner 3110, or in some embodiments taper down in width to restrict the flow of food and liquids through coupling 3210, which may help to create a feeling of fullness. Distal portion 3212 may have a uniform width. Alternatively, proximal portion 3211 and distal portion 3212 may have a uniform width. Coupling 3210 may be made of a material that is flexible, but does not stretch substantially in a radial or longitudinal direction. Coupling 3210 may be made of a polyurethane elastomer such as PELLETHANE, or any other suitable material.

Ring 3240 may be coupled to proximal portion 3211 of coupling 3210. Ring 3240 may be a thickened portion of coupling 3210, or a separate structure operably attached to coupling 3210. Ring 3240 may be sufficiently flexible to deform inwardly, but sufficiently rigid to spring back to its original shape. Ring 3240 is configured to interface with retainer 3140. Ring 3240 may have an interference fit with retainer 3140, or other form of attachment. Sleeve 3200 is thus coupled to cuff 3100 by ring 3240 and retainer 3140. Ring 3240 may deform when sleeve 3200 is pulled distally to allow sleeve 3200 some travel, provide some shock absorption, and more evenly distribute forces to tissue anchors. Sleeve 3200 can be exchanged for a new, second sleeve having the same or one, two, or more differing properties by inwardly deforming ring 3240 and removing sleeve 3200. Ring 3240 may be inwardly deformed using a drawstring 3241 threaded through drawstring holes 3215. Other properties of sleeves, cuffs, cuff-sleeve attachment interfaces, and sleeve exchange methods can be found, for example, in U.S. Pat. Pub. No. 2007/0198074 to Dann et al., and U.S. Pat. No. 8,070,743 to Kagan et al., each of which are hereby incorporated by reference in their entireties.

Tube 3250 includes a proximal portion 3251, a distal portion 3252, and a lumen 3253. Proximal portion 3251 of tube 3250 may be coupled to distal portion 3212 of coupling 3210 with an interference fit, heat bonded, and/or other suitable methods. Alternatively, tube 3250 may be formed integrally with coupling 3210. Tube 3250 may have a uniform width. Alternatively, tube 3250 may taper or change in width. Tube 3250 may allow food and liquids to bypass the stomach and/or part of the intestine. Tube 3250 may allow foods and liquids to be bypassed into the duodenum, jejunum, or other part of the intestine. In one embodiment, tube 3250 may have a length of approximately 80 cm to 450 cm, a diameter of approximately 15 mm to 25 mm, and/or a thickness of about 0.05 mm to about 0.5 mm, such as about 0.15 mm.

Tube 3250 may be made of a material that is floppy or flaccid, but does not stretch substantially in a radial direction. Thus, tube 3250 may be flexible and compliant inwardly to allow peristaltic forces to act on its contents, but will not balloon outwardly. Tube 3250 may also not stretch substantially in a longitudinal direction. Tube 3250 may be made of a polyurethane elastomer such as PELLETHANE, or any other suitable material. Tube 3250 may be impermeable or semi-permeable. Tube 3250 may allow nutrients and medications inside tube 3250 to pass outward. Alternatively or in addition, tube 3250 may allow digestive juices and hormones outside tube 3250 to pass inward. Tube 3250 or portions of tube 3250 may be biodegradable. Tube 3250 with a plurality of biodegradable portions may be configured such that each portion degrades at a different rate.

Tube 3250 may include one or more coatings to resist calcification, deliver medications, provide lubriciousness, and/or provide other desired properties. These coatings may include parylene, polyvinylpyrrolidone (PVP), and/or other suitable materials. Tube 3250 may include an electrical stimulation element to resist calcification and promote motility and satiety. Various electrical stimulation elements that can be utilized or modified for use with the systems and methods disclosed herein are described, for example, in U.S. Pat. No. 7,881,797 to Griffin et al., which is hereby incorporated by reference in its entirety. Tube 3250 may be made up of one or more sections which may be coupled or uncoupled to adjust a length of tube 3250. Tube 3250 may include one, two, or more additional lumens interior to, exterior to, or within walls of tube 3250 for delivery of medications, access for imaging devices for visual monitoring, and access for diagnostic sampling. Tube 3250 may have additional lumens which open at different points along the length of tube 3250 for targeted delivery or access.

Tube 3250 may include a radiopaque marker 3254. Radiopaque marker 3254 may be one or more longitudinal stripes which run along all or part of the length of tube 3250. Radiopaque marker 3254 may be configured to help prevent or reduce kinking and twisting of tube 3250. For example, radiopaque marker 3254 may be thicker and/or wider toward proximal portion 3251 of tube 3250 as shown in FIG. 3K, where kinking and twisting may be more pronounced. Alternatively, radiopaque marker 3254 may be a helical stripe as shown in FIG. 3L, circumferential bands, or other suitable configuration. Radiopaque marker 3254 may be coupled to an inside surface of tube 3250 to help maintain at least some patency of lumen 3253 and prevent lumen 3253 from closing completely when tube 3250 is kinked or twisted. Alternatively, radiopaque marker 3254 may be coupled to an outside surface of tube 3250. Various embodiments, features, materials and parameters of cuffs, sleeves, anchors, and other components that can be used or modified for use with those disclosed herein are described, for example, in the following patents and publications, each of which are incorporated by reference in their entireties: U.S. Pat. Pub. No. 2007/0198074 to Dann et al., U.S. Pat. No. 8,070,743 to Kagan et al., U.S. Pat. Pub. No. 2009/0149871 to Kagan et al., U.S. Pat. Pub. No. 2004/0092892 to Kagan et al., U.S. Pat. Pub. No. 2006/0155375 to Kagan et al., U.S. Pat. Pub. No. 2006/0015125 to Swain, U.S. Pat. Pub. No. 2006/0020254 to von Hoffmann, U.S. Pat. No. 8,118,774 to Dann et al., U.S. Pat. Pub. No. 2009/0012553 to Swain et al., U.S. Pat. Pub. No. 2009/0012544 to Thompson et al., and U.S. Pat. Pub. No. 2009/0012541 to Dahl et al.

Tube 3250 may include one, two, three, or more tails 3255 at distal portion 3252. Tails 3255 may be folded over each other and cinched with a grasping element, such as a loop snare, to seal distal portion 3255 of tube 3250 during deployment of sleeve 3200. Tails 3255 may be as described, for example, in U.S. Pat. No. 8,118,774 to Dann et al., which is hereby incorporated by reference in its entirety.

Attachment elements 3260 are configured to be coupled to attachment openings 3160. Attachment elements 3260 and attachment openings 3160 may provide a first, e.g., a primary, or second, e.g., a backup, coupling between sleeve 3200 and cuff 3100. Attachment elements 3260 and attachment openings 3160 may be configured to keep sleeve 3200 coupled to cuff 3100 if the coupling between retainer 3140 and ring 3240 should fail.

Figure 20A:
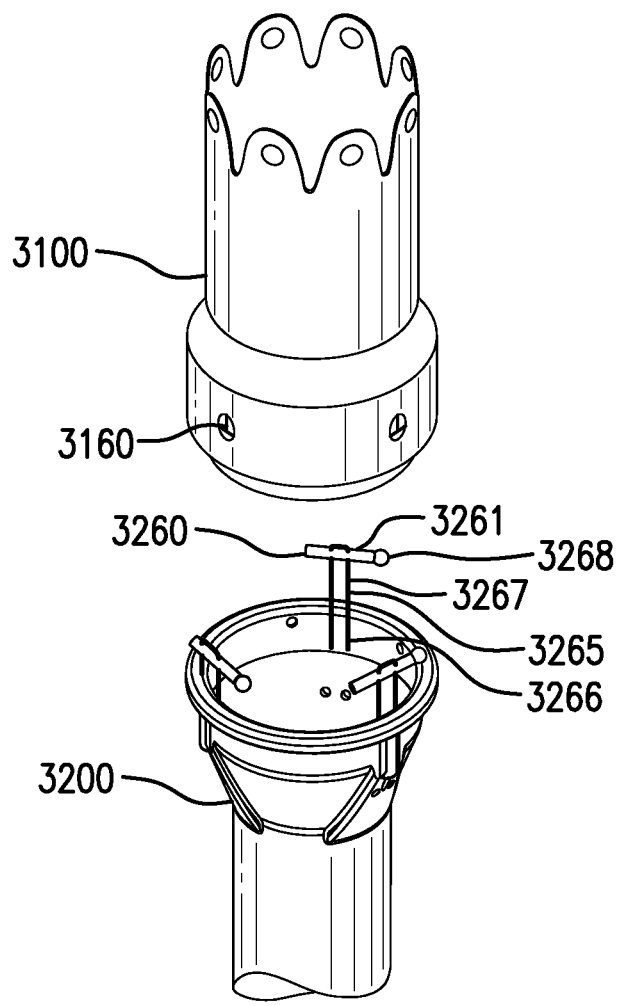
FIG. 20A shows one embodiment of gastrointestinal cuff with one or more attachment openings 3160 and a gastrointestinal sleeve with one or more attachment elements 3260.
Figure 20B:
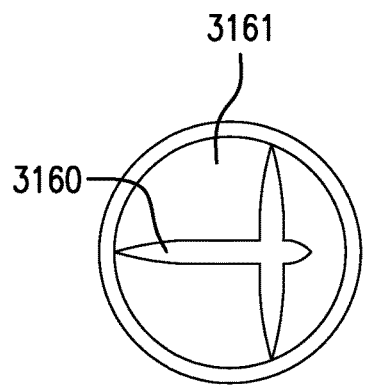
FIGS. 20B-20E show various embodiments of attachment openings 3160.
Figure 20C:
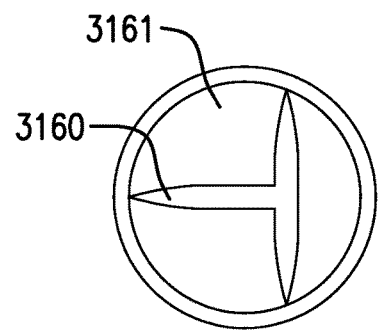
Figure 20D:
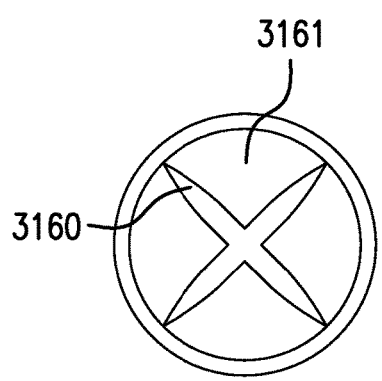
Figure 20E:
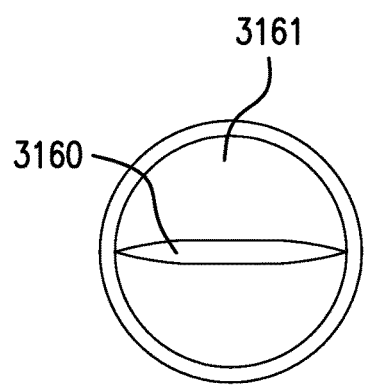
Figure 20F:
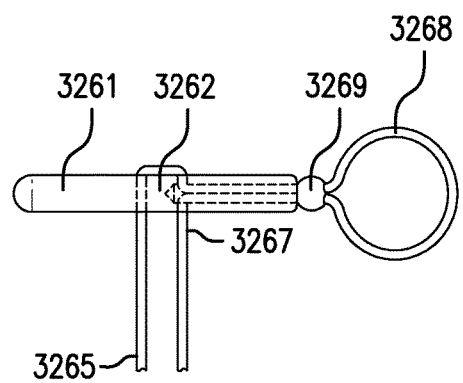
Figure 20H:
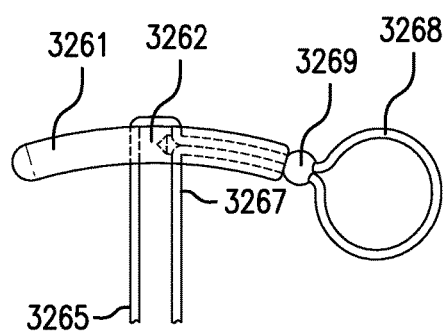
Figure 20G:
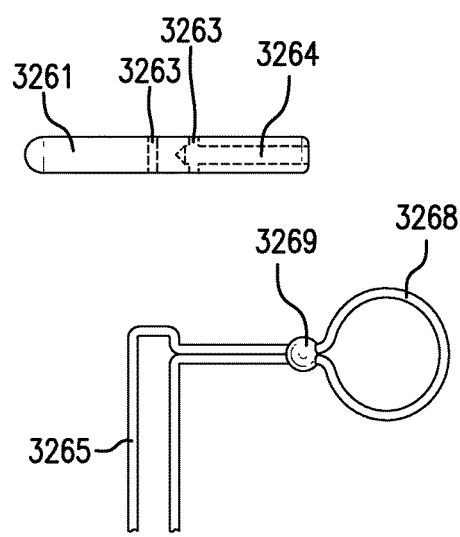
Figure 20I:
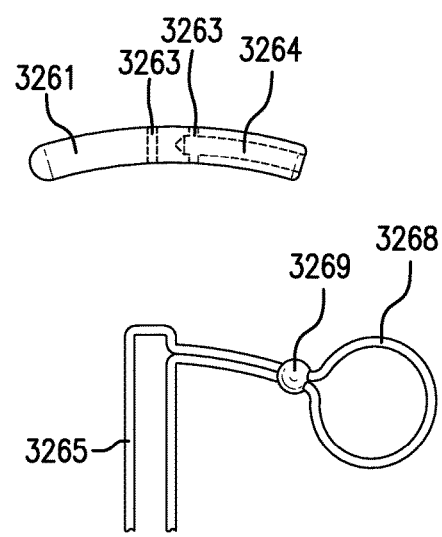

FIG. 20A shows one embodiment of cuff 3100 with one or more attachment openings 3160 and sleeve 3200 with one or more attachment elements 3260. FIGS. 20B-20E show various embodiments of attachment openings 3160. FIGS. 20E-20G, 20H-20I, and 20J-20K show enlarged and exploded views of various embodiments of an attachment element 3260.

Attachment openings 3160 may be round, oval, or any other suitable shape. Attachment openings 3160 may be deformable or substantially rigid. Attachment openings 3160 may include one or more flaps 3161 that cover attachment openings 3160 which are not in use to reduce leakage through attachment openings 3160. As shown in FIGS. 20B-20E, flaps 3161 may be arranged in a t-, T-, X-, or slit-like configuration, respectively, or any other suitable configuration. Flaps 3161 may be flexible to allow attachment element 3260 to pass through. Flaps 3161 may be made of a similar or different material as the rest of liner 3110. For example, flaps 3161 may be made of silicone or other suitable material.

Attachment element 3260 may include an elongate member 3261, a tension element 3265, and at least one grasping aid 3268. The number of attachment elements 3260 may be equal or unequal to the number of attachment openings 3160. In other applications, attachment element 3260 may be used to couple any device through an attachment opening 3160 formed in a wall of a mating device or tissue wall by deploying attachment element 3260 on an opposite side of the wall.

Elongate member 3261 includes a central portion 3262. Elongate member 3261 is configured to be passed longitudinally through attachment opening 3160 from the inside of liner 3110, and deployed transversely on the outside of liner 3110. Elongate member 3261 is of a length or other physical dimensions which will not be pulled through attachment opening 3160 after being deployed. Elongate member 3261 may be straight, curved, or any other suitable shape. Elongate member 3261 may include one or more holes 3263 through which tension element 3265 may be coupled. Elongate member 3261 may include one or more holes 3264 through which grasping aid 3268 may be coupled. One or more holes 3264 may be in communication with one or more holes 3263, as shown in FIGS. 20E-20G and 20H-20I. Elongate member 3261 may be at least partially radiopaque to aid in placement and monitoring.

Tension element 3265 includes a proximal portion 3266 and a distal portion 3267. Proximal portion 3266 may be coupled to sleeve 3200. Distal portion 3267 may be flexibly coupled to central portion 3262 of elongate member 3261. Tension element 3265 may be a loop of suture passed through holes 3263 in elongate member 3263 and holes in sleeve 3200 and secured with one or more knots. Alternatively, tension element 3265 may be made of a length of suture, or any other suitable material. Alternatively, tension element 3265 may be a tube, stick, or other suitable element. Tension element 3265 may be substantially flexible or substantially rigid. Tension element 3265 may be stretchable to allow sleeve 3200 some travel, provide some shock absorption, and to more evenly distribute forces to tissue anchors. Tension element 3265 may be cut to release sleeve 3200 for removal or exchange.

Grasping aid 3268 may be grasped by a grasper, hook, or other suitable tool and advanced through attachment opening 3160 along with elongate member 3261 and distal portion 3267 of tension element 3265. Attachment opening 3160 may be sized or otherwise configured to allow the tool, elongate member 3261, and distal portion 3267 of tension element 3265 to pass through together. Grasping aid 3268 may be coupled to or near at least one end of elongate member 3261. Grasping aid 3268 may include a loop of suture or a length of suture. Alternatively, grasping aid 3268 may include a substantially rigid extension or stub flexibly or rigidly coupled to or near at least one end of elongate member 3261.

Figure 20J:
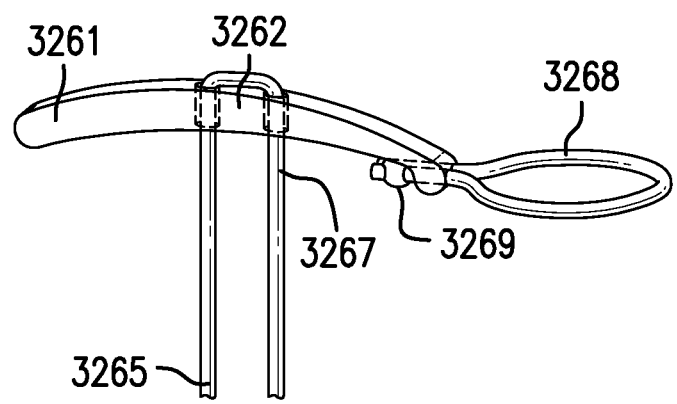
Figure 20K:
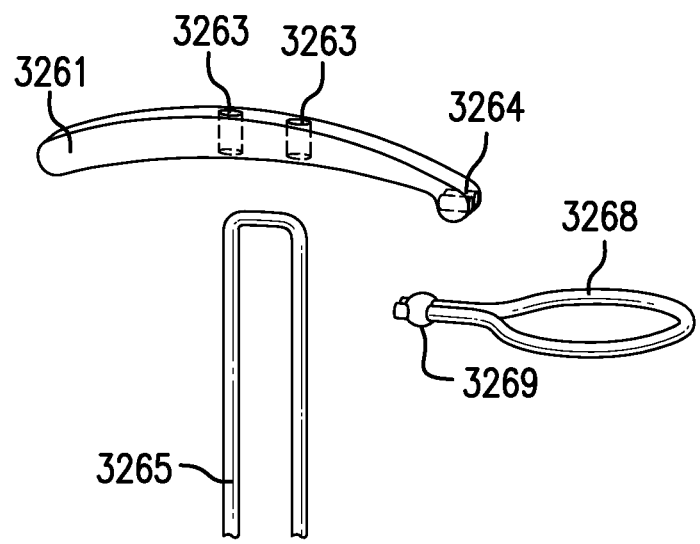

Tension element 3265 and grasping aid 3268 may be formed from a continuous piece of suture or other material which passes through holes 3263 and holes 3264 and is secured by one or more knots 3269, as shown in FIGS. 20E-20G and 20H-20I. Alternatively, tension element 3265 and grasping aid 3268 may be include separate pieces of suture, or similar or dissimilar materials, as shown in FIGS. 20J-20K. Grasping aid 3268 may be secured by one or more knots 3269.

FIGS. 21A-21F show one embodiment of a method for using attachment element 3260 to attach a device through an attachment opening 3160 formed in a wall.

FIG. 21A shows advancing a tool, in this embodiment a grasper G, from the working channel of an endoscope E.

FIG. 21B shows using the grasper G to grasp grasping aid 3268.

FIG. 21C shows advancing the grasper G toward attachment opening 3160 from the inside of liner 3110. Grasper G may include a working end that is pre-curved and/or steerable to aid in manipulating elongate member 3261 through attachment opening 3160.

FIG. 21D shows advancing the grasper G through attachment opening 3160 to pass grasping aid 3268 through attachment opening 3160 from the inside of liner 3110. Because grasping aid 3268 is coupled to or near an end of elongate member 3261 and pulls on or near the end of elongate member 3261, elongate member 3261 becomes aligned to pass longitudinally through attachment opening 3160. Because distal portion 3267 of tension element 3265 may be flexibly coupled to elongate member 3261, elongate member 3261 may move or rotate with respect to tension element 3265.

Figure 21E:
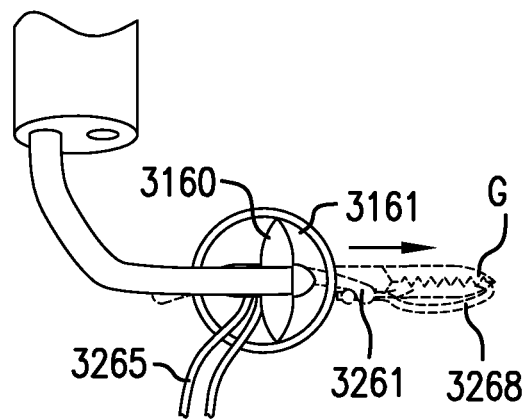

FIG. 21E shows continuing to advance the grasper G through attachment opening 3160 to pass elongate member 3261 longitudinally through attachment opening 3160. Also passed through attachment opening 3160 are the grasper G and the distal portion 3267 of tension element 3265.

Figure 21F:
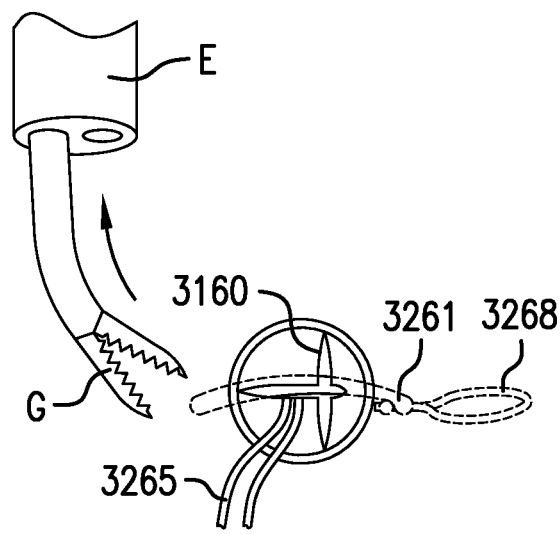

FIG. 21F shows releasing grasping aid 3268 to deploy elongate member 3261 transversely on the outside of liner 3110. Elongate member 3261 is passed through attachment opening 3160 completely. Releasing grasping aid 3268 generally causes elongate member 3261 to catch or deploy transversely on the outside of liner 3110. If elongate member 3261 passes back through attachment opening 3160, the grasper G may be used to grasp grasping aid 3268 or other part of elongate member 3261 and attempt deployment again.

One or more safety sutures may be used to provide a backup coupling between sleeve 3200 and cuff 3100. Safety sutures may be cut to release sleeve 3200 for removal or exchange.

Figure 4A:
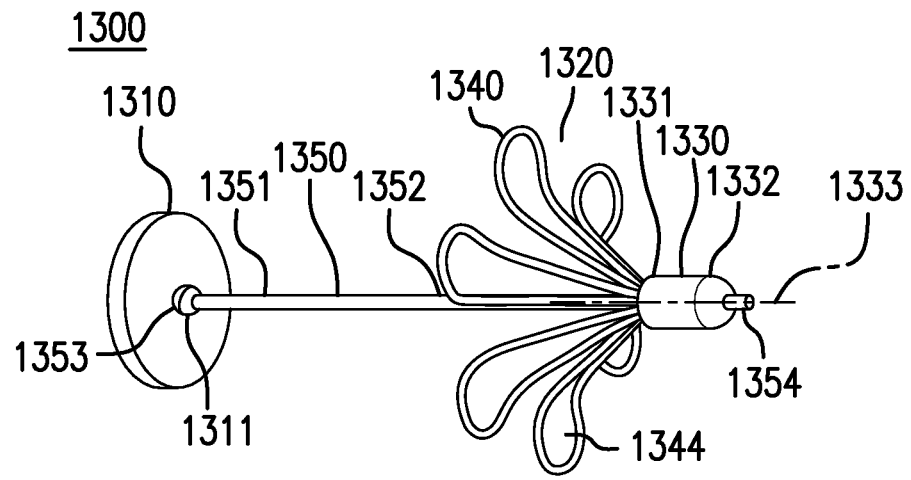
FIGS. 4A-4B show one embodiment of a tissue anchor 1300.
Figure 4B:
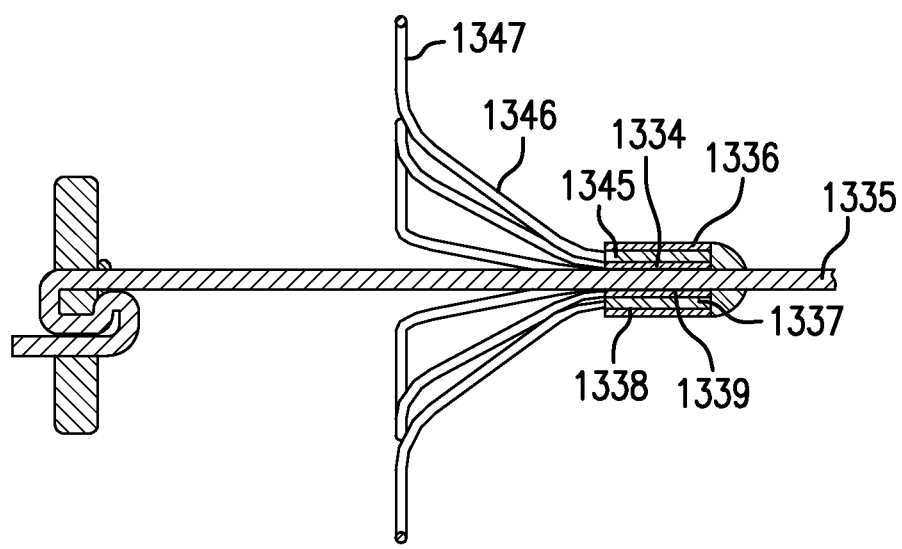

FIGS. 4A-4B show one embodiment of a tissue anchor 1300. FIG. 4A shows a perspective view of tissue anchor 1300. FIG. 4B shows a cross-sectional view of tissue anchor 1300.

Figure 4C:
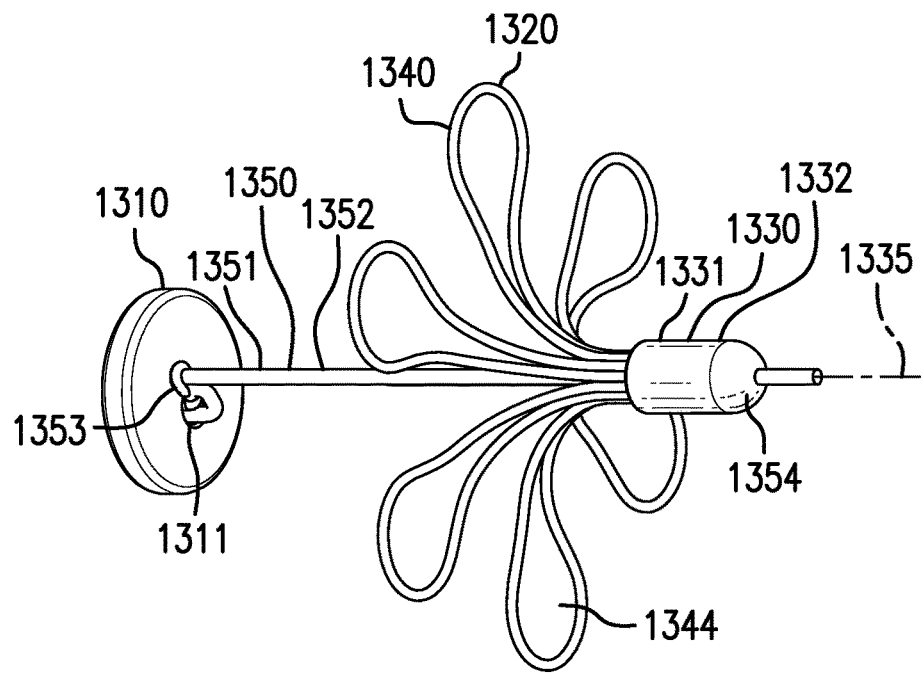
FIGS. 4C-4D show another embodiment of a tissue anchor 1300A.
Figure 4D:
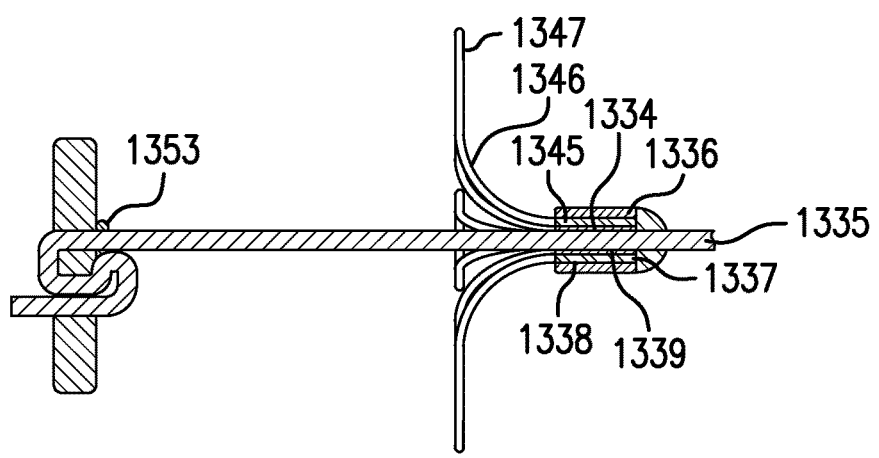

FIGS. 4C-4D show another embodiment of a tissue anchor 1300A. FIG. 4C shows a perspective view of tissue anchor 1300A. FIG. 4D shows a cross-sectional view of tissue anchor 1300A.

The cuffs and/or sleeves described above may be anchored, for example, using tissue anchors 1300 and tissue anchors 1300A, or any other suitable tissue anchor. Other tissue anchors or features of tissue anchors that may be used with systems and methods as described herein can be found, for example, in U.S. Pat. Pub. No. 2009/0012541 to Dahl et al., which is hereby incorporated by reference in its entirety.

Tissue anchor 1300 and tissue anchor 1300A are configured to pass through a tissue wall to retain a device. For example, tissue anchor 1300 and tissue anchor 1300A may be configured to pass through an anchor hole in a cuff and transmurally through the wall of the esophagus to retain a cuff in the esophagus.

Tissue anchor 1300 and tissue anchor 1300A each include a proximal retention element 1310, a distal retention element 1320, and a tension element 1350.

Proximal retention element 1310 is configured to be deployed on a proximal side of a tissue wall. Proximal retention element 1310 may be a button, a bar, or other suitable shape. In one embodiment, proximal retention element 1310 may be a button having a diameter of approximately 2 mm to 5 mm, and a thickness of approximately 0.25 mm to 1 mm. Proximal retention element 1310 may include one or more holes 1311. Proximal retention element 1310 may be at least partially radiopaque to aid in placement and monitoring.

Distal retention element 1320 is configured to be deployed on a distal side of a tissue wall. Distal retention element 1320 may include a hub 1330 and a plurality of petals 1340.

Hub 1330 includes a proximal end 1331, a distal end 1332, and a longitudinal axis 1333. Hub 1330 includes an inner tube 1334 having a central lumen 1335. Hub 1330 also includes an outer tube 1336. Inner tube 1334 and outer tube 1336 form an annular space 1337. Inner tube 1334 and outer tube 1336 may be substantially the same length, or be of different lengths Inner tube 1334 and outer tube 1336 may be made of a stainless steel or other suitable material.

Petals 1340 each include a proximal side 1341, a distal side 1342, an open area 1344, a hub portion 1345, an inclined portion 1346, and a tissue contact portion 1347. Hub portion 1345 is coupled to tissue contact portion 1347 by inclined portion 1346. Hub portion 1345 is at least partially positioned within annular space 1337. Hub portion 1345 may be coupled to inner tube 1334 and outer tube 1336 with an adhesive 1338, solder or weld joint, laser weld, compression fit, or other suitable ways. Adhesive 1338 may be a two-part epoxy or other suitable material or adhesive. In one embodiment, hub portion 1345 may have a length of approximately 0.5 mm to 2 mm. Inclined portion 1346 extends from proximal end 1331 of hub 1330. In one embodiment, inclined portion 1346 may be inclined at an angle of approximately 30 to 60 degrees with respect to longitudinal axis 1333. Alternatively, inclined portion 1346 may be inclined at a variable angle between 0 and 90 degrees with respect to longitudinal axis 1333. In one embodiment as shown in FIGS. 4A-4B, inclined portion 1346 may have a length of approximately 3 mm to 4 mm. In another embodiment as shown in FIGS. 4C-4D, inclined portion 1346 may have a length of approximately 2 mm to 3 mm.

Tissue contact portion 1347 is configured to contact a distal surface of a tissue wall. Tissue contact portion 1347 may be substantially flat, or it may be configured to curve away from the distal surface of a tissue wall. Tissue contact portion 1347 may be substantially perpendicular to longitudinal axis 1333. Alternatively, tissue contact portion 1347 may be slightly curved to conform to the distal surface of a tissue wall. Tissue contact portion 1347 may be proximal to proximal end 1331 of hub 1330 to prevent hub 1330 from contacting the distal surface of a tissue wall. Tissue contact portion 1347 may have an open structure which reduces the amount of material coming into contact with a distal surface of a tissue wall. This open structure may reduce a response by a tissue wall to tissue contact portion 1347. In one embodiment as shown in FIGS. 4A-4B, tissue contact portion 1347 may have a footprint having an outside diameter of approximately 7 mm to 8 mm, and an inside diameter of approximately 4 mm to 5 mm. In another embodiment as shown in FIGS. 4C-4D, tissue contact portion 1347 may have a footprint having an outside diameter of approximately 8 mm to 10 mm, and an inside diameter of approximately 4 mm to 5 mm.

Petals 1340 may be sufficiently flexible to be collapsed into a delivery configuration for delivery inside a needle and expanded into a deployed configuration on a distal side of a tissue wall. Petals 1340 may be sufficiently flexible to provide shock absorption. Petals 1340 may be formed of one or more loops or lengths of wire, cut from one or more sheets of material, or made using any other suitable method. In one embodiment, petals 1340 may be formed of wire having a diameter of approximately 0.1 mm to 0.2 mm. Petals 1340 may be made of nitinol or other suitable material. Petals 1340 may be coated or treated with an antibiotic or other therapeutic agent.

In one embodiment, distal retention element 1320 may have a height of approximately 1 mm to 5 mm.

Tension element 1350 includes a proximal portion 1351 and a distal portion 1352. Proximal portion 1351 is coupled to proximal retention element 1310. Proximal portion 1351 may pass through hole 1311 of proximal retention element 1310 and coupled with one or more knots. Distal portion 1352 is positioned within central lumen 1335 of inner tube 1334. Distal portion 1352 may be coupled to inner tube 1334 with an adhesive 1339, solder or weld joint, laser weld, compression fit, or other suitable ways. Adhesive 1339 may be a two-part epoxy or other suitable material or adhesive. Distal portion 1352 may also be coupled to inner tube 1334 with one or more knots. Tension element 1350 is configured to pass through a tissue wall. Tension element 1350 may have a reduced width or thickness in order to decrease the size of the hole through a tissue wall, which may lower the likelihood of infection or other response. In one embodiment, tension element 1350 may have a diameter of approximately 0.2 mm to 0.5 mm. Tension element 1350 may be elastic or inelastic. Tension element 1350 may include a suture, wire, superelastic polymer, or other suitable material or device. Tension element 1350 may be coated or treated with an antibiotic agent. Alternatively, tension element 1350 may include an ultrathin coated stent that is stretchable and presents no interstitial spaces to surrounding tissue.

Figure 4E:
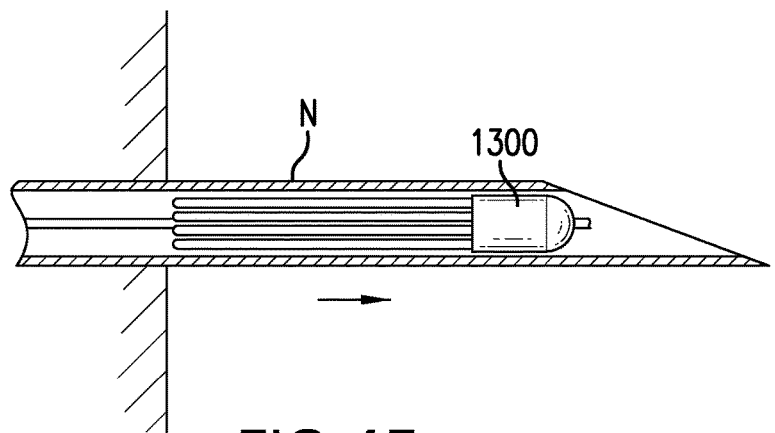
FIGS. 4E-4G show one embodiment of a method for delivering tissue anchor 1300.
Figure 4F:
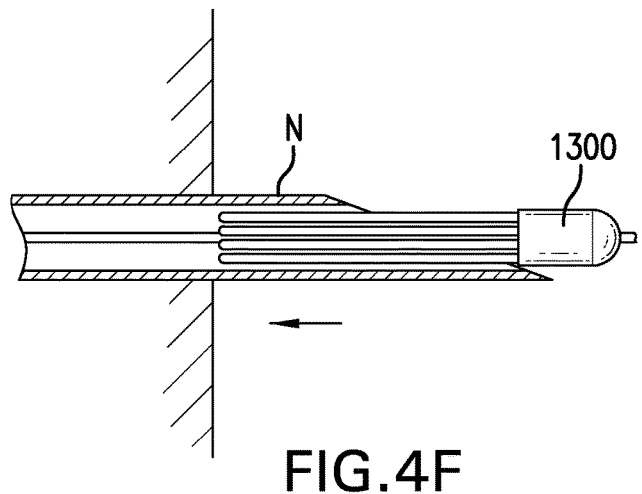
Figure 4G:
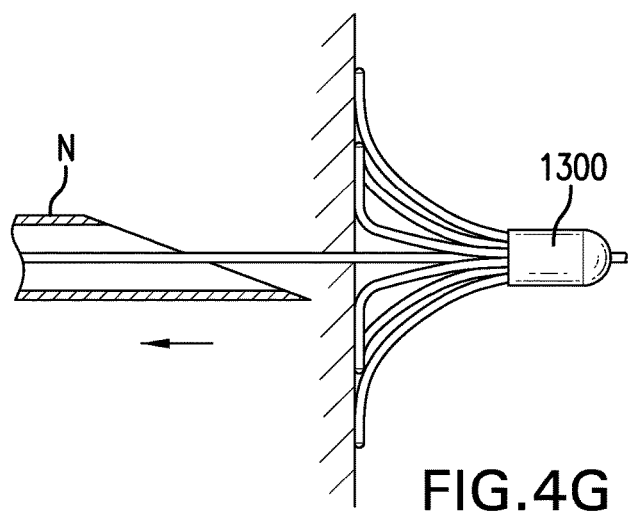

FIGS. 4E-4G show one embodiment of a method for delivering tissue anchor 1300. For clarity, a pushrod is not shown. FIG. 4E shows tissue anchor 1300 packaged inside a delivery needle N in a collapsed or delivery configuration. FIG. 4F shows tissue anchor 1300 being pushed out of the delivery needle N. FIG. 4G shows tissue anchor 1300 completely pushed out of delivery needle N and into an expanded or deployed configuration.

Figure 22A:
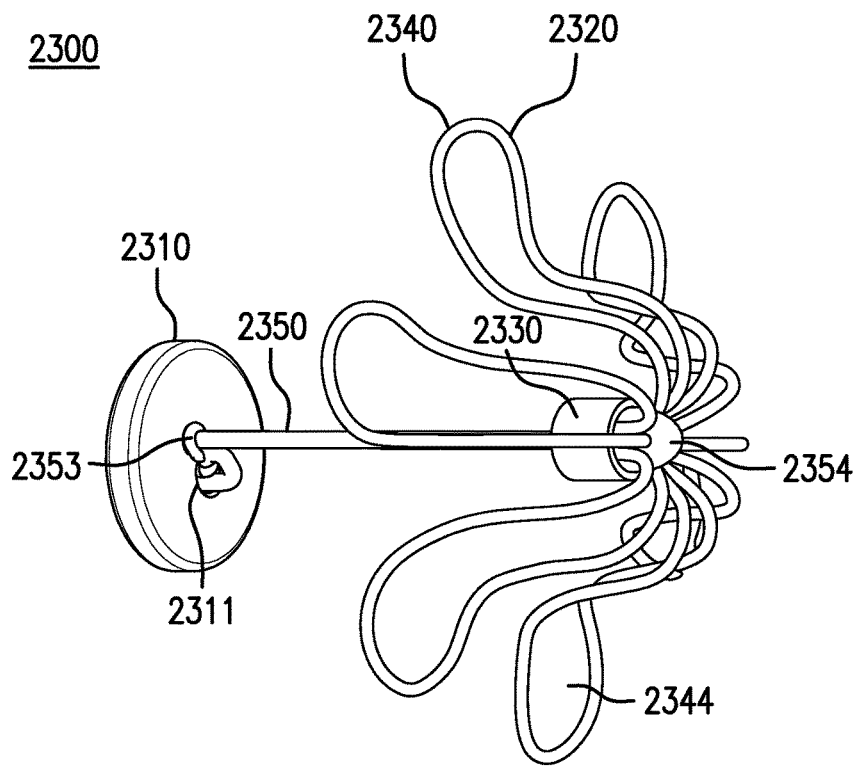
FIGS. 22A-22D show another embodiment of a tissue anchor 2300.
Figure 22B:
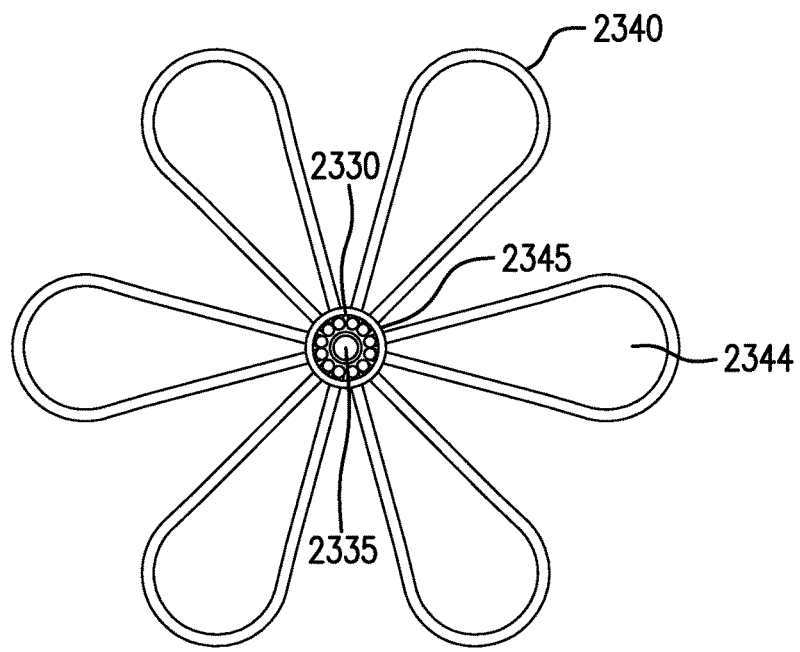
Figure 22C:
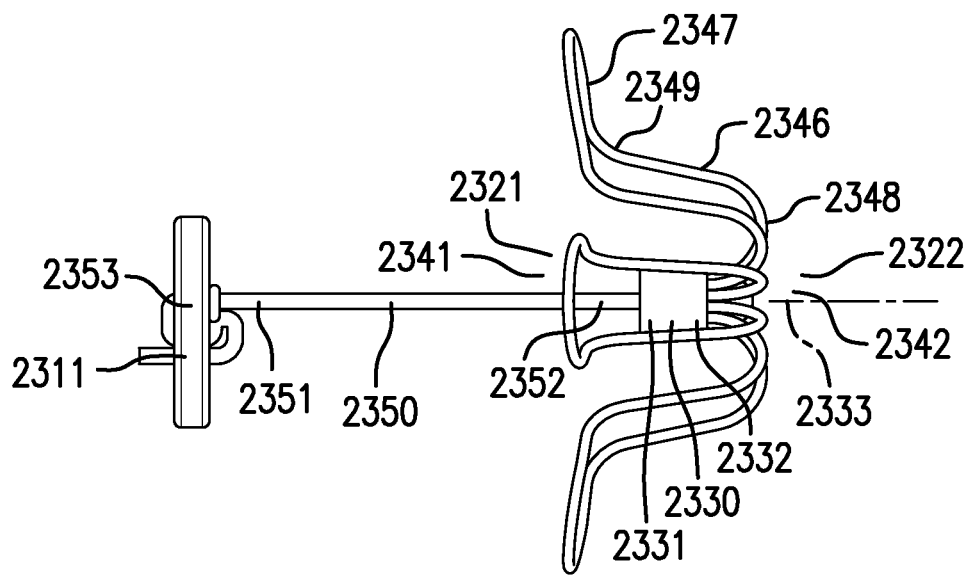
Figure 22D:
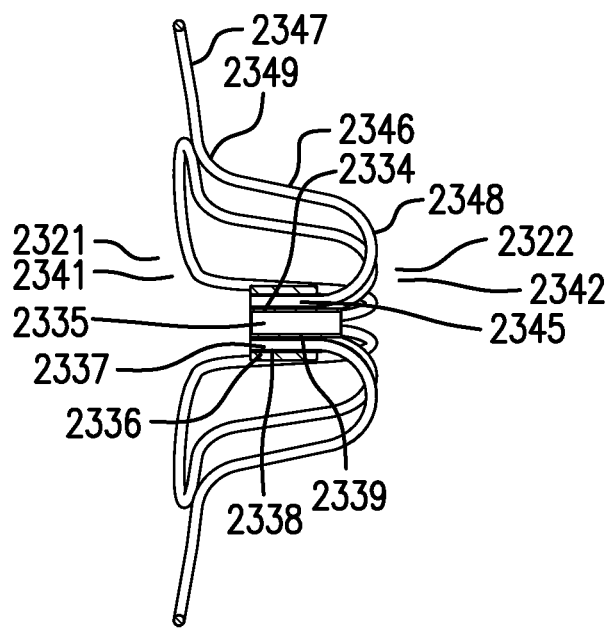

FIGS. 22A-22D show another embodiment of a tissue anchor 2300. FIG. 22A shows a perspective view of tissue anchor 2300. FIG. 22B shows a bottom view of distal retention element 2320 of tissue anchor 2300. FIG. 22C shows a side view of tissue anchor 2300. FIG. 22D shows a cross-sectional view of distal retention element 2320 of tissue anchor 2300.

The cuffs and/or sleeves described above may be anchored, for example, using tissue anchors 2300 or any other suitable tissue anchor. Other tissue anchors or features of tissue anchors that may be used with systems and methods as described herein can be found, for example, in U.S. Pat. Pub. No. 2009/0012541 to Dahl et al., which is hereby incorporated by reference in its entirety.

Tissue anchor 2300 is configured to pass through a tissue wall to retain a device. For example, tissue anchor 2300 may be configured to pass through an anchor hole in a cuff and transmurally through the wall of the esophagus to retain a cuff in the esophagus.

Tissue anchor 2300 includes a proximal retention element 2310, a distal retention element 2320, and a tension element 2350.

Proximal retention element 2310 is configured to be deployed on a proximal side of a tissue wall. Proximal retention element 2310 may be a button, a bar, or other suitable shape. In one embodiment, proximal retention element 2310 may be a button having a diameter of approximately 2 mm to 5 mm, and a thickness of approximately 0.25 mm to 1 mm. Proximal retention element 2310 may include one or more holes 2311. Proximal retention element 2310 may be at least partially radiopaque to aid in placement and monitoring.

Distal retention element 2320 is configured to be deployed on a distal side of a tissue wall. Distal retention element 2320 may include a proximal side 2321, a distal side 2322, a hub 2330, and a plurality of petals 2340.

Hub 2330 includes a proximal end 2331, a distal end 2332, and a longitudinal axis 2333. Hub 2330 includes an inner tube 2334 having a central lumen 2335. Hub 2330 also includes an outer tube 2336. Inner tube 2334 and outer tube 2336 form an annular space 2337. Inner tube 2334 and outer tube 2336 may be substantially the same length, or be of different lengths Inner tube 2334 and outer tube 2336 may be made of a stainless steel or other suitable material.

Petals 2340 each include a proximal side 2341, a distal side 2342, an open area 2344, hub portion 2345, a connecting portion 2346, and a tissue contact portion 2347. Hub portion 2345 is coupled to tissue contact portion 2347 by connecting portion 2346. Hub portion 2345 is at least partially positioned within annular space 2337. Hub portion 2345 may be coupled to inner tube 2334 and outer tube 2336 with an adhesive 2338, solder or weld joint, laser weld, compression fit, or other suitable ways. Adhesive 2338 may be a two-part epoxy or other suitable material or adhesive. In one embodiment, hub portion 2345 may have a length of approximately 0.5 mm to 2 mm. Connecting portion 2346 extends from distal end 2332 of hub 2330. Connecting portion 2346 may include a first curved portion 2348 and a second curved portion 2349. First curved portion 2348 may couple hub portion 2345 to connecting portion 2346. First curved portion 2348 may extend from distal end 2332 of hub 2330 substantially parallel to longitudinal axis 2333, and curve approximately 135 to 180 degrees away from longitudinal axis 2333. Second curved portion 2349 may couple connecting portion 2346 to tissue contact portion 2347. Second curved portion 2349 may curve approximately 45 to 90 degrees away from longitudinal axis 2333. Thus, tissue contact portion 2347 may extend outward away from longitudinal axis 2333. Connecting portion 2346 may have a length of approximately 3 mm to 5 mm.

Tissue contact portion 2347 is configured to contact a distal surface of a tissue wall. Tissue contact portion 2347 may be substantially flat, or it may be configured to curve away from the distal surface of a tissue wall. Tissue contact portion 2347 may be substantially perpendicular to longitudinal axis 2333. Alternatively, tissue contact portion 2347 may be slightly curved to conform to the distal surface of a tissue wall. Tissue contact portion 2347 may be proximal to proximal end 2331 of hub 2330 to prevent hub 2330 from contacting the distal surface of a tissue wall. Tissue contact portion 2347 may have an open structure which reduces the amount of material coming into contact with a distal surface of a tissue wall. This open structure may reduce a response by a tissue wall to tissue contact portion 2347. In one embodiment, tissue contact portion 2347 may have a footprint having an outside diameter of approximately 7 mm to 8 mm, and an inside diameter of approximately 4 mm to 5 mm. In another embodiment, tissue contact portion 2347 may have a footprint having an outside diameter of approximately 8 mm to 10 mm, and an inside diameter of approximately 4 mm to 5 mm.

Petals 2340 may be sufficiently flexible to be collapsed into a delivery configuration for delivery inside a needle and expanded into a deployed configuration on a distal side of a tissue wall. Petals 2340 may be sufficiently flexible to provide shock absorption. Petals 2340 may be formed of one or more loops or lengths of wire, cut from one or more sheets of material, or made using any other suitable method. In one embodiment, petals 2340 may be formed of wire having a diameter of approximately 0.1 mm to 0.2 mm. Petals 2340 may be made of nitinol or other suitable material. Petals 2340 may be coated or treated with an antibiotic or other therapeutic agent.

Petals 2340, especially first curved portions 2348 of connecting portions 2346, may form a distal side 2322 which is rounded or substantially flat, which may be less traumatic to surrounding tissue. Also, because petals 2340 extend from distal end 2332 of hub 2330, hub 2330 may be positioned closer to the distal surface of a tissue wall and distal retention element 2320 may have a reduced height, which may lessen the likelihood of tumbling or tipping over. In one embodiment, distal retention element 2320 may have a height of approximately 1 mm to 5 mm.

Tension element 2350 includes a proximal portion 2351 and a distal portion 2352. Proximal portion 2351 is coupled to proximal retention element 2310. Proximal portion 2351 may pass through hole 2311 of proximal retention element 2310 and coupled with one or more knots. Distal portion 2352 is positioned within central lumen 2335 of inner tube 2334. Distal portion 2352 may be coupled to inner tube 2334 with an adhesive 2339, solder or weld joint, laser weld, compression fit, or other suitable ways. Adhesive 2339 may be a two-part epoxy or other suitable material or adhesive. Distal portion 2352 may also be coupled to inner tube 2334 with one or more knots. Tension element 2350 is configured to pass through a tissue wall. Tension element 2350 may have a reduced width or thickness in order to decrease the size of the hole through a tissue wall, which may lower the likelihood of infection or other response. In one embodiment, tension element 2350 may have a diameter of approximately 0.2 mm to 0.5 mm. Tension element 2350 may be elastic or inelastic. Tension element 2350 may include a suture, wire, superelastic polymer, or other suitable material or device. Tension element 2350 may be coated or treated with an antibiotic agent. Alternatively, tension element 2350 may include an ultrathin coated stent that is stretchable and presents no interstitial spaces to surrounding tissue.

Figure 22E:
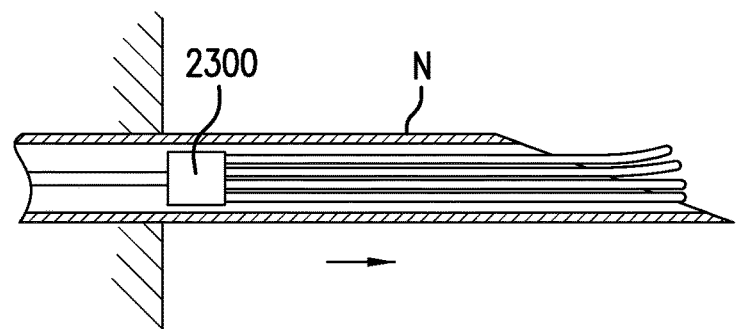
FIGS. 22E-22G show one embodiment of a method for delivering tissue anchor 2300.
Figure 22F:
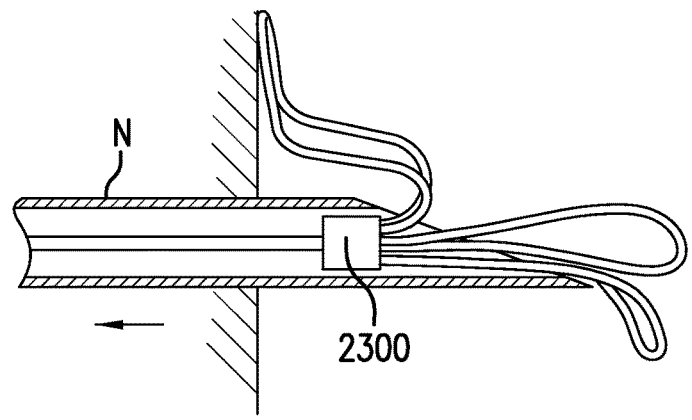
Figure 22G:
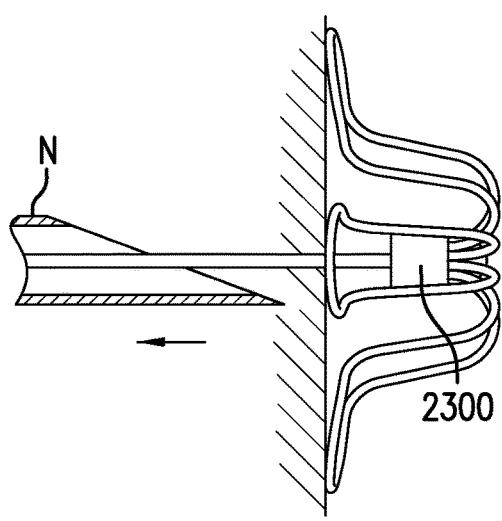

FIGS. 22E-22G show one embodiment of a method for delivering tissue anchor 2300. FIG. 22E shows tissue anchor 2300 packaged inside a delivery needle N in a collapsed or delivery configuration. FIG. 22F shows tissue anchor 2300 being pushed out of the delivery needle N. FIG. 22G shows tissue anchor 2300 completely pushed out of delivery needle N and into an expanded or deployed configuration. Because petals 2340 extend from distal end 2332 of hub 2330, tissue anchor 2300 may be configured with a shorter tension element 2350 and may be deployed with less needle penetration.

Figure 22H:
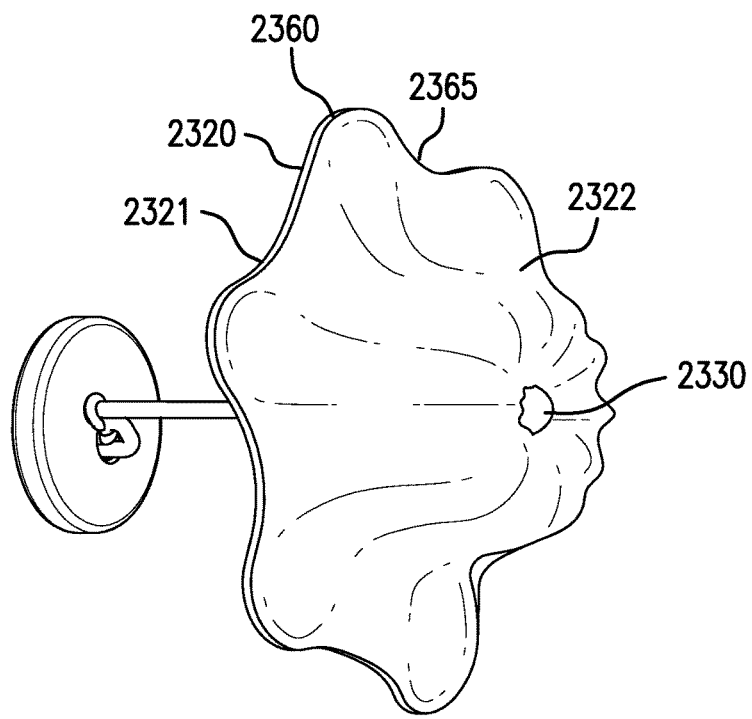
FIGS. 22H-22J show tissue anchor 2300 with various embodiments of a tissue ingrowth element 2360.
Figure 22I:
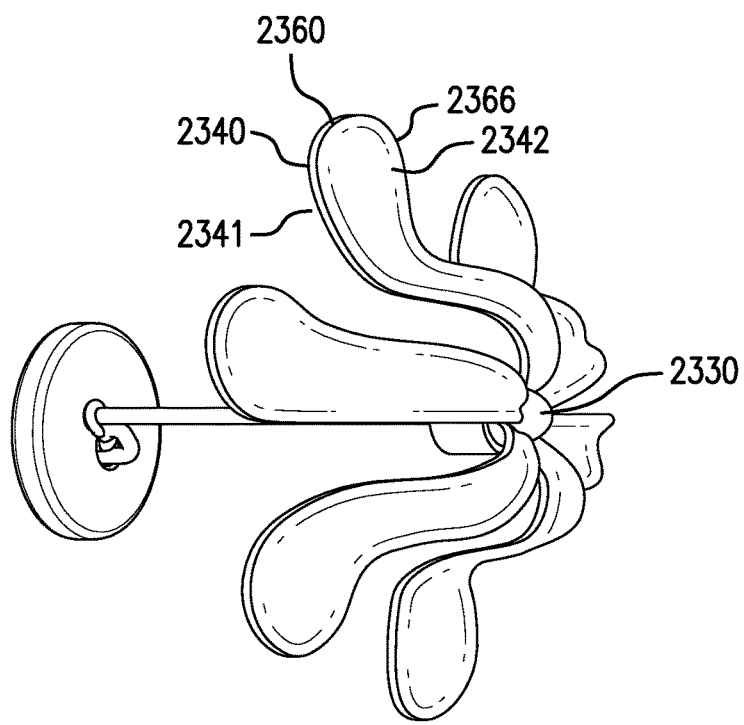
Figure 22J:
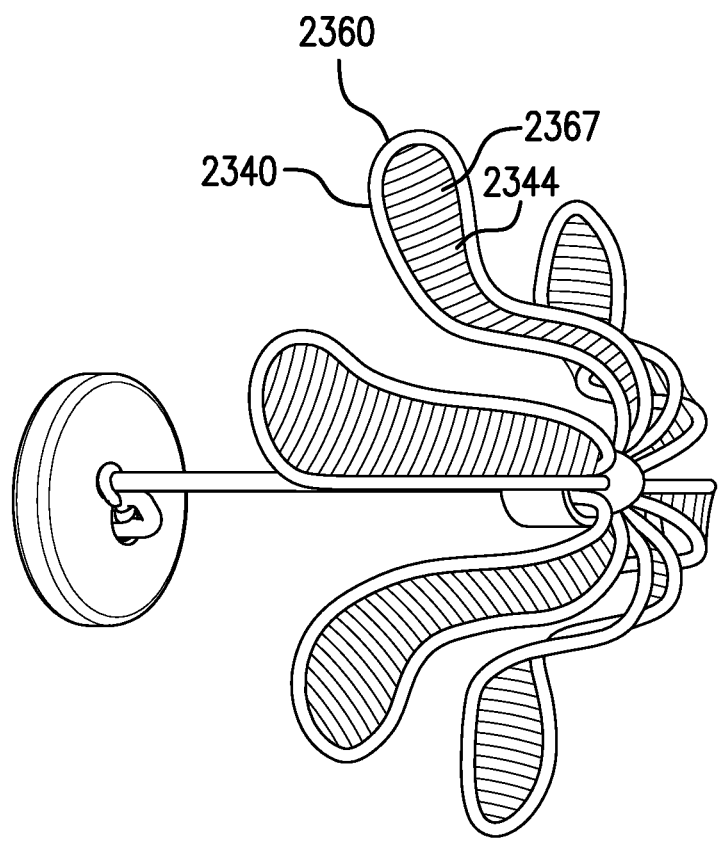

FIGS. 22H-22J show tissue anchor 2300 with various embodiments of a tissue ingrowth element 2360. Tissue ingrowth element 2360 may be coupled to distal retention element 2320. Tissue ingrowth element 2360 may allow at least a portion of a tissue surrounding distal retention element 2320 to at least partially grow into and help secure distal retention element 2320. The tissue may include tissue in the vicinity of or adjacent to a tissue wall. The tissue may include one or more layers of the tissue wall itself. Tissue ingrowth element 2360 may reduce migration or movement of tissue anchor 2300 after delivery.

FIG. 22H shows tissue anchor 2300 with one embodiment of a tissue ingrowth element 2360. Tissue ingrowth element 2360 may include a cover 2365. Cover 2365 may at least partially cover proximal side 2321 and/or distal side 2322 of distal retention element 2320. Cover 2365 may conform to distal retention element 2320. Alternatively, cover 2365 may span across proximal side 2321 of distal retention element 2320. Cover 2365 may be stitched or otherwise coupled to itself or to petals 2340. Alternatively, cover 2365 may be configured to retain itself over distal retention element 2320. For example, cover 2365 may be sufficiently elastic to fit over distal retention element 2320 and retain itself over distal retention element 2320. Cover 2365 may be coupled to proximal end 2331 and/or distal end 2332 of hub 2330, such as to inner tube 2334 of hub 2330. Cover 2365 may be coupled to hub 2330 by melt welding, or any other suitable method. Cover 2365 may be sufficiently compressible and/or collapsible to allow distal retention element 2320 to collapsed into and delivered with a delivery needle.

FIG. 22I shows tissue anchor 2300 with another embodiment of a tissue ingrowth element 2360. Tissue ingrowth element 2360 may include one or more covers 2366. Each cover 2366 may at least partially cover proximal side 2341 and/or distal side 2342 of a petal 2340. Covers 2366 may be stitched or otherwise coupled to themselves or to petals 2340. Alternatively, covers 2366 may be configured to retain themselves over petals 2340. For example, covers 2366 may be sufficiently elastic to fit over petals 2340 and retain themselves over petals 2340. Covers 2366 may be coupled to proximal end 2331 and/or distal end 2332 of hub 2330, such as to inner tube 2334 of hub 2330. Covers 2366 may be coupled to hub 2330 by melt welding, or any other suitable method. Covers 2366 may be sufficiently compressible and/or collapsible to allow distal retention element 2320 to collapsed into and delivered with a delivery needle.

FIG. 22J shows tissue anchor 2300 with another embodiment of a tissue ingrowth element 2360. Tissue ingrowth element 2360 may include a webbing 2367. Webbing 2367 may be formed at least partially in open area 2344 of one or more petals 2340. Alternatively, or in addition, webbing 2367 may be formed at least partially in one or more areas between petals 2340. Webbing 2367 may be coupled to petals 2340 by melt welding, or any other suitable method. Webbing 2367 may be sufficiently compressible and/or collapsible to allow distal retention element 2320 to collapsed into and delivered with a delivery needle.

Tissue ingrowth element 2360 may be used with any suitable tissue anchor, such as a T-tag. Tissue ingrowth element 2360 may be used with any suitable distal retention element, such as those described in U.S. Pat. Nos. 8,070,743 and 8,182,459, and U.S. Patent Application Publication 2009/0012541. Tissue ingrowth element 2360 may be used with any suitable frame or structure that is collapsible, compressible, and/or may be delivered inside a delivery needle.

Tissue ingrowth element 2360 may include a mesh made of fabric, plastic, metal, or any other suitable material. For example, tissue ingrowth element 2360 may include a knitted or woven material made of a polyester or polypropylene. Tissue ingrowth element 2360 may have a mesh size that allows or promotes tissue ingrowth, such as a mesh size ranging from about 6 μm to about 2.5 mm. Tissue ingrowth element 2360 may also have a mesh size large enough to permit macrophages to pass through, such as a mesh size greater than about 80-100 μm.

Figure 23A:
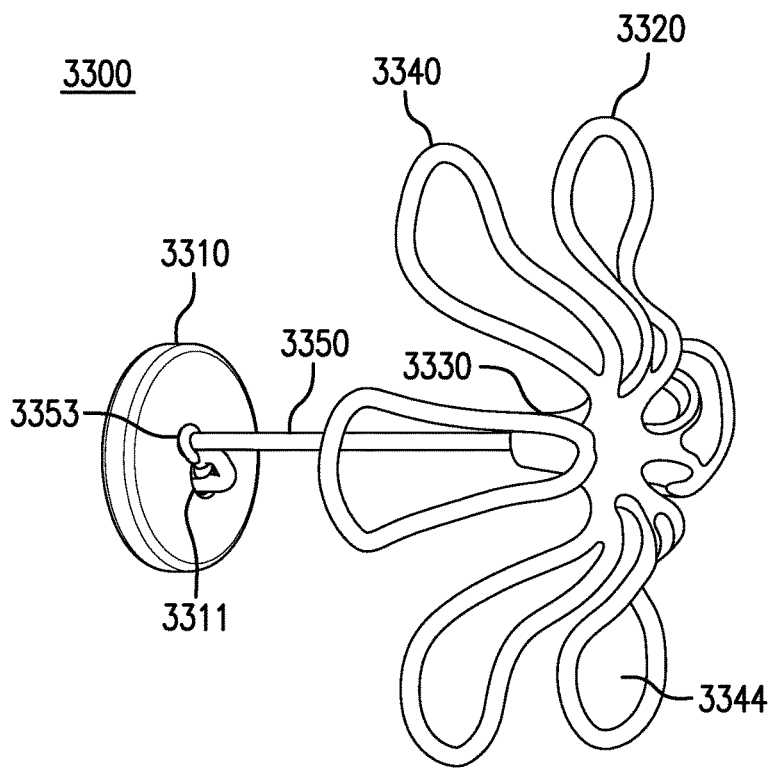
FIGS. 23A-23C show another embodiment of a tissue anchor 3300.
Figure 23B:
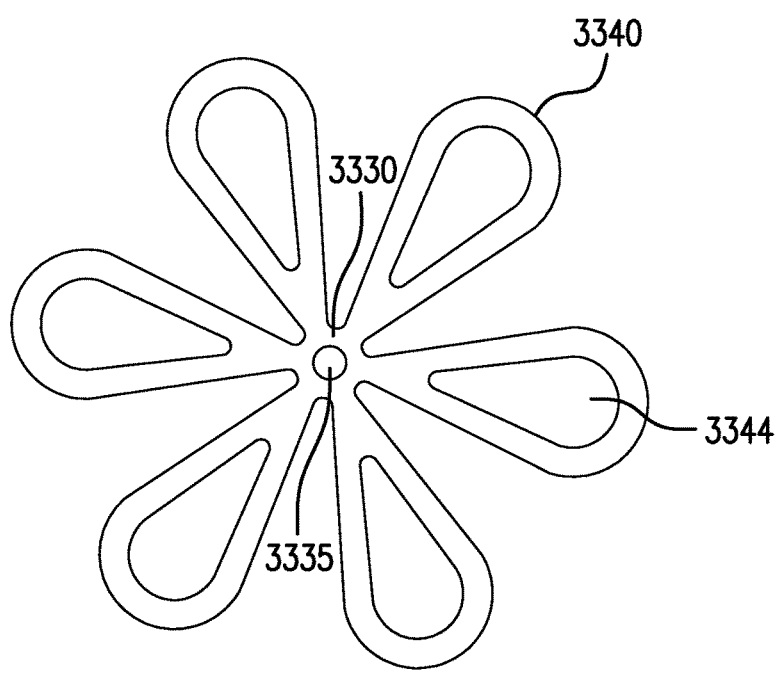
Figure 23C:
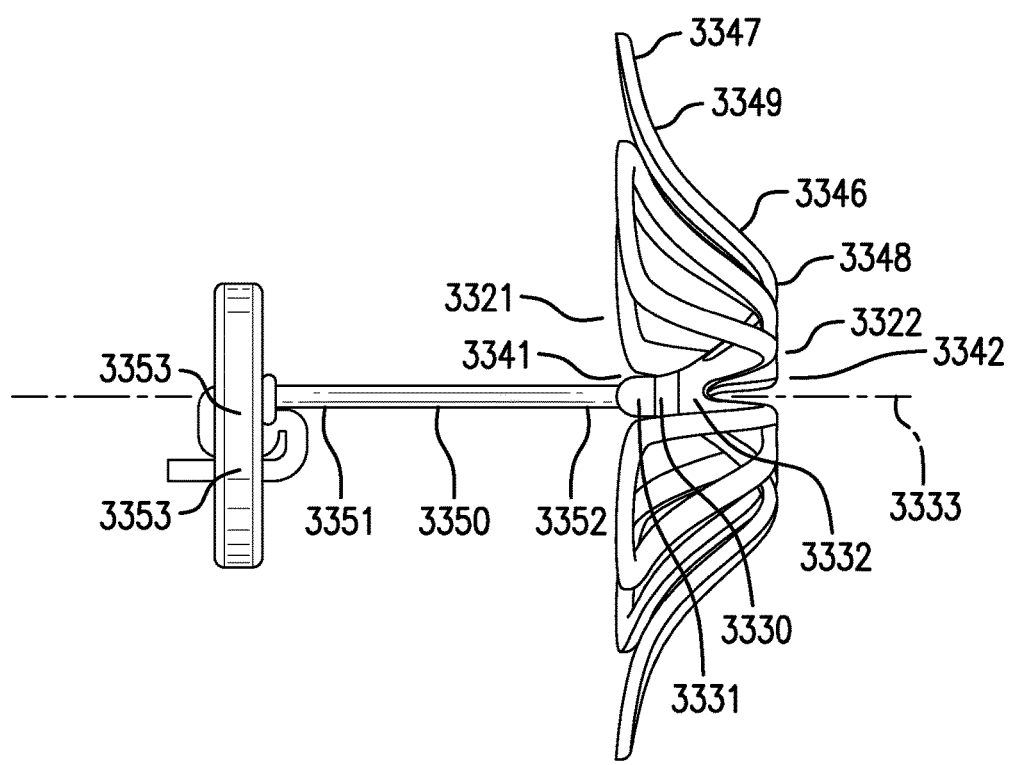

FIGS. 23A-23C show another embodiment of a tissue anchor 3300. FIG. 23A shows a perspective view of tissue anchor 3300. FIG. 23B shows a top view of tissue anchor 3300. FIG. 23C shows a side view of tissue anchor 3300.

The cuffs and/or sleeves described above may be anchored, for example, using tissue anchors 3300 or any other suitable tissue anchor. Other tissue anchors or features of tissue anchors that may be used with systems and methods as described herein can be found, for example, in U.S. Pat. Pub. No. 2009/0012541 to Dahl et al., which is hereby incorporated by reference in its entirety.

Tissue anchor 3300 is configured to pass through a tissue wall to retain a device. For example, tissue anchor 3300 may be configured to pass through an anchor hole in a cuff and transmurally through the wall of the esophagus to retain a cuff in the esophagus.

Tissue anchor 3300 includes a proximal retention element 3310, a distal retention element 3320, and a tension element 3350.

Proximal retention element 3310 is configured to be deployed on a proximal side of a tissue wall. Proximal retention element 3310 may be a button, a bar, or other suitable shape. In one embodiment, proximal retention element 3310 may be a button having a diameter of approximately 2 mm to 5 mm, and a thickness of approximately 0.25 mm to 1 mm. Proximal retention element 3310 may include one or more holes 3311. Proximal retention element 3310 may be at least partially radiopaque to aid in placement and monitoring.

Distal retention element 3320 is configured to be deployed on a distal side of a tissue wall. Distal retention element 3320 may include a proximal side 3321, a distal side 3322, a hub 3330, and a plurality of petals 3340.

Hub 3330 includes a proximal end 3331, a distal end 3332, and a longitudinal axis 3333.

Petals 3340 each include a proximal side 3341, a distal side 3342, an open area 3344, a connecting portion 3346 and a tissue contact portion 3347. Tissue contact portion 3347 is coupled to hub 3330 by connecting portion 3346. Connecting portion 3346 extends from distal end 3332 of hub 3330. Connecting portion 3346 may include a first curved portion 3348 and a second curved portion 3349. First curved portion 3348 may couple hub 3330 to connecting portion 3346. First curved portion 3348 may extend from distal end 3332 of hub 3330 substantially parallel to longitudinal axis 3333, and curve approximately 135 to 180 degrees away from longitudinal axis 3333. Second curved portion 3349 may couple connecting portion 3346 to tissue contact portion 3347. Second curved portion 3349 may curve approximately 45 to 90 degrees away from longitudinal axis 3333. Thus, tissue contact portion 3347 may extend outward away from longitudinal axis 3333. Connecting portion 3346 may have a length of approximately 3 mm to 5 mm.

Tissue contact portion 3347 is configured to contact a distal surface of a tissue wall. Tissue contact portion 3347 may be substantially flat, or it may be configured to curve away from the distal surface of a tissue wall. Tissue contact portion 3347 may be substantially perpendicular to longitudinal axis 3333. Alternatively, tissue contact portion 3347 may be slightly curved to conform to the distal surface of a tissue wall. Tissue contact portion 3347 may be proximal to proximal end 3331 of hub 3330 to prevent hub 3330 from contacting the distal surface of a tissue wall. Tissue contact portion 3347 may have an open structure which reduces the amount of material coming into contact with a distal surface of a tissue wall. This open structure may reduce a response by a tissue wall to tissue contact portion 3347. In one embodiment, tissue contact portion 3347 may have a footprint having an outside diameter of approximately 7 mm to 8 mm, and an inside diameter of approximately 4 mm to 5 mm. In another embodiment, tissue contact portion 3347 may have a footprint having an outside diameter of approximately 8 mm to 10 mm, and an inside diameter of approximately 4 mm to 5 mm.

Petals 3340 may be sufficiently flexible to be collapsed into a delivery configuration for delivery inside a needle and expanded into a deployed configuration on a distal side of a tissue wall. Petals 3340 may be sufficiently flexible to provide shock absorption. Petals 2340 may be formed of one or more loops or lengths. Petals 2340 may have a thickness of approximately 0.1 mm to 0.2 mm. Hub 3330 and petals 3340 may be laser cut, stamped, or otherwise manufactured from a single piece of material, such as a sheet or tube of material. Petals 3340 may be set into a desired shape by heat setting, cold working, or other suitable ways. Hub 3330 and petals 3340 may be made of nitinol or other suitable material. Petals 3340 may be coated or treated with an antibiotic or other therapeutic agent.

Petals 3340, especially first curved portions 3348 of connecting portions 3346, may form a distal side 3322 which is rounded or substantially flat, which may be less traumatic to surrounding tissue. Also, because petals 3340 extend from distal end 3332 of hub 3330, hub 3330 may be positioned closer to the distal surface of a tissue wall and distal retention element 3320 may have a reduced height, which may lessen the likelihood of tumbling or tipping over. In one embodiment, distal retention element 3320 may have a height of approximately 1 mm to 5 mm.

Tension element 3350 includes a proximal portion 3351 and a distal portion 3352. Proximal portion 3351 is coupled to proximal retention element 3310. Proximal portion 3351 may pass through hole 3311 of proximal retention element 3310 and coupled with one or more knots. Distal portion 3352 is positioned within central lumen 3335 of inner tube 3334. Distal portion 3352 may be coupled to inner tube 3334 with an adhesive 3339, solder or weld joint, laser weld, compression fit, or other suitable ways. Adhesive 3339 may be a two-part epoxy or other suitable material or adhesive. Distal portion 3352 may also be coupled to inner tube 3334 with one or more knots. Tension element 3350 is configured to pass through a tissue wall. Tension element 3350 may have a reduced width or thickness in order to decrease the size of the hole through a tissue wall, which may lower the likelihood of infection or other response. In one embodiment, tension element 3350 may have a diameter of approximately 0.2 mm to 0.5 mm. Tension element 3350 may be elastic or inelastic. Tension element 3350 may include a suture, wire, superelastic polymer, or other suitable material or device. Tension element 3350 may be coated or treated with an antibiotic agent. Alternatively, tension element 3350 may include an ultrathin coated stent that is stretchable and presents no interstitial spaces to surrounding tissue.

Figure 24A:
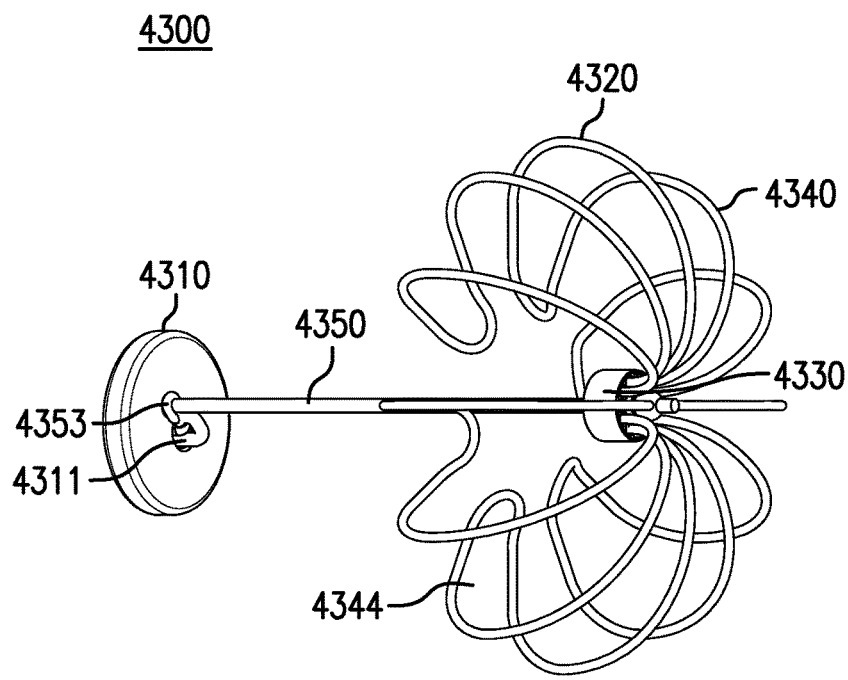
FIGS. 24A-24D show another embodiment of a tissue anchor 4300.
Figure 24B:
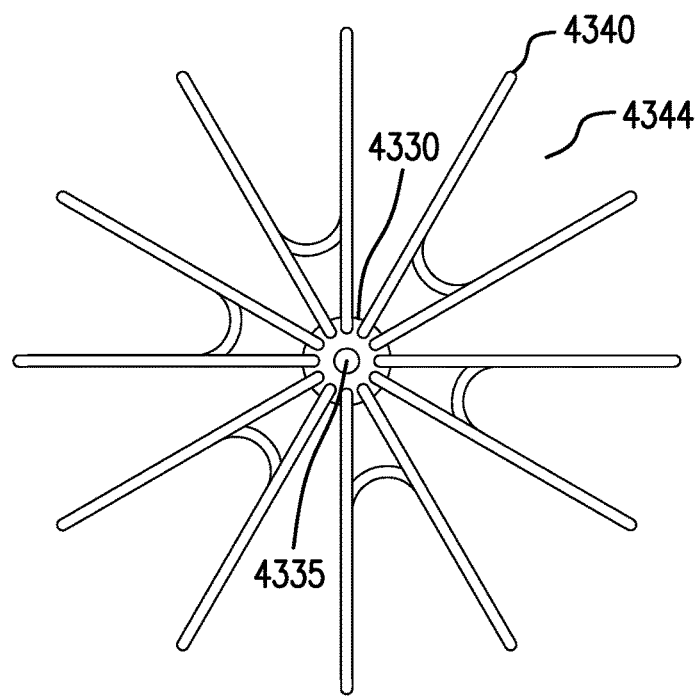
Figure 24C:
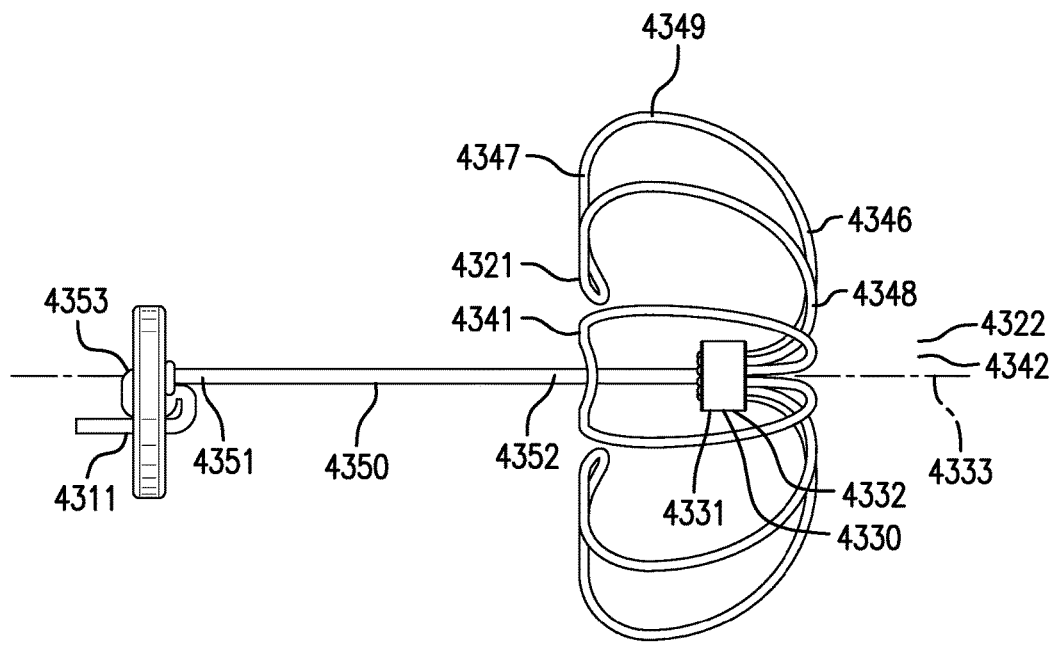
Figure 24D:
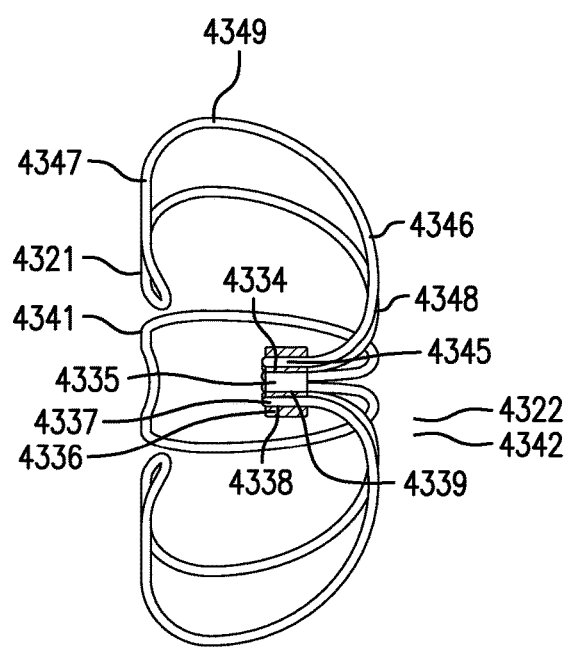

FIGS. 24A-24D show another embodiment of a tissue anchor 4300. FIG. 24A shows a perspective view of tissue anchor 4300. FIG. 24B shows a top view of distal retention element 4320 of tissue anchor 4300. FIG. 24C shows a side view of tissue anchor 4300. FIG. 24D shows a cross-sectional view of tissue anchor 4300.

The cuffs and/or sleeves described above may be anchored, for example, using tissue anchors 4300 or any other suitable tissue anchor. Other tissue anchors or features of tissue anchors that may be used with systems and methods as described herein can be found, for example, in U.S. Pat. Pub. No. 2009/0012541 to Dahl et al., which is hereby incorporated by reference in its entirety.

Tissue anchor 4300 is configured to pass through a tissue wall to retain a device. For example, tissue anchor 4300 may be configured to pass through an anchor hole in a cuff and transmurally through the wall of the esophagus to retain a cuff in the esophagus.

Tissue anchor 4300 includes a proximal retention element 4310, a distal retention element 4320, and a tension element 4350.

Proximal retention element 4310 is configured to be deployed on a proximal side of a tissue wall. Proximal retention element 4310 may be a button, a bar, or other suitable shape. In one embodiment, proximal retention element 4310 may be a button having a diameter of approximately 2 mm to 5 mm, and a thickness of approximately 0.25 mm to 1 mm. Proximal retention element 4310 may include one or more holes 4311. Proximal retention element 4310 may be at least partially radiopaque to aid in placement and monitoring.

Distal retention element 4320 is configured to be deployed on a distal side of a tissue wall. Distal retention element 4320 may include a proximal side 4321, a distal side 4322, a hub 4330, and a plurality of petals 4340.

Hub 4330 includes a proximal end 4331, a distal end 4332, and a longitudinal axis 4333. Hub 4330 includes an inner tube 4334 having a central lumen 4335. Hub 4330 also includes an outer tube 4336. Inner tube 4334 and outer tube 4336 form an annular space 4337. Inner tube 4334 and outer tube 4336 may be substantially the same length, or be of different lengths Inner tube 4334 and outer tube 4336 may be made of a stainless steel or other suitable material.

Petals 4340 each include a proximal side 4341, a distal side 4342, an open area 4344, hub portion 4345, a connecting portion 4346, and a tissue contact portion 4347. Hub portion 4345 is coupled to tissue contact portion 4347 by connecting portion 4346. Hub portion 4345 is at least partially positioned within annular space 4337. Hub portion 4345 may be coupled to inner tube 4334 and outer tube 4336 with an adhesive 4338, solder or weld joint, laser weld, compression fit, or other suitable ways. Adhesive 4338 may be a two-part epoxy or other suitable material or adhesive. In one embodiment, hub portion 4345 may have a length of approximately 0.5 mm to 2 mm. Connecting portion 4346 extends from distal end 4332 of hub 4330. Connecting portion 4346 may include a first curved portion 4348 and a second curved portion 4349. First curved portion 4348 may couple hub portion 4345 to connecting portion 4346. First curved portion 4348 may extend from distal end 4332 of hub 4330 substantially parallel to longitudinal axis 4333, and curve approximately 60 to 120 degrees away from longitudinal axis 4333. Second curved portion 4349 may couple connecting portion 4346 to tissue contact portion 4347. Second curved portion 4349 may curve approximately 150 to 210 degrees proximally toward longitudinal axis 4333. Thus, tissue contact portion 4347 may extend inward toward longitudinal axis 4333. Connecting portion 4346 may have a length of approximately 3 mm to 7 mm.

Tissue contact portion 4347 is configured to contact a distal surface of a tissue wall. Tissue contact portion 4347 may be substantially flat, or it may be configured to curve away from the distal surface of a tissue wall. Tissue contact portion 4347 may be substantially perpendicular to longitudinal axis 4333. Alternatively, tissue contact portion 4347 may be slightly curved to conform to the distal surface of a tissue wall. Tissue contact portion 4347 may be proximal to proximal end 4331 of hub 4330 to prevent hub 4330 from contacting the distal surface of a tissue wall. Tissue contact portion 4347 may have an open structure which reduces the amount of material coming into contact with a distal surface of a tissue wall. This open structure may reduce a response by a tissue wall to tissue contact portion 4347. In one embodiment, tissue contact portion 4347 may have a footprint having an outside diameter of approximately 7 mm to 8 mm, and an inside diameter of approximately 4 mm to 5 mm. In another embodiment, tissue contact portion 4347 may have a footprint having an outside diameter of approximately 8 mm to 10 mm, and an inside diameter of approximately 4 mm to 5 mm.

Petals 4340 may be sufficiently flexible to be collapsed into a delivery configuration for delivery inside a needle and expanded into a deployed configuration on a distal side of a tissue wall. Petals 4340 may be sufficiently flexible to provide shock absorption. Petals 4340 may be formed of one or more loops or lengths of wire, cut from one or more sheets of material, or made using any other suitable method. In one embodiment, petals 4340 may be formed of wire having a diameter of approximately 0.1 mm to 0.2 mm. Petals 4340 may be made of nitinol or other suitable material. Petals 4340 may be coated or treated with an antibiotic or other therapeutic agent.

Petals 4340, especially connecting portions 4346, may form a distal side 4322 which is rounded or substantially flat, which may be less traumatic to surrounding tissue. Also, because petals 4340 extend from distal end 4332 of hub 4330, hub 4330 may be positioned closer to the distal surface of a tissue wall and distal retention element 4320 may have a reduced height, which may lessen the likelihood of tumbling or tipping over. In one embodiment, distal retention element 4320 may have a height of approximately 1 mm to 5 mm.

Tension element 4350 includes a proximal portion 4351 and a distal portion 4352. Proximal portion 4351 is coupled to proximal retention element 4310. Proximal portion 4351 may pass through hole 4311 of proximal retention element 4310 and coupled with one or more knots. Distal portion 4352 is positioned within central lumen 4335 of inner tube 4334. Distal portion 4352 may be coupled to inner tube 4334 with an adhesive 4339, solder or weld joint, laser weld, compression fit, or other suitable ways. Adhesive 4339 may be a two-part epoxy or other suitable material or adhesive. Distal portion 4352 may also be coupled to inner tube 4334 with one or more knots. Tension element 4350 is configured to pass through a tissue wall. Tension element 4350 may have a reduced width or thickness in order to decrease the size of the hole through a tissue wall, which may lower the likelihood of infection or other response. In one embodiment, tension element 4350 may have a diameter of approximately 0.2 mm to 0.5 mm. Tension element 4350 may be elastic or inelastic. Tension element 4350 may include a suture, wire, superelastic polymer, or other suitable material or device. Tension element 4350 may be coated or treated with an antibiotic agent. Alternatively, tension element 4350 may include an ultrathin coated stent that is stretchable and presents no interstitial spaces to surrounding tissue.

Figure 24E:
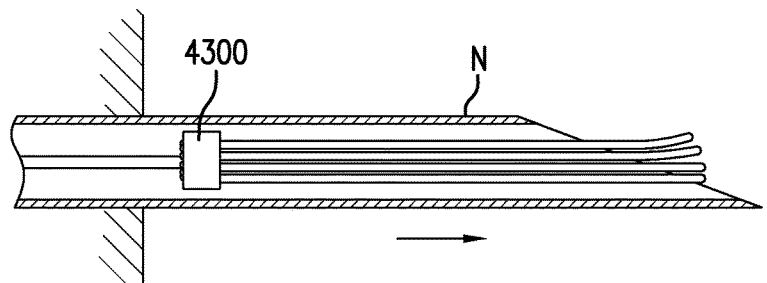
FIGS. 24E-24G show one embodiment of a method for delivering tissue anchor 4300.
Figure 24F:
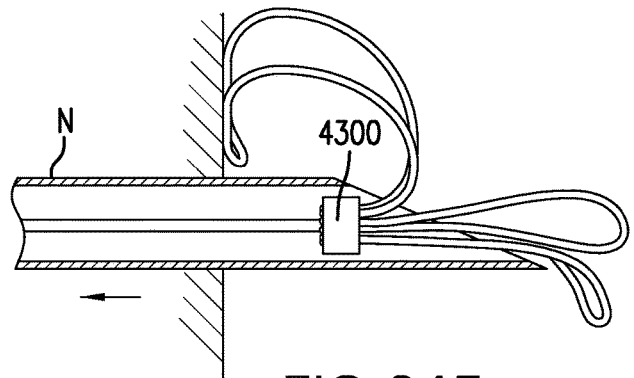
Figure 24G:
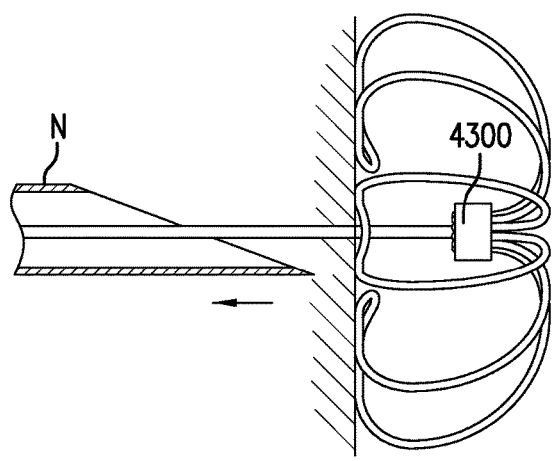

FIGS. 24E-24G show one embodiment of a method for delivering tissue anchor 4300. FIG. 24E shows tissue anchor 4300 packaged inside a delivery needle in a collapsed or delivery configuration. FIG. 24F shows tissue anchor 4300 being pushed out of the delivery needle. FIG. 24G shows tissue anchor 4300 completely pushed out of delivery needle and into an expanded or deployed configuration. Because petals 4340 extend from distal end 4332 of hub 4330, tissue anchor 4300 may be configured with a shorter tension element 4350 and may be deployed with less needle penetration.

FIGS. 24H-24K show tissue anchor 4300 with various embodiments of a tissue ingrowth element 4360. Tissue ingrowth element 4360 may be coupled to distal retention element 4320. Tissue ingrowth element 4360 may allow at least a portion of a tissue surrounding distal retention element 4320 to at least partially grow into and help secure distal retention element 4320. The tissue may include tissue in the vicinity of or adjacent to a tissue wall. The tissue may include one or more layers of the tissue wall itself. Tissue ingrowth element 4360 may reduce migration or movement of tissue anchor 4300 after delivery.

Figure 24H:
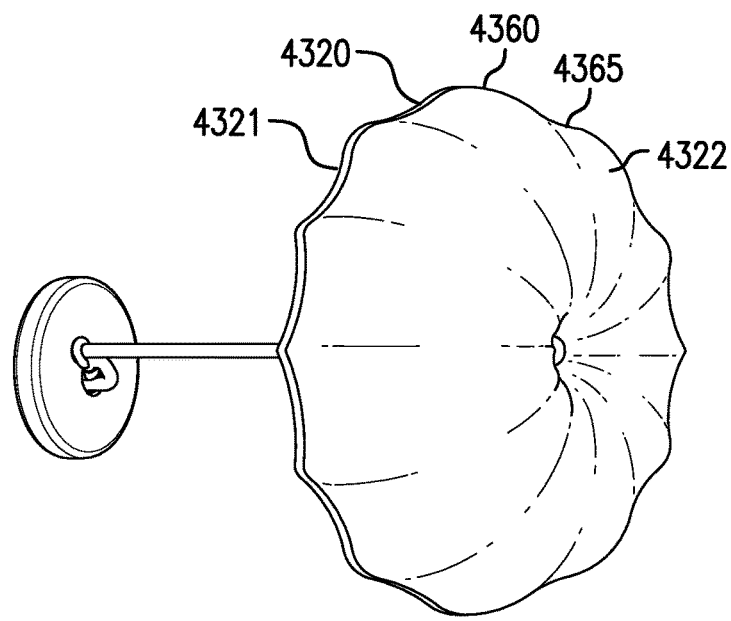
FIGS. 24H-24K show tissue anchor 4300 with various embodiments of a tissue ingrowth element 4360.
Figure 24I:
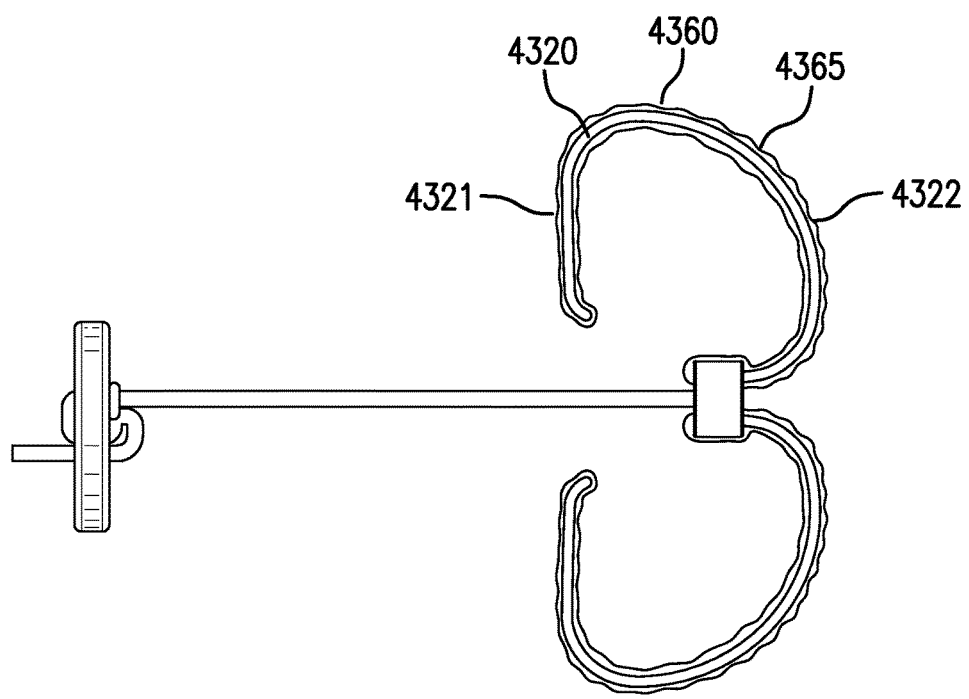

FIGS. 24H-24I shows tissue anchor 4300 with one embodiment of a tissue ingrowth element 4360. Tissue ingrowth element 4360 may include a cover 4365. Cover 4365 may at least partially cover proximal side 4321 and/or distal side 4322 of distal retention element 4320. Cover 4365 may conform to distal retention element 4320, as can be seen in the cross-sectional view shown in FIG. 24I. Alternatively, cover 4365 may span across proximal side 4321 of distal retention element 4320. Cover 4365 may be stitched or otherwise coupled to itself or to petals 4340. Alternatively, cover 4365 may be configured to retain itself over distal retention element 4320. For example, cover 4365 may be sufficiently elastic to fit over distal retention element 4320 and retain itself over distal retention element 4320. Cover 4365 may be coupled to proximal end 4331 and/or distal end 4332 of hub 4330, such as to inner tube 4334 of hub 4330. Cover 4365 may be coupled to hub 4330 by melt welding, or any other suitable method. Cover 4365 may be sufficiently compressible and/or collapsible to allow distal retention element 4320 to collapsed into and delivered with a delivery needle.

Figure 24J:
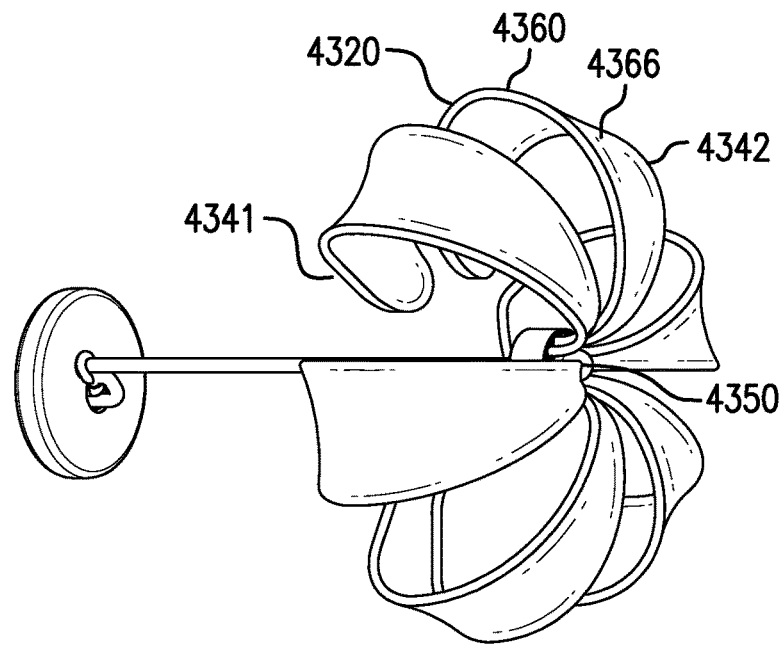

FIG. 24J shows tissue anchor 4300 with another embodiment of a tissue ingrowth element 4360. Tissue ingrowth element 4360 may include one or more covers 4366. Each cover 4366 may at least partially cover proximal side 4341 and distal side 4342 of a petal 4340. Covers 4366 may be stitched or otherwise coupled to themselves or to petals 4340. Alternatively, covers 4366 may be configured to retain themselves over petals 4340. For example, covers 4366 may be sufficiently elastic to fit over petals 4340 and retain themselves over petals 4340. Covers 4366 may be coupled to proximal end 4331 and/or distal end 4332 of hub 4330, such as to inner tube 4334 of hub 4330. Covers 4366 may be coupled to hub 4330 by melt welding, or any other suitable method. Covers 4366 may be sufficiently compressible and/or collapsible to allow distal retention element 4320 to collapsed into and delivered with a delivery needle.

Figure 24K:
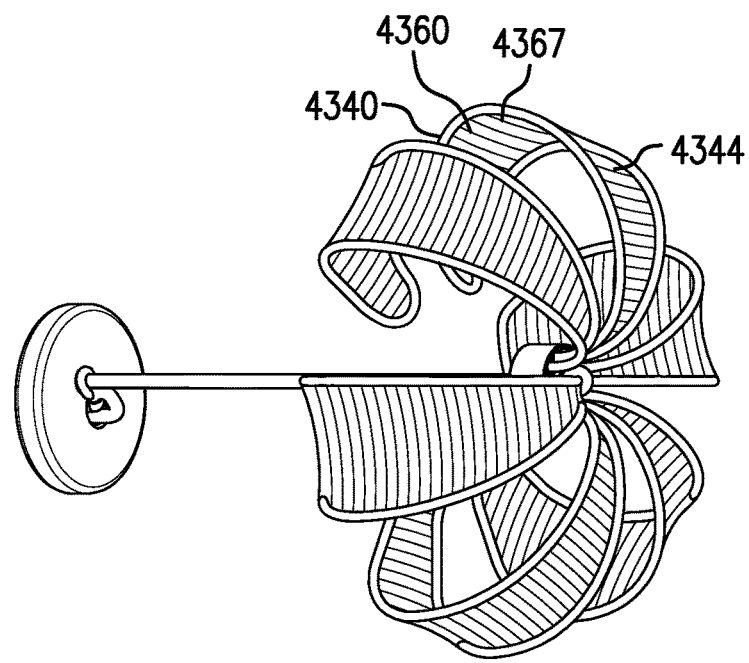

FIG. 24K shows tissue anchor 4300 with another embodiment of a tissue ingrowth element 4360. Tissue ingrowth element 4360 may include a webbing 4367. Webbing 4367 may be formed at least partially in open area 4344 of one or more petals 4340. Alternatively, or in addition, webbing 4367 may be formed at least partially in one or more areas between petals 4340. Webbing 4367 may be coupled to petals 4340 by melt welding, or any other suitable method. Webbing 4367 may be sufficiently compressible and/or collapsible to allow distal retention element 4320 to collapsed into and delivered with a delivery needle.

Tissue ingrowth element 4360 may be used with any suitable tissue anchor, such as a T-tag. Tissue ingrowth element 4360 may be used with any suitable distal retention element, such as those described in U.S. Pat. Nos. 8,070,743 and 8,182,459, and U.S. Patent Application Publication 2009/0012541. Tissue ingrowth element 4360 may be used with any suitable frame or structure that is collapsible, compressible, and/or may be delivered inside a delivery needle.

Tissue ingrowth element 4360 may include a mesh made of fabric, plastic, metal, or any other suitable material. For example, tissue ingrowth element 4360 may include a knitted or woven material made of a polyester or polypropylene. Tissue ingrowth element 4360 may have a mesh size that allows or promotes tissue ingrowth, such as a mesh size ranging from about 6 μm to about 2.5 mm. Tissue ingrowth element 4360 may also have a mesh size large enough to permit macrophages to pass through, such as a mesh size greater than about 80-100 μm.

FIGS. 5A-5C show one embodiment of a tissue marking device 1400. FIG. 5A shows a perspective view of tissue marking device 1400. FIG. 5B shows an enlarged cross-sectional view of a distal portion of tissue marking device 1400. FIG. 5C shows an enlarged end view of a distal portion tissue marking device 1400.

Tissue marking device 1400 may be used for aiding the placement of tissue anchors, identifying cancerous tissue, marking tissue before surgery, and other purposes where a temporary or permanent marking of the anatomy is desired. In some embodiments, tissue marking device 1400 may be used for purposes other than marking, such as for pinpoint delivery of a diagnostic or therapeutic agent into tissue, such as a chemotherapeutic drug for example.

Tissue marking device 1400 may include a marking tube 1410, a marking tip 1420, a dye source 1444, and a vacuum source 1460.

Marking tube 1410 includes a proximal portion 1411 and a distal portion 1412. Marking tube includes an inlet lumen 1413 and an outlet lumen 1415. Marking tube 1410 is configured to access a part of the body where the tissue is located. Marking tube 1410 may be configured to be used in a working channel of an endoscope or other device.

Marking tip 1420 may be formed at distal portion 1412 of marking tube 1410. Marking tip 1420 includes a passage 1421 formed in a wall 1414 between inlet lumen 1413 and outlet lumen 1415. Marking tip 1420 includes an opening 1426. Opening 1426 may be circular, cross-shaped, X-shaped, or any other suitable size and shape as desired for a particular tissue identification, and in some embodiments could have a first opening shape to mark a first tissue, and a second opening shape to mark a second tissue. Opening 1426 may be chamfered on the inside and/or outside. Marking tip 1420 is configured to be placed against a tissue to be marked. Marking tip 1420 may be any suitable size or shape depending on the tissue to be marked. Opening 1426 could be on a distal-facing surface of marking tip 1420 as illustrated, or on a sidewall of the marking tip 1420 in other embodiments, such as described in connection with FIGS. 7A-7E below.

Dye source 1444 may be coupled to inlet lumen 1413. Dye source 1444 may be a reservoir containing a dye for marking tissue. The dye may be gentian violet or any other suitable ink or dye. Dye source 1444 may be a syringe or other device which allows the flow of the dye to be controlled.

Optionally, a rinse source 1445 may be coupled to inlet lumen 1413. Rinse source 1445 may be a reservoir containing a rinse solution such as saline or water. Rinse source 1445 may be a syringe or other device which allows the flow of the rinse solution to be controlled.

A single solution may be used which performs both functions of the dye and the rinse solution.

A manifold 1450 may be used to couple dye source 1444 and rinse source 1445 to inlet lumen 1413. Manifold 1450 may include one or more valves 1451 which allow dye source 1444 and rinse source 1445 to be turned on and off independently.

Vacuum source 1460 may be coupled to outlet lumen 1415. Vacuum source 1460 may be a pump or other suitable device. Vacuum source 1460 is configured to draw a tissue placed against marking tip 1420 and create a seal between opening 1426 and the tissue. Vacuum source 1460 is also configured to fill marking tip 1420 with a dye from dye source 1444 and a rinse solution from rinse source 1445. Vacuum source 1460 may include controls for adjusting or programming time and pressure of vacuum applied.

Tissue marking device 1400 may be a sealed system, which allows for a given fluid to be maintained in marking tip 1420 as long as a vacuum is applied and a seal with the tissue is maintained.

Tissue marking device 1400 may be used by first applying a vacuum to marking tip 1420 to draw a portion of the tissue against opening 1426, and then providing a dye to marking tip 1420 to at least partially fill marking tip 1420 with the dye and allow the dye to contact the portion of the tissue and mark the tissue. Tissue marking device 1400 may also be used to provide a rinse solution to marking tip 1420 to at least partially fill marking tip 1420 with the rinse solution and rinse the portion of the tissue. Tissue marking device 1400 may also be used to provide a prep solution to marking tip 1420 to at least partially fill marking tip 1420 with the prep solution and prepare the portion of the tissue before providing the dye.

FIGS. 6A-6D show one embodiment of a method for using tissue marking device 1400.

Figure 6A:
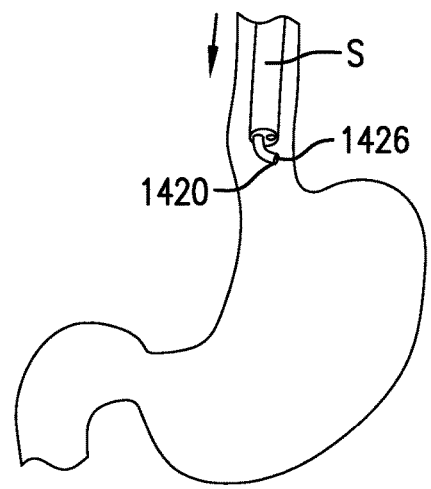
FIGS. 6A-6D show one embodiment of a method for using tissue marking device 1400.

FIG. 6A shows positioning marking tip 1420 against a tissue to be marked. An endoscope S may be used to place marking tip 1420 against the tissue.

Figure 6B:
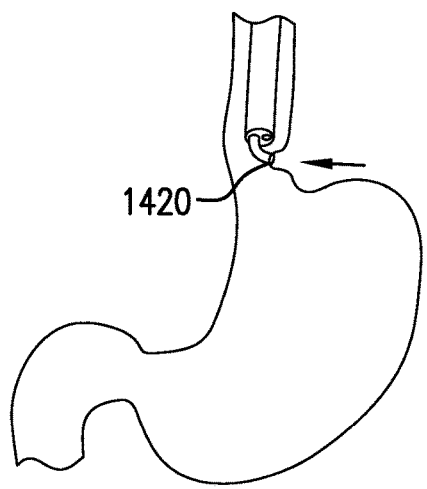

FIG. 6B shows drawing the tissue against marking tip 1420. Vacuum source 1460 is turned on to create a vacuum in marking tip 1420. Vacuum source 1460 draws the tissue against marking tip 1420, creating a seal between opening 1426 and the tissue.

Figure 6C:
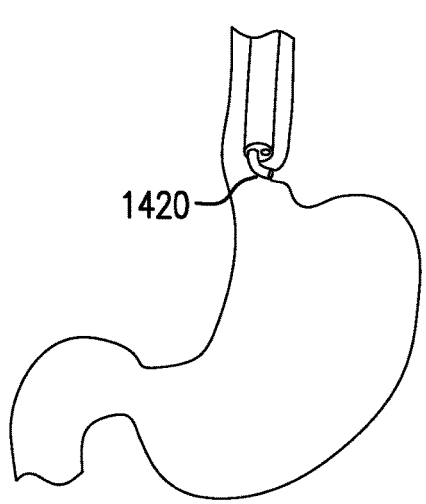

FIG. 6C shows marking the tissue. Valve 1451 for dye source 1444 is opened and vacuum source 1460 fills marking tip 1420 with a dye from dye source 1444 to mark the tissue exposed through opening 1426. Vacuum source 1460 may be used to maintain the dye in marking tip 1420 for a length of time to allow the dye to penetrate into the tissue. The dye may then be evacuated from marking tip 1420.

Optionally, rinsing marking tip 1420 and/or the tissue may be performed. Valve 1451 for rinse source 1445 is opened and vacuum source 1460 fills marking tip 1420 with a rinse solution from rinse source 1445.

Figure 6D:
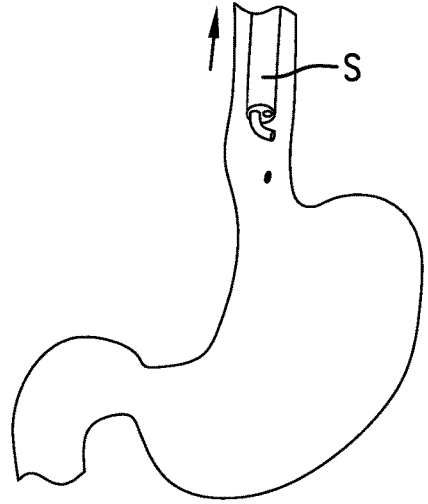

FIG. 6D shows marking tip 1420 removed from the tissue, showing the tissue mark.

Figure 7A:
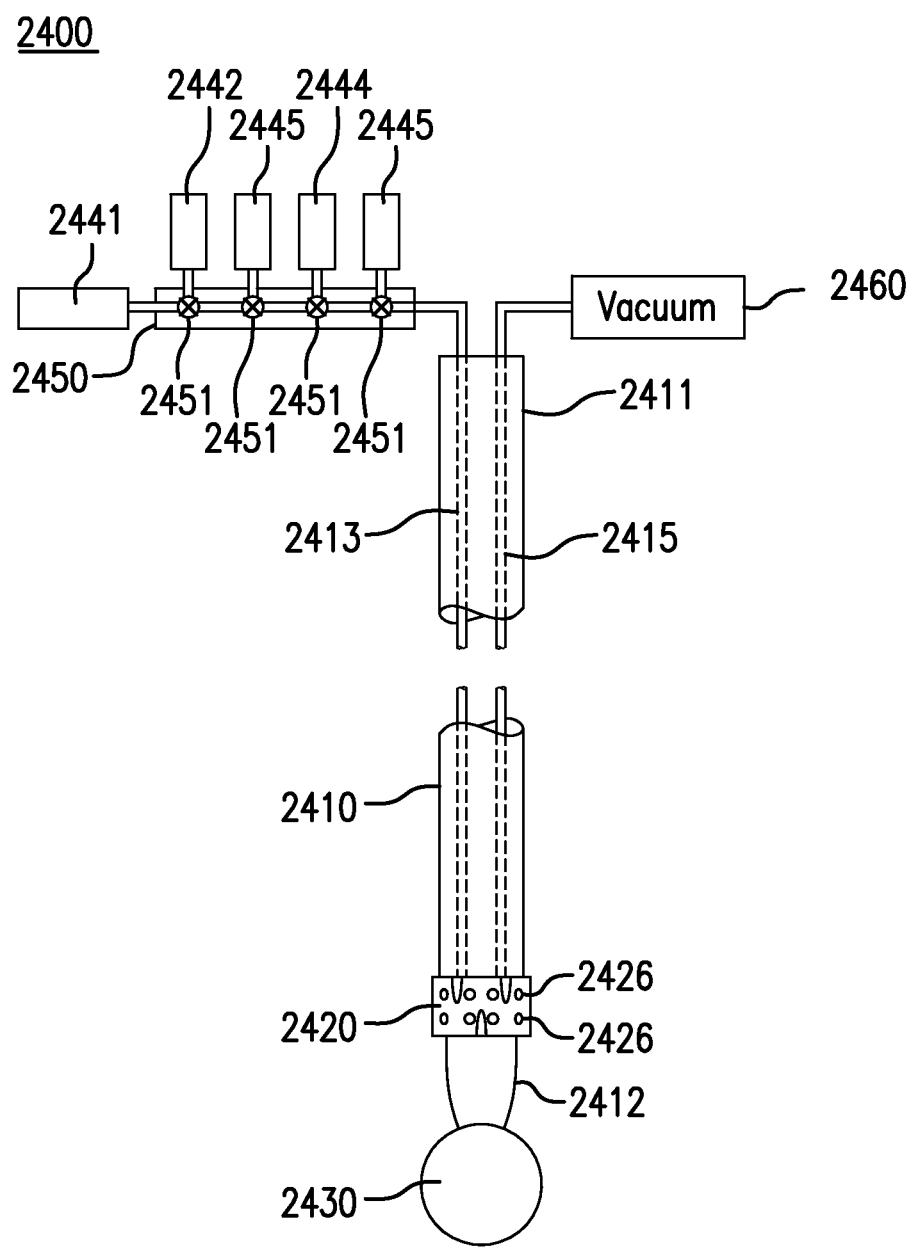
FIG. 7A shows one embodiment of a tissue marking device 2400.
Figure 7B:
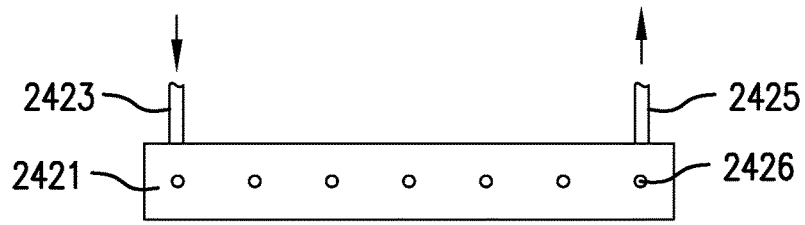
FIGS. 7B-7D show various embodiments of marking surface 2420.
Figure 7C:
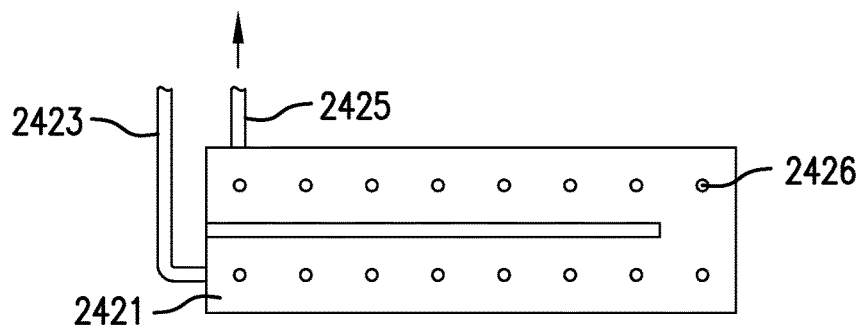
Figure 7D:
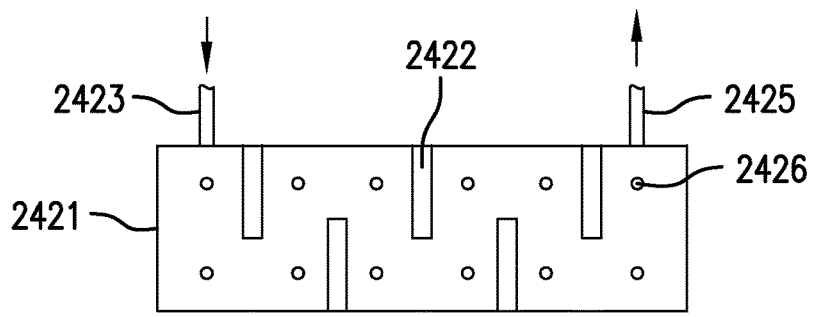
Figure 7E:
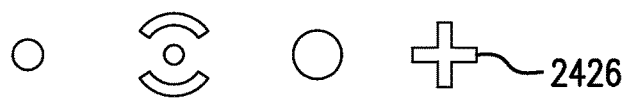
FIG. 7E shows various embodiments of openings 2426.

FIG. 7A shows one embodiment of a tissue marking device 2400. FIGS. 7B-7D show various embodiments of marking surface 2420. FIG. 7E shows various embodiments of openings 2426.

Tissue marking device 2400 may be used for aiding the placement of tissue anchors, identifying cancerous tissue, marking tissue before surgery, and other purposes. In some embodiments, tissue marking device 2400 may be used for purposes other than marking, such as for pinpoint delivery of a diagnostic or therapeutic agent into tissue, such as a chemotherapeutic drug for example.

Tissue marking device 2400 may include an access element 2410, a marking interface 2420, a positioning element 2430, a dye source 2444, and a vacuum source 2460.

Access element 2410 includes a proximal portion 2411 and a distal portion 2412. Access element 2410 may include an inlet tube 2413 and an outlet tube 2415. Access element 2410 is configured to access a part of the body where the tissue is located. In one embodiment, an access element 2410 used for esophageal access may be a catheter of suitable length and diameter to access the gastroesophageal junction or other part of the esophagus. Access element 2410 may be configured to be used with a visualization device. In other embodiments, access element 2410 may be an endoscope, a solid elongate member, or other suitable device used to access the esophagus or other bodily cavities.

Marking surface 2420 may be coupled to distal portion 2412 of access element 2410. Alternatively, marking surface 2420 may be coupled to any suitable part of access element 2410. Marking surface 2420 includes a lumen 2421 having an inlet 2423 and an outlet 2425. Inlet 2423 and outlet 2425 may be coupled to inlet tube 2413 and outlet tube 2415. Lumen 2421 may be linear, meandering, or U-shaped, as shown in FIGS. 7B-7D, or any other suitable configuration. Lumen 2421 may include one or more gaps 2422 for visualization. Marking surface 2420 includes one or more openings 2426. Openings 2426 may be arranged in one or more rows that can be regularly or irregularly spaced apart. Regularly spaced apart rows may be advantageous, for example, for calibration or measuring of distances. Openings 2426 may be circular, cross-shaped, X-shaped, or any other suitable size and shape as desired for a particular tissue identification, and in some embodiments could have a first opening shape to mark a first tissue, and a second opening shape to mark a second tissue. Openings 2426 may be chamfered on the inside and/or outside. Marking surface 2420 is configured to be placed against a tissue to be marked. Marking surface 2420 may be any suitable size or shape depending on the tissue to be marked. In one embodiment, marking surface 2420 may simply be a tube with one or more openings 2426 formed in a side of the tube.

Positioning element 2430 may be coupled to distal portion 2412 of access element 2410. Positioning element 2430 may be an expandable element, such as balloon, expandable mesh, or other suitable device. Positioning element 2430 may be coupled a known distance proximal or distal to marking surface 2420. Positioning element 2430 may be used to position marking surface 2420 with respect to an anatomical feature. In one embodiment, positioning element 2430 is a balloon configured to be expanded in the stomach, and configured to position marking surface 2420 in the esophagus a known distance from the opening of the stomach.

Optionally, a first rinse source 2441 may be coupled to inlet tube 2413. First rinse source 2441 may be a reservoir containing a first rinse solution such as saline or water. First rinse source 2441 may be a syringe or other device which allows the flow of the first rinse solution to be controlled.

Optionally, a second rinse source 2442 may be coupled to inlet tube 2413. Second rinse source 2442 may be a reservoir containing a second rinse solution such as acetic acid. Second rinse source 2442 may be a syringe or other device which allows the flow of the second rinse solution to be controlled.

Optionally, a prep source 2443 may be coupled to inlet tube 2413. Prep source 2443 may be a reservoir containing a prep solution such as isopropyl alcohol. Prep source 2443 may be a syringe or other device which allows the flow of the prep solution to be controlled.

Dye source 2444 may be coupled to inlet tube 2413. Dye source 2444 may be a reservoir containing a dye for marking tissue. The dye may be gentian violet or any other suitable ink or dye. Dye source 2444 may be a syringe or other device which allows the flow of the dye to be controlled.

Optionally, a third rinse source 2445 may be coupled to inlet tube 2413. Third rinse source 2445 may be a reservoir containing a third rinse solution such as saline or water. Third rinse source 2445 may be a syringe or other device which allows the flow of the third rinse solution to be controlled.

A single solution may be used which performs two or more functions of the first rinse solution, second rinse solution, prep solution, dye, and third rinse solution.

A manifold 2450 may be used to couple first rinse source 2441, second rinse source 2442, prep source 2443, dye source 2444, and third rinse source 2445 to inlet tube 2413. Manifold 2450 may include one or more valves 2451 which allow first rinse source 2441, second rinse source 2442, prep source 2443, dye source 2444, and third rinse source 2445 to be turned on and off independently.

Vacuum source 2460 is coupled to outlet tube 2415. Vacuum source 2460 may be a pump or other suitable device. Vacuum source 2460 is configured to create a vacuum within lumen 2421 of marking surface 2420. Vacuum source 2460 is configured to draw a tissue placed against marking surface 2420 and create a seal between openings 2426 and the tissue. Vacuum source 2460 is configured to fill lumen 2421 with a first rinse solution from first rinse source 2441, a second rinse solution from second rinse source 2442, a prep solution from prep source 2443, a dye from dye source 2444, and/or a third rinse solution from third rinse source 2445. Vacuum source 2460 may include controls for adjusting or programming time and pressure of vacuum applied.

Tissue marking device 2400 may be a sealed system, which allows for a given fluid to be maintained in lumen 2421 as long as a vacuum is applied and a seal with the tissue is maintained.

Tissue marking device 2400 may be used to first apply a vacuum to outlet 2425 of lumen 2421 to draw a portion of the tissue against opening 2426, and then to provide a dye to inlet 2423 of lumen 2421 to at least partially fill lumen 2421 with the dye and allow the dye to contact the portion of the tissue and mark the tissue. Tissue marking device 2400 may also be used to provide a rinse solution to inlet 2423 of lumen 2421 to at least partially fill lumen 2421 with the rinse solution and rinse the portion of the tissue. Tissue marking device 2400 may also be used to provide a prep solution to inlet 2423 of lumen 2421 to at least partially fill lumen 2421 with the prep solution and prepare the portion of the tissue before providing the dye.

FIGS. 8A-8F show one embodiment of a method for using tissue marking device 2400.

Figure 8A:
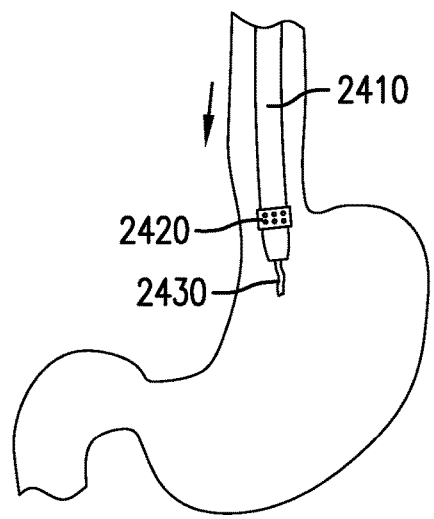
FIGS. 8A-8F show one embodiment of a method for using tissue marking device 2400.

FIG. 8A shows introducing access element 2410 into a first location, e.g., the esophagus and introducing positioning element 2430 into a second location, e.g., the stomach which in some embodiments may be distal to the first location.

Figure 8B:
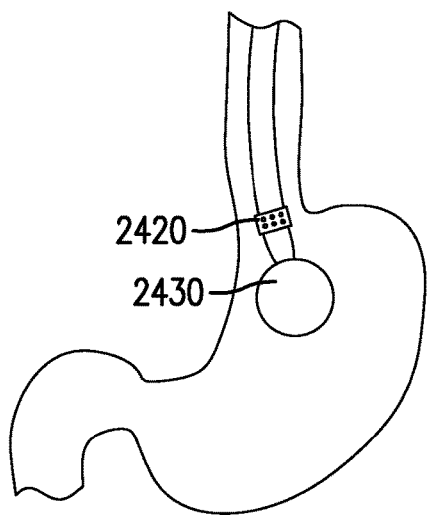

FIG. 8B shows expanding positioning element 2430 in the stomach.

Figure 8C:
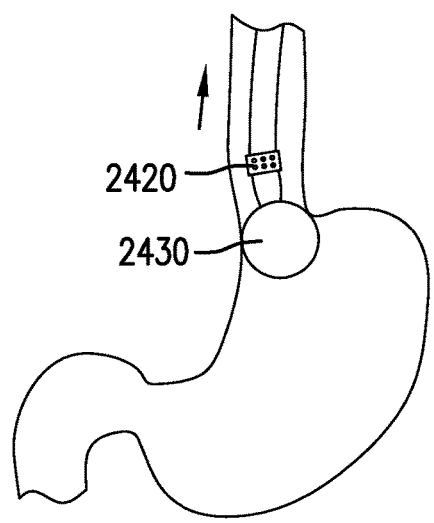

FIG. 8C shows seating positioning element 2430 against the opening of the stomach to position marking surface 2420 a known distance from the opening of the stomach in the esophagus. Alternatively, marking surface 2420 may be positioned using an initial mark made previously by tissue marking device 1400.

Figure 8D:
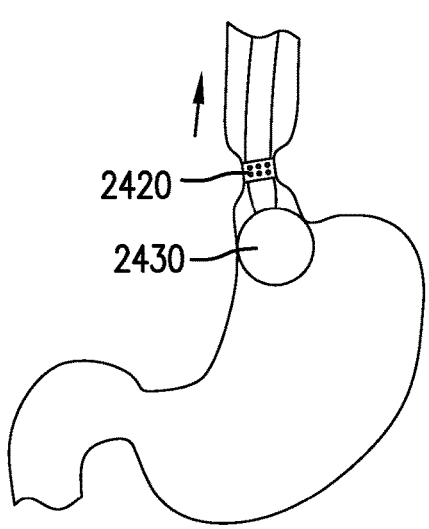

FIG. 8D shows drawing the tissue against marking surface 2420. Vacuum source 2460 is turned on to create a vacuum in lumen 2421. Vacuum source 2460 draws the tissue against marking surface 2420, creating a seal between openings 2426 and the tissue.

Optionally, rinsing the tissue may be performed one or more times. Valve 2451 for first rinse source 2441 is opened and vacuum source 2460 fills lumen 2421 with a first rinse solution from first rinse source 2441 to rinse the tissue exposed through openings 2426. Valve 2451 for second rinse source 2442 is opened and vacuum source 2460 fills lumen 2421 with a second rinse solution from second rinse source 2442 to rinse the tissue exposed through openings 2426.

Optionally, preparing the tissue may be performed. Valve 2451 for prep source 2443 is opened and vacuum source 2460 fills lumen 2421 with a prep solution from prep source 2443 to prepare the tissue exposed through openings 2426.

Figure 8E:
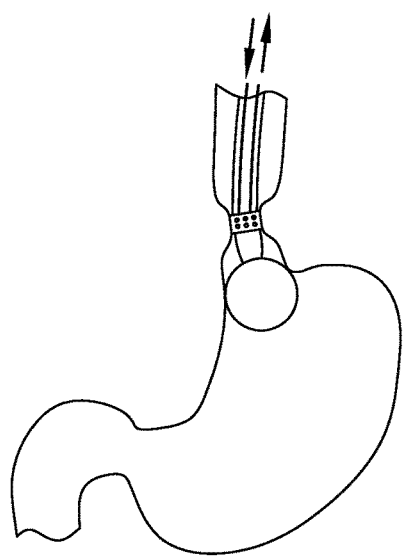

FIG. 8E shows marking the tissue. Valve 2451 for dye source 2444 is opened and vacuum source 2460 fills lumen 2421 with a dye from dye source 2444 to mark the tissue exposed through openings 2426. Vacuum source 2460 may be used to maintain the dye in lumen 2421 for a length of time to allow the dye to penetrate into the tissue. The dye is then evacuated from lumen 2421.

Optionally, rinsing lumen 2421 and/or the tissue may be performed. Valve 2451 for third rinse source 2445 is opened and vacuum source 2460 fills lumen 2421 with a third rinse solution from third rinse source 2445 to rinse lumen 2421 and/or the tissue exposed through openings 2426.

Figure 8F:
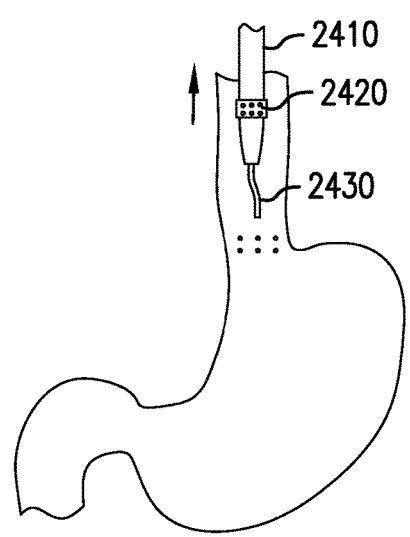

FIG. 8F shows marking surface 2420 removed from the tissue, showing the tissue marks.

Figure 9A:
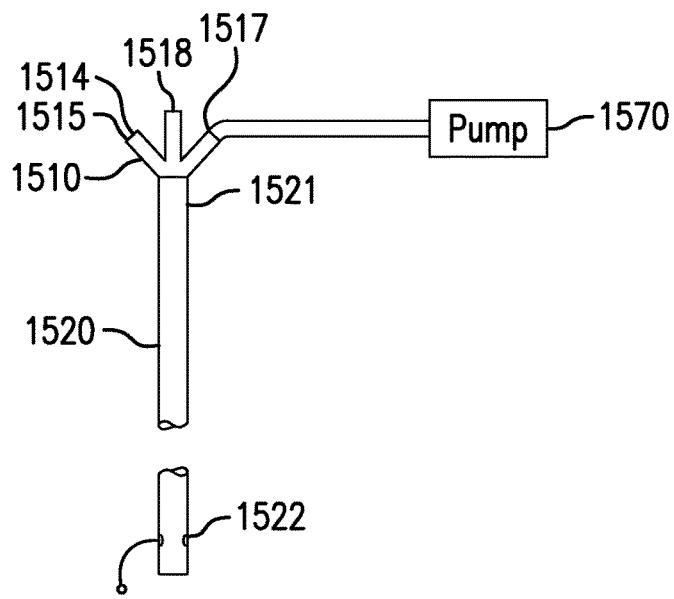
FIGS. 9A-9C show one embodiment of a sleeve delivery device 1500.
Figure 9B:
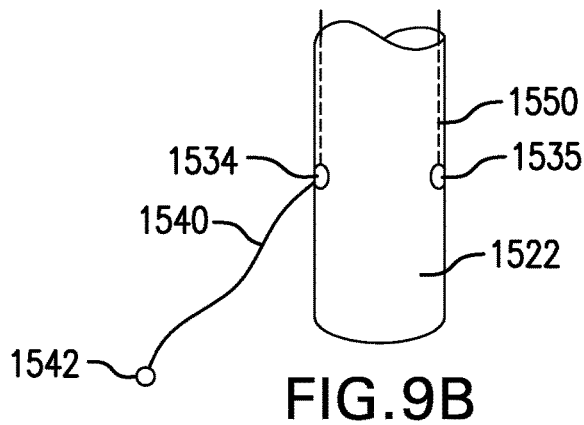
Figure 9C:
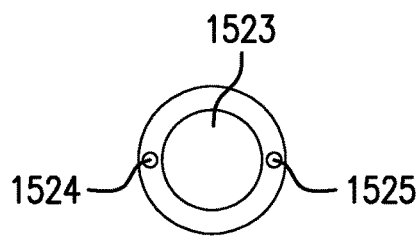

FIGS. 9A-9C show one embodiment of a sleeve delivery device 1500. FIG. 9A shows a perspective view of sleeve delivery device 1500. FIG. 9B shows an enlarged view of a distal portion of sleeve delivery device 1500. FIG. 9C shows a cross-sectional view of sleeve delivery device 1500.

Sleeve delivery device 1500 may be used to deliver a gastrointestinal sleeve. Sleeve delivery device 1500 may also be used to deliver a gastrointestinal cuff together with or apart from a gastrointestinal sleeve.

Sleeve delivery device 1500 may include a handle 1510, a delivery catheter 1520, a sealing element 1540, a release element 1550, and a pump 1570.

Handle 1510 may include a sealing port 1514, a release port 1515, a pump port 1517, and a snare port 1518. Snare port 1518 is configured to receive a loop snare or other grasping device.

Delivery catheter 1520 includes a proximal portion 1521 and a distal portion 1522. Proximal portion 1521 is coupled to handle 1510. Distal portion 1522 is configured to receive a proximal portion of a gastrointestinal sleeve. Distal portion 1522 may be curved to facilitate placement into the pylorus and/or intestine. Delivery catheter 1520 includes a delivery lumen 1523, a sealing lumen 1524, and a release lumen

1525. Delivery lumen 1523 is configured to receive at least a distal portion of a gastrointestinal sleeve which may be inverted inside delivery lumen 1523. Sealing lumen 1524 is in communication with a sealing opening 1534 formed in a side of distal portion 1522. Release lumen 1525 is in communication with a release opening 1535 formed in a side of distal portion 1522.

Sealing element 1540 is configured to form a substantially fluid-tight seal between a proximal portion of a sleeve, such as a gastrointestinal sleeve, and distal portion 1522 of delivery catheter 1520, when a proximal portion of a gastrointestinal sleeve is placed over distal portion 1522 of delivery catheter 1520. Sealing element 1540 is also configured to retain a gastrointestinal sleeve to delivery catheter 1520 during delivery. Sealing element 1540 may be, for example, a suture, wire, or other means that runs through sealing lumen 1524, exits out of sealing opening 1534, and wraps one or more times around a proximal portion of a gastrointestinal sleeve placed over distal portion 1522 of delivery catheter 1520. Sealing element 1540 may include a distal portion 1542 having a loop or a ring.

Release element 1550 is slidably disposed in release lumen 1525. Release element 1550 is configured to retain a distal portion 1542 of sealing element 1540. Release element 1550 is exposed at release opening 1535. Release element 1550 may be a wire. Alternatively, release element 1550 may be a suture or other suitable device.

Pump 1570 is configured to be coupled to pump port 1517. Pump 1570 is configured to pump a fluid such as water into delivery lumen 1523 to evert a gastrointestinal sleeve loaded onto delivery catheter 1520. Pump 1570 may include controls for pressure, volume, flow rate, time, or other parameters.

Figure 9D:
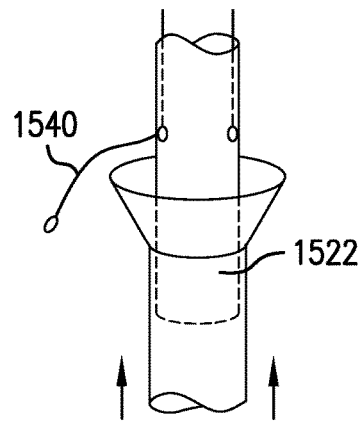
FIGS. 9D-9G show one embodiment of a method for loading sleeve delivery device 1500.
Figure 9E:
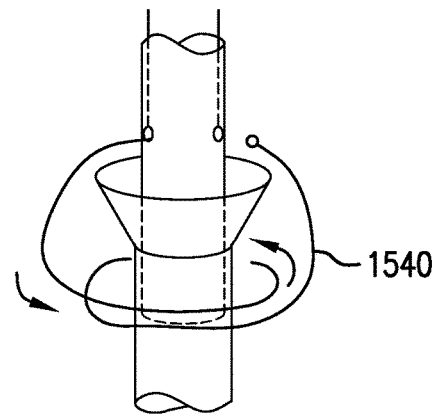
Figure 9F:
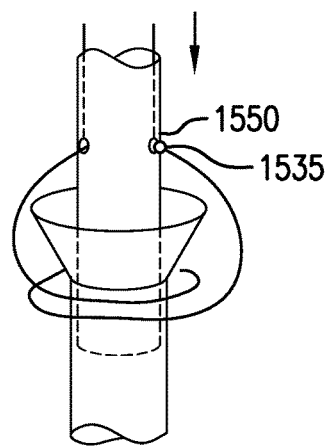
Figure 9G:
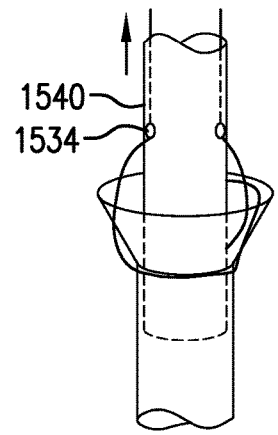

FIGS. 9D-9G show one embodiment of a method for loading sleeve delivery device 1500. FIG. 9D shows placing a proximal portion of a gastrointestinal sleeve over distal portion 1522 of delivery catheter 1520. FIG. 9E shows wrapping sealing element 1540 around the proximal portion of the gastrointestinal sleeve. FIG. 9F shows securing distal portion 1542 of sealing element 1540 in release opening 1535 using release element 1550. FIG. 9G shows tightening of sealing element 1540 around the proximal portion of the gastrointestinal sleeve. The loading may be completed by inserting a grasper, such as a loop snare through delivery lumen 1523 and the gastrointestinal sleeve, sealing a distal portion of the gastrointestinal sleeve, and using the loop snare to pull the distal portion of the gastrointestinal sleeve into delivery lumen 1523 to invert the gastrointestinal sleeve into delivery lumen 1523. Further examples of everting systems and methods that can be used with the systems and methods disclosed herein can be found, for example, in U.S. Pat. No. 8,118,774 and U.S. Pat. Pub. No. 2007/0198074, both of which are incorporated by reference in their entireties.

Figure 10A:
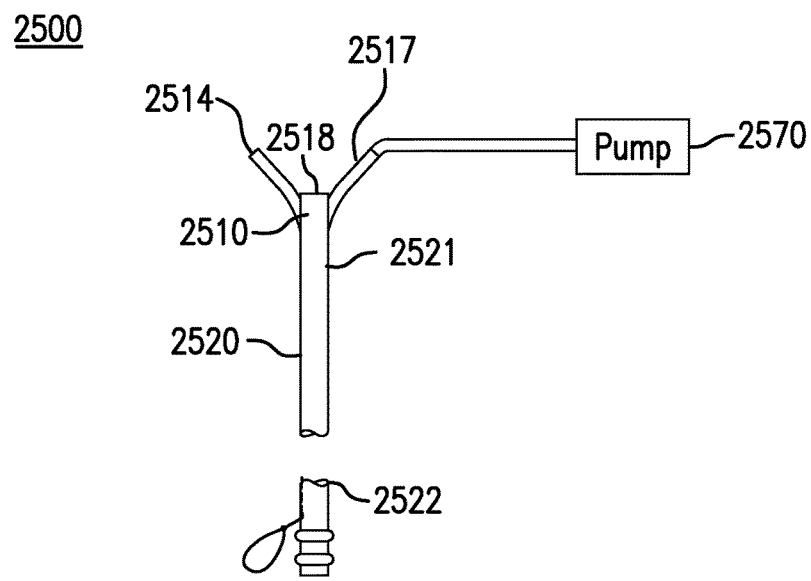
FIGS. 10A-10C show another embodiment of a sleeve delivery device 2500.
Figure 10B:
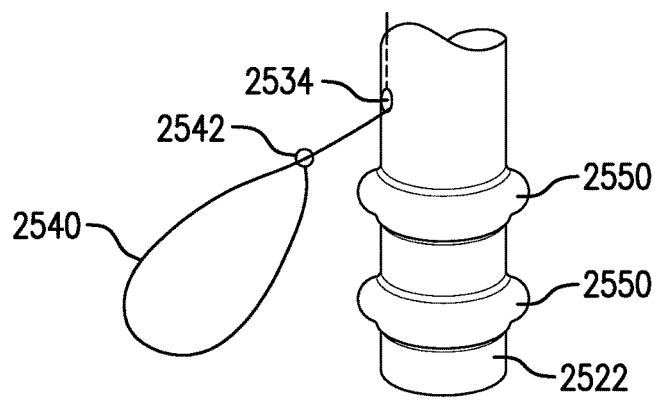
Figure 10C:
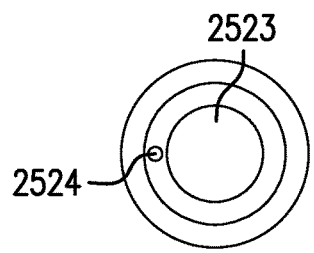

FIGS. 10A-10C show another embodiment of a sleeve delivery device 2500. FIG. 10A shows a perspective view of sleeve delivery device 2500. FIG. 10B shows an enlarged view of a distal portion of sleeve delivery device 2500. FIG. 10C shows a cross-sectional view of sleeve delivery device 2500.

Sleeve delivery device 2500 may be used to deliver a gastrointestinal sleeve. Sleeve delivery device 2500 may also be used to deliver a gastrointestinal cuff together with or apart from a gastrointestinal sleeve.

Sleeve delivery device 2500 may include a handle 2510, a delivery catheter 2520, a sealing element 2540, one or more rings 2550, and a pump 2570.

Handle 2510 may include a sealing port 2514, a pump port 2517, and a snare port 2518. Snare port 2518 is configured to receive a loop snare or other grasping device.

Delivery catheter 2520 includes a proximal portion 2521 and a distal portion 2522. Proximal portion 2521 is coupled to handle 2510. Distal portion 2522 is configured to receive a proximal portion of a gastrointestinal sleeve. Distal portion 2522 may be curved to facilitate placement into the pylorus and/or intestine. Delivery catheter 2520 includes a delivery lumen 2523 and a sealing lumen 2524. Delivery lumen 2523 is configured to receive at least a distal portion of a gastrointestinal sleeve which may be inverted inside delivery lumen 2523. Sealing lumen 2524 is in communication with a sealing opening 2534 formed in a side of distal portion 2522.

Sealing element 2540 is configured to form a substantially fluid-tight seal between a proximal portion of a sleeve, such as a gastrointestinal sleeve, and distal portion 2522 of delivery catheter 2520, when a proximal portion of a gastrointestinal sleeve is placed over distal portion 2522 of delivery catheter 2520. Sealing element 2540 is also configured to retain a gastrointestinal sleeve to delivery catheter 2520 during delivery. Sealing element 2540 may be, for example, a suture, wire, or other means that runs through sealing lumen 2524, exits out of sealing opening 2534, and wraps one or more times around a proximal portion of a gastrointestinal sleeve placed over distal portion 2522 of delivery catheter 2520. Sealing element 2540 may include a distal portion 2542 that may be tied to sealing element 2540 with a releasable knot.

Rings 2550, which may include any radially outwardly protruding structure, may be formed or coupled around distal portion 2522 of delivery catheter 2520. Rings 2550 may be coupled with heat shrink tubing, an adhesive, or other suitable methods. Rings 2550 are configured to fit inside a proximal portion of a gastrointestinal sleeve. Rings 2550 may cooperate with sealing element 2540 to help seal and retain a proximal portion of a gastrointestinal sleeve around distal portion 2522 of delivery catheter 2520.

Pump 2570 is configured to be coupled to pump port 2517. Pump 2570 is configured to pump a fluid such as water into delivery lumen 2523 to evert a gastrointestinal sleeve loaded onto delivery catheter 2520. Pump 2570 may include controls for pressure, volume, flow rate, time, or other parameters.

Figure 10D:
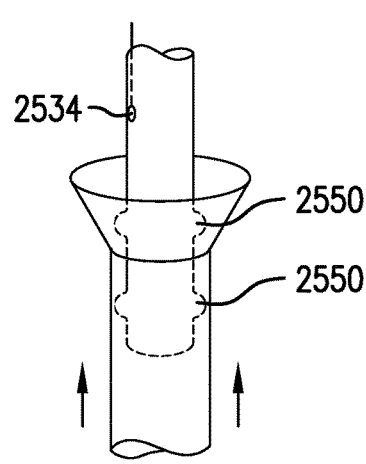
FIGS. 10D-10G show one embodiment of a method for loading sleeve delivery device 2500.
Figure 10E:
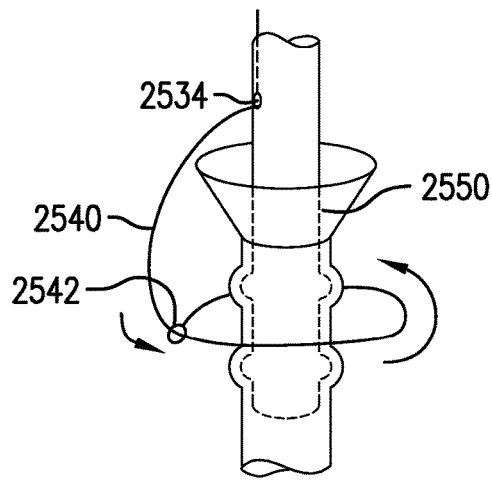
Figure 10F:
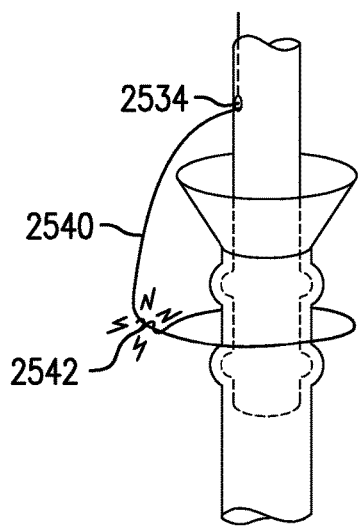
Figure 10G:
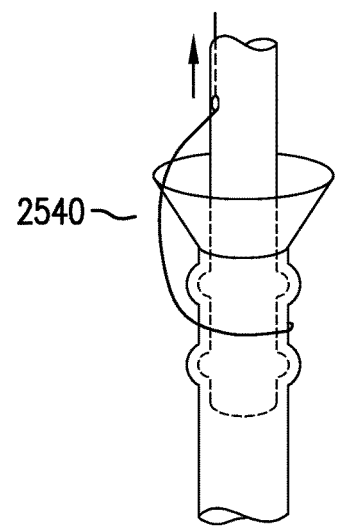

FIGS. 10D-10G show one embodiment of a method for loading sleeve delivery device 2500. FIG. 10D shows placing a proximal portion of a gastrointestinal sleeve over distal portion 2522 of delivery catheter 2520 and over rings 2550. FIG. 10E shows wrapping sealing element 2540 around the proximal portion of the gastrointestinal sleeve between two rings 2550. FIG. 10F shows securing sealing element 2540 to itself by tying a knot that will release when pulled, such as a slip knot. FIG. 10G shows tightening of sealing element 2540 around the proximal portion of the gastrointestinal sleeve. The loading may be completed by inserting a grasper, such as a loop snare, through delivery lumen 2523 and the gastrointestinal sleeve, sealing a distal portion of the gastrointestinal sleeve, and using the loop snare to pull the distal portion of the gastrointestinal sleeve into delivery lumen 2523 to invert the gastrointestinal sleeve into delivery lumen 2523. Further examples of everting systems and methods that can be used with the systems and methods disclosed herein can be found, for example, in U.S. Pat. No. 8,118,774 and U.S. Pat. Pub. No. 2007/0198074, both of which are incorporated by reference in their entireties.

Figure 11A:
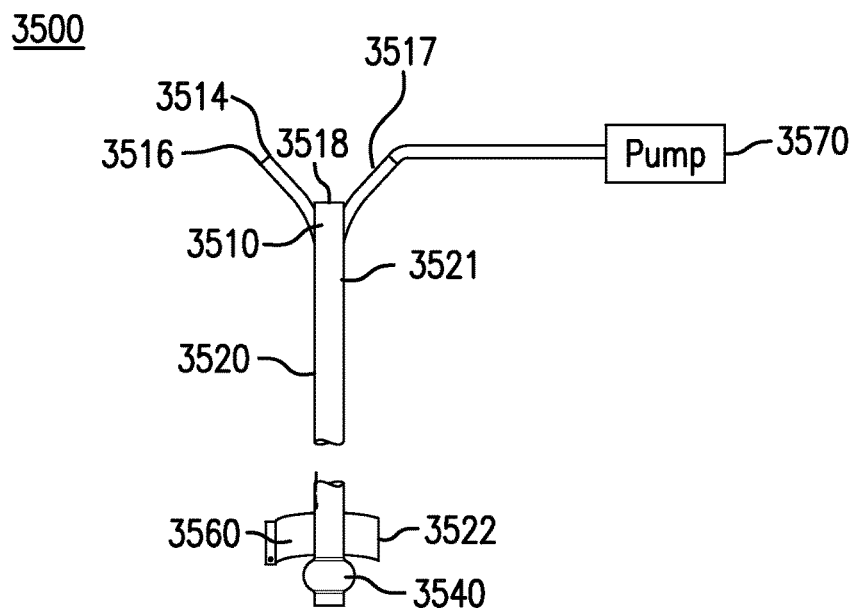
FIGS. 11A-11C show yet another embodiment of a sleeve delivery device 3500.
Figure 11B:
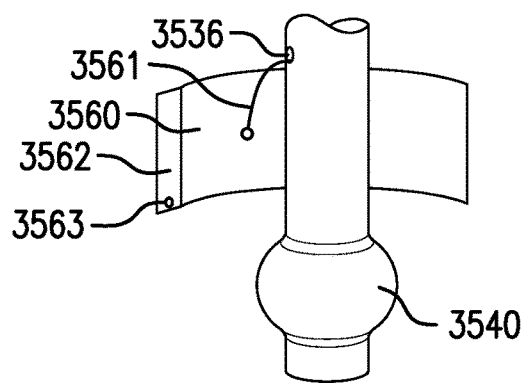
Figure 11C:
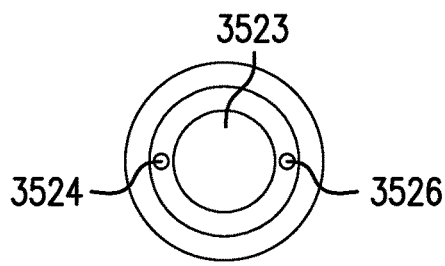

FIGS. 11A-11C show yet another embodiment of a sleeve delivery device 3500. FIG. 11A shows a perspective view of sleeve delivery device 3500. FIG. 11B shows an enlarged view of a distal portion of sleeve delivery device 3500. FIG. 11C shows a cross-sectional view of sleeve delivery device 3500.

Sleeve delivery device 3500 may be used to deliver a gastrointestinal sleeve. Sleeve delivery device 3500 may also be used to deliver a gastrointestinal cuff together with or apart from a gastrointestinal sleeve.

Sleeve delivery device 3500 may include a handle 3510, a delivery catheter 3520, a balloon 3540, a boot 3560, and a pump 3570.

Handle 3510 may include an inflation port 3514, a boot release port 3516, a pump port 3517, and a snare port 3518. Inflation port 3514 is configured to be coupled to an inflation source. Snare port 3518 is configured to receive a loop snare or other grasping device.

Delivery catheter 3520 includes a proximal portion 3521 and a distal portion 3522. Proximal portion 3521 is coupled to handle 3510. Distal portion 3522 is configured to receive a proximal portion of a gastrointestinal sleeve. Distal portion 3522 may be curved to facilitate placement into the pylorus and/or intestine. Delivery catheter 3520 includes a delivery lumen 3523, an inflation lumen 3524, and a boot release lumen 3526. Delivery lumen 3523 is configured to receive at least a distal portion of a gastrointestinal sleeve which may be inverted inside delivery lumen 3523. Inflation lumen 3524 is in communication with balloon 3540. Boot release lumen 3526 is in communication with a boot release opening 3536 formed in a side of distal portion 3522.

Balloon 3540 is coupled to distal portion 3522 of delivery catheter 3520. Balloon 3540 is configured to form a substantially fluid-tight seal between a proximal portion of a sleeve, such as a gastrointestinal sleeve, and distal portion 3522 of delivery catheter 3520, when a proximal portion of a gastrointestinal sleeve is placed over distal portion 3522 of delivery catheter 3520. Balloon 3540 is also configured to retain a gastrointestinal sleeve to delivery catheter 3520 during delivery. Balloon 3540 may be a circumferential balloon coupled around distal portion 3522 of delivery catheter 3520.

Boot 3560 is configured to wrap around a proximal portion of a gastrointestinal sleeve placed over distal portion 3522 of delivery catheter 3520. Boot 3560 is configured to prevent damage to or snagging of a proximal portion of a gastrointestinal sleeve during delivery. Boot 3560 has an outside profile configured to minimize trauma and damage to esophagus and other tissue during delivery. Boot 3560 may also help to retain a gastrointestinal sleeve to delivery catheter 3520. Boot 3560 includes a boot release 3561. Boot release 3561 may be, for example, a suture, wire, or other means that runs through boot release lumen 3526, exits out of boot release opening 3536, and attaches to boot 3560. Boot release 3561 is configured to unzip, tear open, cut, degrade, or otherwise disassociate boot 3560 to release it from delivery catheter 3520. Boot 3560 may include perforations 3562 and a tongue 3563 to facilitate release. Boot 3560 may be made of plastic, fabric, or other suitable material. When sleeve delivery device 3500 is used to deliver a gastrointestinal cuff together with a gastrointestinal sleeve, boot 3560 may be long enough to wrap around both the gastrointestinal cuff and the proximal portion of the gastrointestinal sleeve. A boot 3560 may also be used with sleeve delivery devices 1500 and 2500.

Pump 3570 is configured to be coupled to pump port 3517. Pump 3570 is configured to pump a fluid such as water into delivery lumen 3523 to evert a gastrointestinal sleeve loaded onto delivery catheter 3520. Pump 3570 may include controls for pressure, volume, flow rate, time, or other parameters.

Figure 11D:
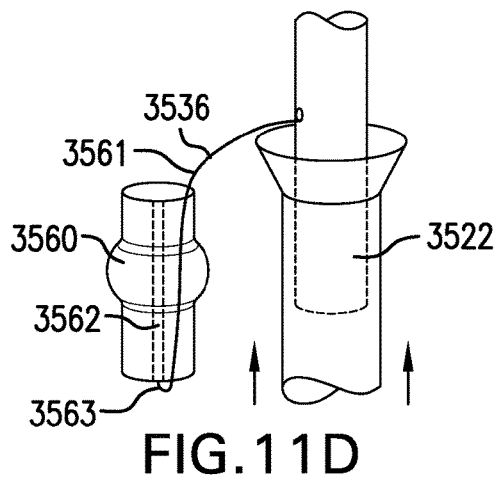
FIGS. 11D-11G show one embodiment of a method for loading sleeve delivery device 3500.
Figure 11E:
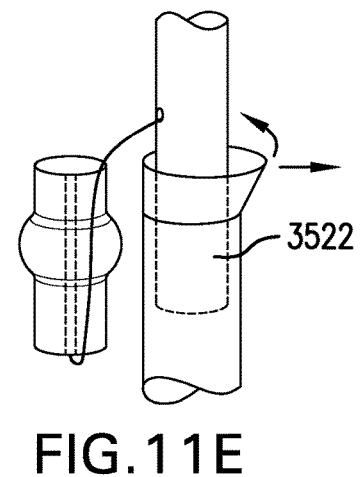
Figure 11F:
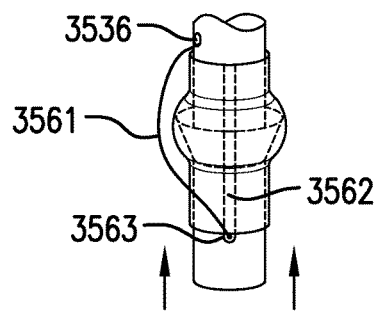
Figure 11G:
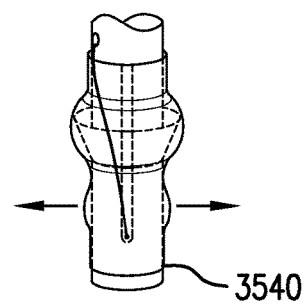

FIGS. 11D-11G show one embodiment of a method for loading sleeve delivery device 3500. FIG. 11D shows placing a proximal portion of a gastrointestinal sleeve over distal portion 3522 of delivery catheter 3520 and over balloon 3540. FIG. 11E shows folding the proximal portion of the gastrointestinal sleeve around distal portion 3522 of delivery catheter 3520. The loading may be continued by inserting a grasper, such as a loop snare, through delivery lumen 3523 and the gastrointestinal sleeve, sealing a distal portion of the gastrointestinal sleeve, and using the loop snare to pull the distal portion of the gastrointestinal sleeve into delivery lumen 3523 to invert the gastrointestinal sleeve into delivery lumen 3523. FIG. 11F shows wrapping boot 3560 around the now folded proximal portion of the gastrointestinal sleeve and attaching boot 3560 to boot release 3561. FIG. 11G shows inflating balloon 3540. Further examples of everting systems and methods that can be used with the systems and methods disclosed herein can be found, for example, in U.S. Pat. No. 8,118,774 and U.S. Pat. Pub. No. 2007/0198074, both of which are incorporated by reference in their entireties.

FIGS. 12A-12C show one embodiment of an anchor delivery device 1600. FIG. 12A shows a perspective view of anchor delivery device 1600. FIG. 12B shows an exploded view of anchor delivery device 1600. FIG. 12C shows an enlarged cross-sectional view of a distal portion of anchor delivery device 1600 with a tissue anchor loaded.

Anchor delivery device 1600 includes a handle 1610, a sheath 1650, a delivery needle 1660, and a stylet 1670.

Handle 1610 includes a needle control 1616 and a stylet control 1617.

Sheath 1650 includes a proximal portion 1651, a distal portion 1652, and a sheath lumen 1655. Proximal portion 1651 of sheath 1650 may be coupled to handle 1610. Sheath 1650 is configured to be slidably disposed in a working lumen of an endoscope.

Delivery needle 1660 is slidably disposed in sheath lumen 1655. Delivery needle 1660 includes a proximal portion 1661, a distal portion 1662, and a needle lumen 1665. Proximal portion 1661 may be coupled to needle control 1616. Distal portion 1662 may include a tip 1668 that is sharp. Alternatively, tip 1668 may be atraumatic and coupled to an RF or other energy source. Distal portion 1662 may be advanced out of and refracted into sheath 1620. Distal portion 1662 may be preformed with a curve, or made of a shape memory material. This curve may be straightened out when distal portion 1662 is retracted into sheath 1620. Distal portion 1662 may be made of the same material as the rest of delivery needle 1660. Alternatively, distal portion 1662 may be made of a different material for greater curve and/or flexibility. For example, distal portion 1662 may be made of a polyamide and the rest of delivery needle 1660 may be made of nitinol. Delivery needle 1660 is configured to receive a tissue anchor collapsed into a delivery configuration.

Stylet 1670 is slidably disposed in needle lumen 1665. Stylet 1670 includes a proximal portion 1671 and a distal portion 1672. Proximal portion 1671 may be coupled to stylet control 1617. Distal portion 1672 may be advanced out of and retracted into delivery needle 1660. Stylet 1670 is configured to push out a tissue anchor loaded in delivery needle 1660.

FIGS. 13A-13E show one embodiment of a method for using anchor delivery device 1600. Other systems and methods that can be used or modified for use with anchor delivery devices as described herein can be found, for example, in U.S. Pat. Pub. No. 2009/0012541 to Dahl et al., which is hereby incorporated by reference in its entirety.

FIG. 13A shows loading anchor delivery device 1600 with a tissue anchor, e.g., tissue anchor 1300. Tissue anchor 1300A, tissue anchor 2300, tissue anchor 3300, tissue anchor 4300, and/or any other suitable tissue anchor may also be used. Delivery needle 1660 is refracted inside sheath 1650. A distal retention element of a tissue anchor is loaded into delivery needle 1660. A proximal retention element of tissue anchor 1300 hangs outside of delivery needle 1660. A therapeutic agent, e.g., an antibiotic gel, may also be loaded into delivery needle 1660.

FIG. 13B shows advancing delivery needle 1660 through sheath 1650 and transmurally through a tissue wall W. The proximal retention element is maintained on a proximal side of the tissue wall W, e.g., on a mucosal surface. In other embodiments tissue anchor 1300 may be placed through a plication.

FIG. 13C shows advancing stylet 1640 through delivery needle 1630 to deploy the distal retention element on a distal side of the tissue wall W, e.g., on a serosal surface. The antibiotic gel may also be pushed out.

FIG. 13D shows positioning and/or turning over tissue anchor 1300 as necessary using laparoscopic instruments positioned on the distal side of the tissue wall W.

FIG. 13E shows retracting delivery needle 1660 back through the tissue wall and back into sheath 1650, leaving a tension element of tissue anchor 1300 in place through the tissue wall W.

Figure 14A:
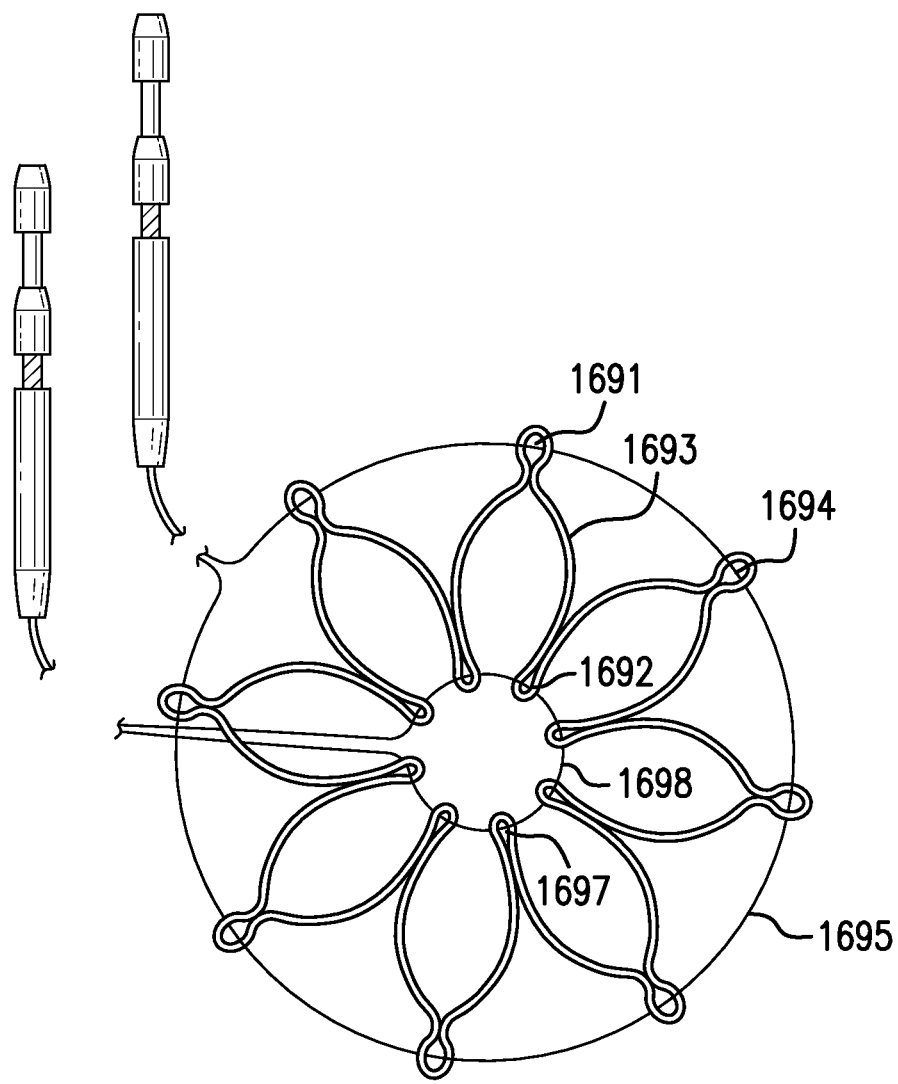
FIGS. 14A-14C show one embodiment of a stent 1690.
Figure 14B:
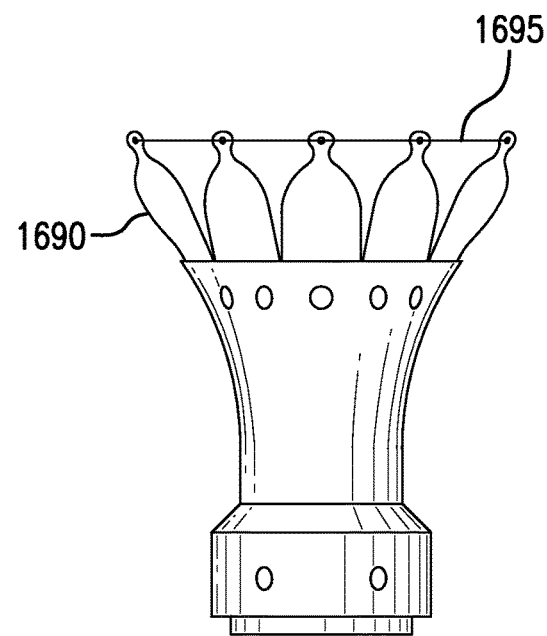
Figure 14C:
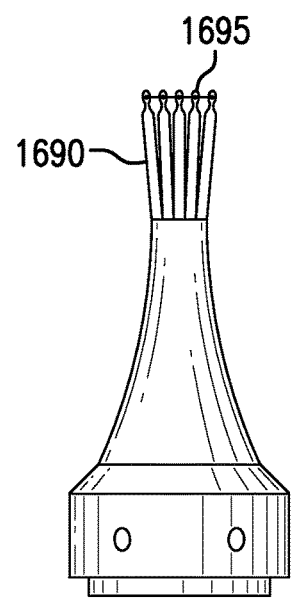

FIGS. 14A-14C show one embodiment of a stent 1690. FIG. 14A shows a top view of stent 1690. FIG. 14B shows stent 1690 in an collapsed configuration coupled to a gastrointestinal cuff. FIG. 14C shows stent 1690 in an expanded configuration coupled to a gastrointestinal cuff.

Stent 1690 may be removably coupled to a gastrointestinal cuff to create a working space inside the esophagus. Stent 1690 may also be used without being coupled to the gastrointestinal cuff. Stent 1690 may be used in conjunction with anchor delivery device 1600.

Stent 1690 includes a plurality of proximal segments 1691 and a plurality of distal segments 1692 connected by connecting segments 1693. Proximal segments 1691 may include proximal drawstring holes 1694. A proximal drawstring 1695 may be threaded through proximal drawstring holes 1692. A proximal drawstring control 1696 may be coupled to proximal drawstring 1695. Proximal drawstring control 1696 is configured to loosen and tighten proximal drawstring 1695 to expand and collapse a proximal portion of stent 1690. Distal segments 1692 may include distal drawstring holes 1697. A distal drawstring 1698 may be threaded through distal drawstring holes 1697. A distal drawstring control 1699 may be coupled to distal drawstring 1698. Distal drawstring control 1699 is configured to loosen and tighten distal drawstring to expand and collapse a distal portion of stent 1690.

Stent 1690 may be removably coupled to an inner surface of a proximal portion of a gastrointestinal cuff. Stent 1690 may be sutured to the gastrointestinal cuff. Stent 1690 may be delivered in a collapsed configuration together with the gastrointestinal cuff, and expanded at an attachment point to create a working space. When the working space is no longer needed, the sutures may be cut and removed, and stent 1690 collapsed and removed.

Stent 1690 may also be used without being coupled to a gastrointestinal cuff. Stent 1690 may be delivered in a collapsed configuration into a previously placed gastrointestinal cuff, and expanded to create a working space. When the working space is no longer needed, the stent 1690 may be collapsed and removed.

Figure 15A:
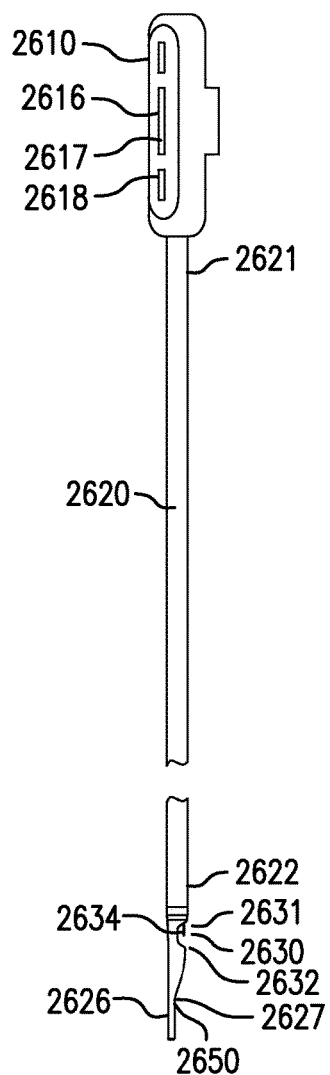
FIGS. 15A-15G show another embodiment of an anchor delivery device 2600.
Figure 15B:
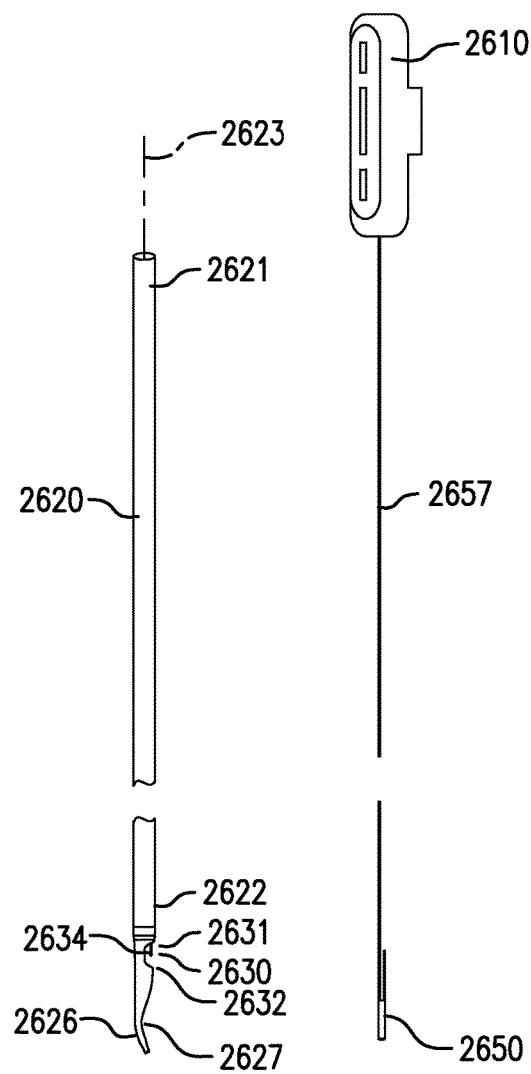
Figure 15C:
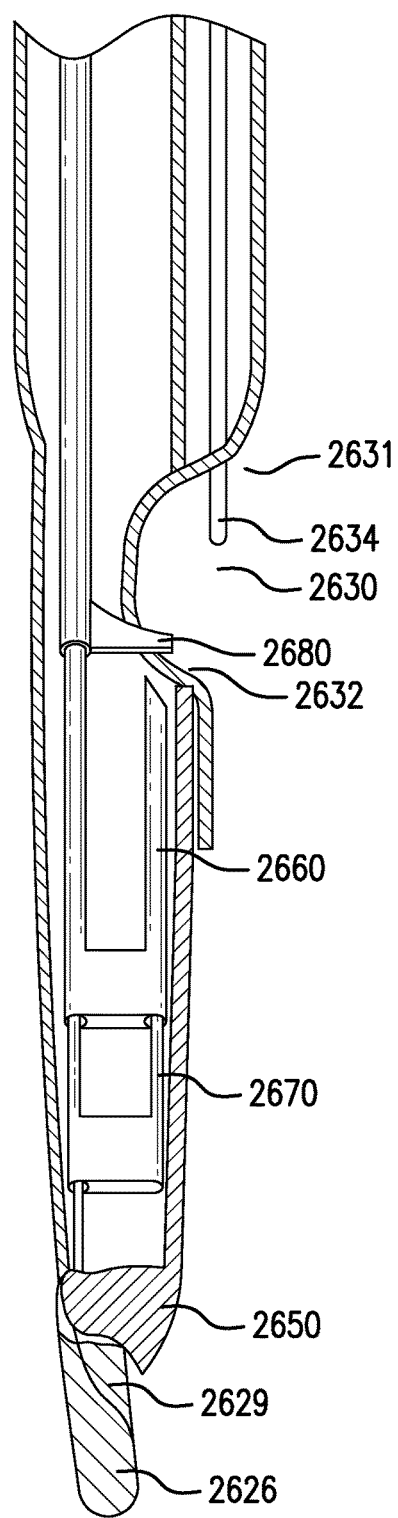
Figure 15D:
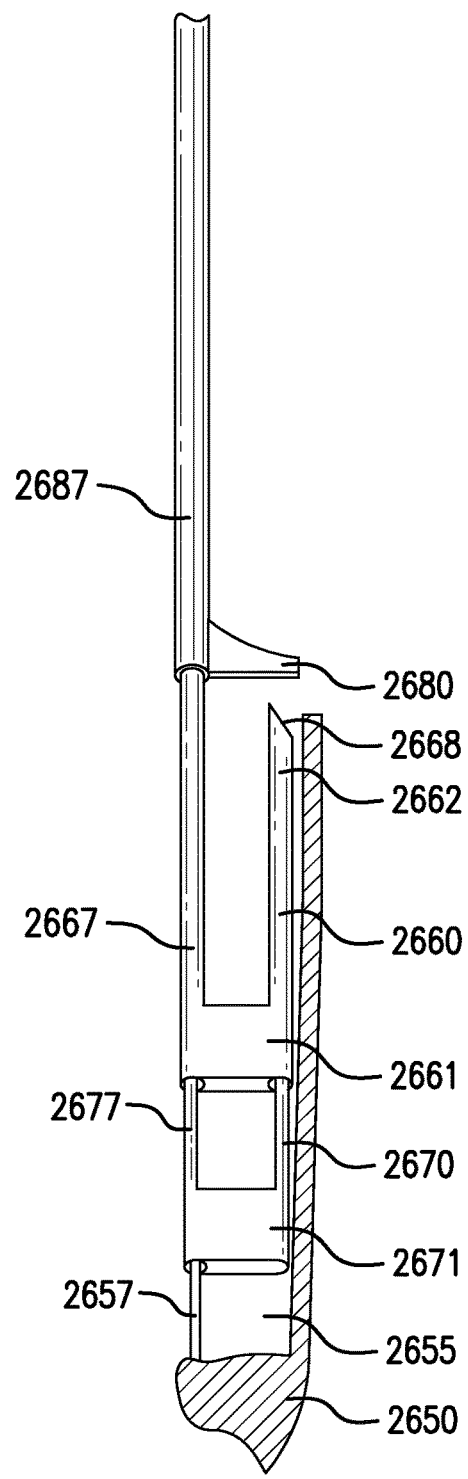
Figure 15E:
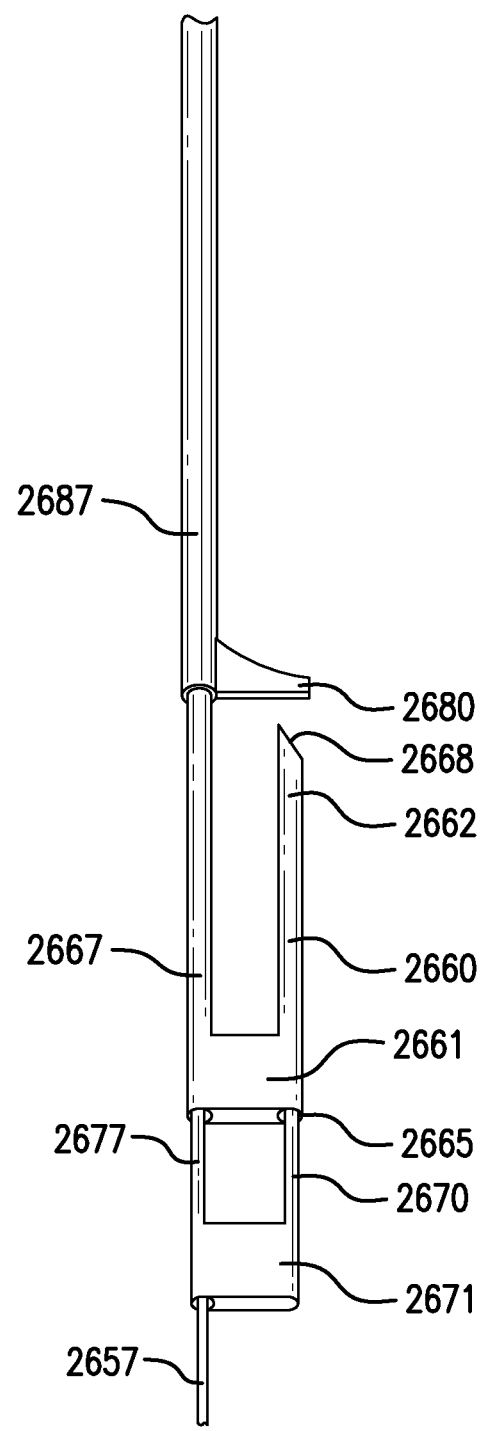
Figure 15F:
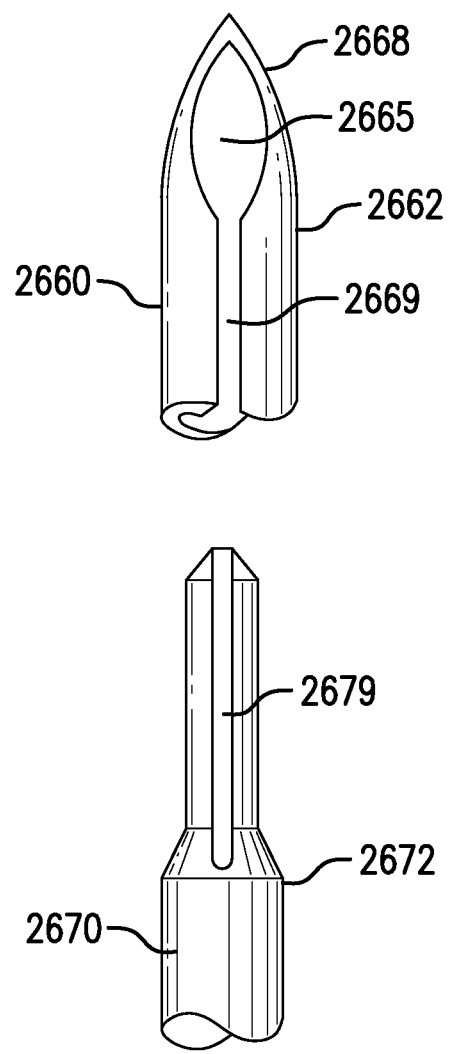
Figure 15G:
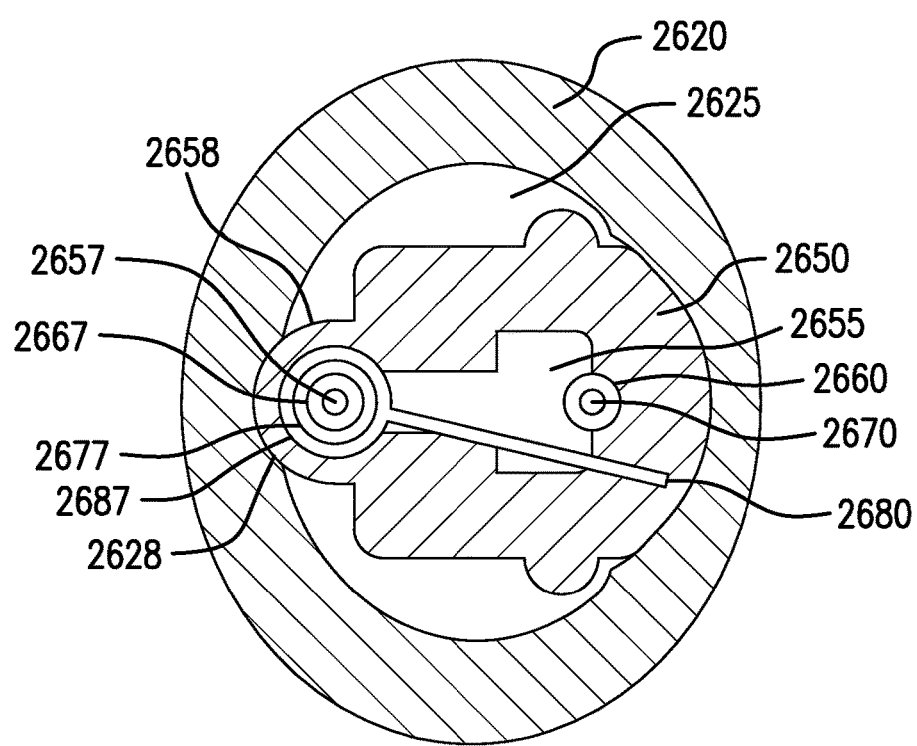

FIGS. 15A-15G show another embodiment of an anchor delivery device 2600. FIG. 15A shows a perspective view of anchor delivery device 2600. FIG. 15B shows an exploded view of anchor delivery device 2600. FIG. 15C shows a side cross-sectional view of a distal portion of anchor delivery device 2600. FIG. 15D shows a side cross-sectional view of a distal portion of sled 2650. FIG. 15E shows a side view of a delivery needle 2660, a pushrod 2670, and a holder 2680. FIG. 15F shows an enlarged view of a delivery needle 2660 and a pushrod 2670. FIG. 15G shows an end cross-sectional view of a distal portion of anchor delivery device 2600.

Anchor delivery device 2600 includes a handle 2610, a catheter 2620, a side port 2630, a sled 2650, a delivery needle 2660, pushrod 2670, and a holder 2680.

Handle 2610 includes a needle control 2616, a pushrod control 2617, and a holder control 2618.

Catheter 2620 includes a proximal portion 2621, a distal portion 2622, and a longitudinal axis 2623. Catheter 2620 also includes a central lumen 2625. Distal portion 2622 may include a nose 2626 having an opening 2627. Nose 2626 may be soft and flexible. Nose 2626 may be elongate. Nose 2626 may be curved. Opening 2627 may be configured to allow an endoscope or other tool to pass through. Distal portion 2622 may also include an alignment slot 2628 and a stop 2629.

Side port 2630 is formed in a side of distal portion 2622 of catheter 2620. Side port 2630 includes a proximal side 2631 and a distal side 2632. Side port 2630 may optionally include a tissue brace 2634 slidably disposed within a brace lumen of catheter 2620. Tissue brace 2634 may be configured to removably cover side port 2630 to prevent tissue from prematurely entering side port 2630. Side port 2630 may be coupled to a vacuum source. Side port 2630 may be configured to be placed against and draw in a tissue wall. Side port 2630 may be sized larger to allow enough of a tissue wall to be drawn in for single-wall (transmural) anchor delivery, or sized smaller for double-wall (plication) anchor delivery. For single-wall anchor delivery, side port 2630 may have a length of 10 mm to 50 mm or greater, such as a length of 20 mm to 30 mm.

Sled 2650 is slidably disposed in central lumen 2625. Sled 2650 includes a sheathing channel 2655 having a proximal opening 2656. Sled 2650 may be coupled to a sled control rod 2657 configured to move sled 2650. Sled control rod 2657 may be coupled to handle 2610. Sled 2650 may include an alignment tab 2658 which cooperates with alignment slot 2628 to align proximal opening 2656 with side port 2630. Sled 2650 may be configured to slide in central lumen 2625 distally until it reaches stop 2629. When sled 2650 has reached stop 2629, proximal opening 2656 of sheathing channel 2655 may be positioned at distal side 2632 of side port 2630. Sled 2650 may be removed from catheter 2620 for reloading.

Delivery needle 2660 is slidably disposed in sheathing channel 2655. Delivery needle 2660 includes a distal control portion 2661, a proximal delivery portion 2662, and a needle lumen 2665. Distal control portion 2661 may be coupled to a needle control rod 2667. Needle control rod 2667 may be coupled to needle control 2616. Proximal delivery portion 2662 includes a tip 2668 that is sharp. Alternatively, tip 2668 may be atraumatic and coupled to an RF or other energy source. Delivery needle 2660 has a reverse orientation, with tip 2668 pointed proximally (e.g., toward the oropharynx, when the device 2600 is deployed transesophageally via an endoscopic technique) and movable from a first, e.g., distal retracted position to a second, e.g., proximal position for delivering a tissue anchor across a body luminal wall. Proximal delivery portion 2662 may be advanced out of and retracted into sheathing channel 2655. When advanced out of sheathing channel 2655, proximal delivery portion 2662 may enter distal side 2632 of side port 2630. Delivery needle 2660 is configured to receive a tissue anchor collapsed into a delivery configuration. Delivery needle 2660 may include a slot 2669 configured to allow a tension element of a tissue anchor to pass through.

Pushrod 2670 is slidably disposed in needle lumen 2664. Pushrod 2670 includes a distal control portion 2671 and a proximal delivery portion 2672. Distal control portion 2671 may be coupled to a pushrod control rod 2677. Pushrod control rod 2677 may be coupled to pushrod control 2617. Pushrod 2670 has a reverse orientation, with proximal delivery portion 2672 pointed proximally. Proximal delivery portion 2672 may be advanced out of and retracted into delivery needle 2660. Pushrod 2670 is configured to push out a tissue anchor loaded in delivery needle 2660. Pushrod 2670 may include at least a portion, e.g., proximal delivery portion 2672, sized small enough to push against a hub of a tissue anchor without damaging the tissue anchor or a portion thereof, e.g., the petals. Pushrod 2670 may include a channel 2679 configured to allow a tension element of a tissue anchor to pass through. Channel 2679 of pushrod 2670 may be aligned with slot 2669 of delivery needle 2660.

Holder 2680 may be coupled to a holder control rod 2687. Holder control rod 2687 may be coupled to holder control 2618. Holder 2680 may be configured to hold an anchor hole of a gastrointestinal cuff over proximal opening 2656 of sheathing channel 2655. Holder 2680 may be configured to hold an anchor hole of a gastrointestinal cuff over tip 2668 of delivery needle 2660. Holder 2680 may be slidably and/or rotatably manipulated. Holder 2680 may be stowed when not in use.

The control rods may be arranged coaxially. For example, sled control rod 2657 may be slidably disposed in a hollow pushrod control rod 2677, which is slidably disposed in a hollow needle control rod 2667, which is slidably disposed in a hollow holder control rod 2687, as shown in FIG. 15G. As another example, pushrod control rod 2677 may be slidably disposed in a hollow needle control rod 2667, which is slidably disposed in a hollow sled control rod 2657, which is slidably disposed in a hollow holder control rod 2687. Alternatively, the control rods may be arranged non-coaxially, such as in a multi-lumen carrier tube. In some embodiments, anchor delivery device 2600 may also include an integrated vacuum port operably connected to a source of vacuum. In some embodiments, the vacuum may be delivered via a port on a separate endoscope or other device.

FIGS. 16A-16F show one embodiment of a method for using anchor delivery device 2600. Sheathing lumen 2655 is represented by the cross-hatched area. For clarity, only delivery needle 2660 and pushrod 2670 are shown.

Figure 16A:
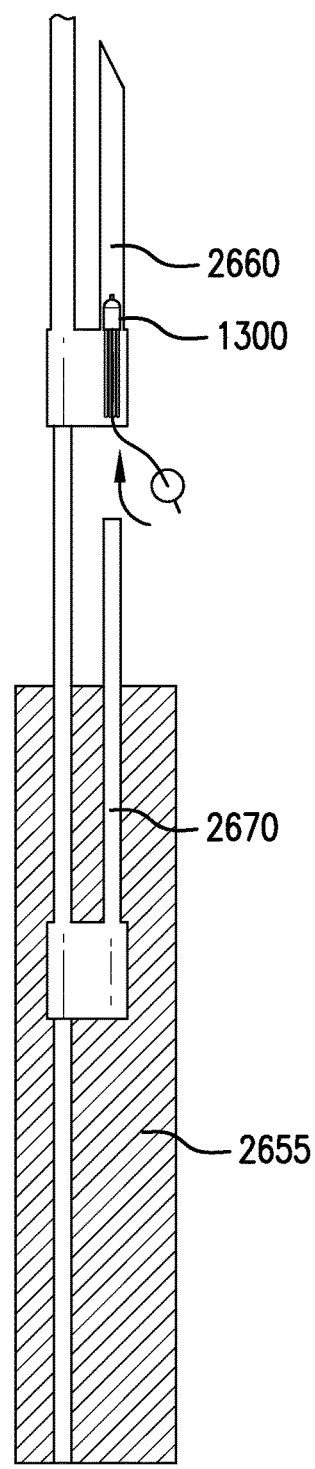
FIGS. 16A-16F show one embodiment of a method for using anchor delivery device 2600.

FIG. 16A shows loading delivery needle 2660. Sled 2650 is removed from catheter 2620. Pushrod 2670 is taken out of delivery needle 2660. An antibiotic gel may be loaded into delivery needle 2660, which may reduce the likelihood of infection when delivery needle 2660 bridges non-sterile and sterile fields. A distal retention element of a tissue anchor, e.g., tissue anchor 1300, is loaded through distal control portion 2661. Tissue anchor 1300A, tissue anchor 2300, tissue anchor 3300, tissue anchor 4300, and/or any other suitable tissue anchor may also be used. A tension element of tissue anchor 1300 is passed through slot 2669 and channel 2679. A proximal retention element is positioned outside of delivery needle 2660.

Figure 16B:
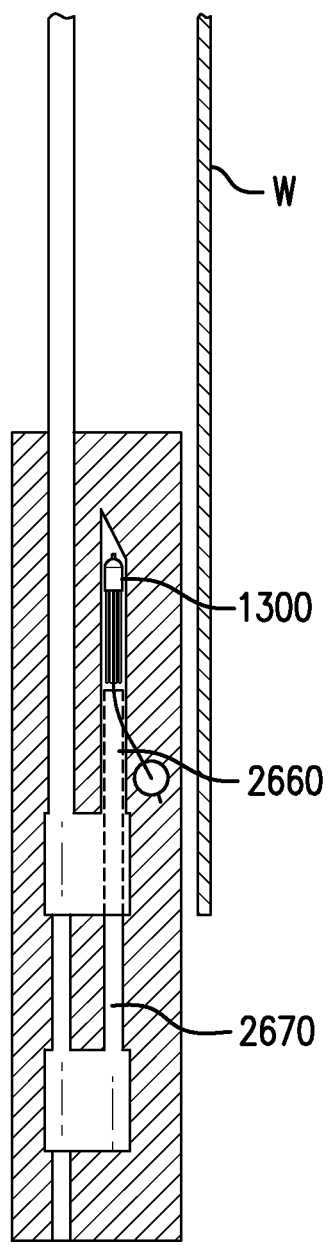

FIG. 16B shows loading catheter 2620. Pushrod 2670 is inserted into delivery needle 2660. The distal retention element is positioned inside tip 2668. Sled 2650 is inserted into catheter 2620 and seated in distal portion 2622. Proximal opening 2656 of sheathing channel 2655 is positioned at distal side 2632 of side port 2630.

Figure 16C:
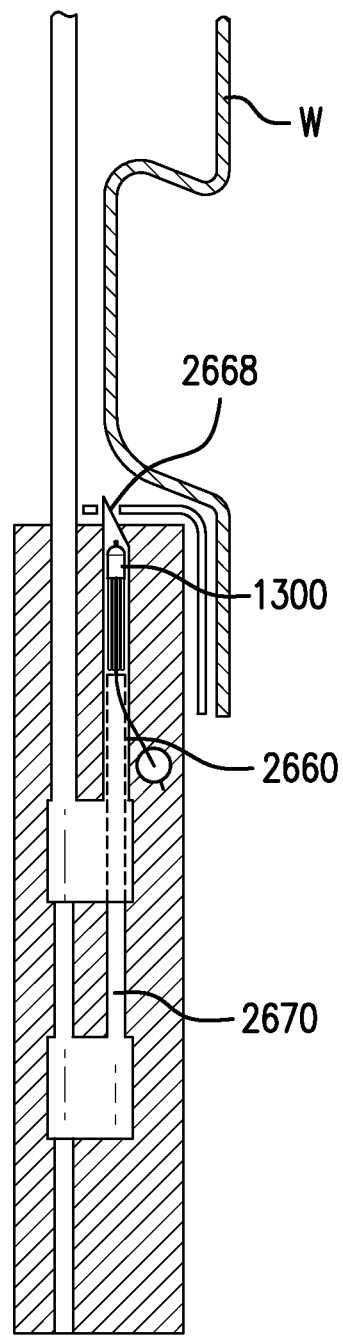

FIG. 16C shows capturing the gastrointestinal cuff. Holder 2680 may be used to hold an anchor hole of the gastrointestinal cuff over proximal opening 2656 of sheathing channel 2655. Delivery needle 2660 may be advanced a small amount so that tip 2668 threads through the anchor hole. A tissue wall W is drawn in through side port 2630 using a vacuum source. The tissue wall W at proximal side 2631 of side port 2630 may be at least partially drawn up into central lumen 2625 of catheter 2620. Tissue marks made previously, such as those made by tissue marking device 1400 and/or tissue marking device 2400, may be used to position delivery needle 2660.

Figure 16D:
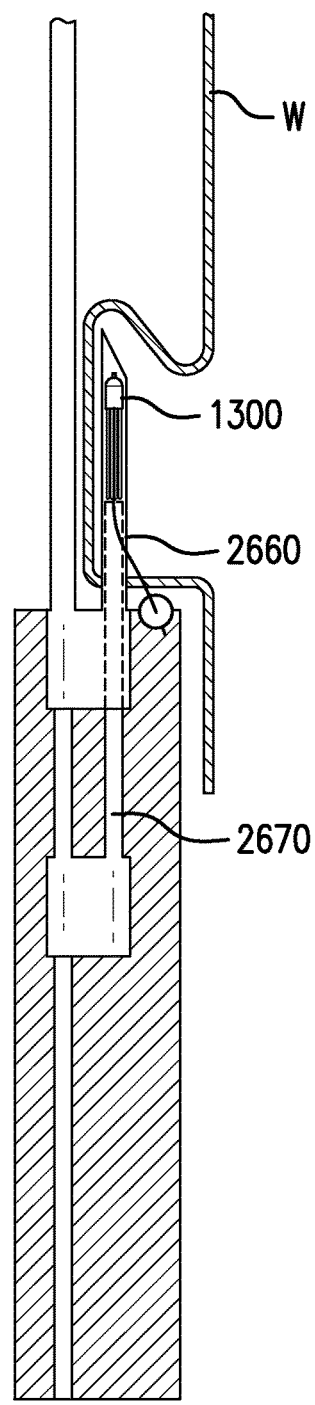

FIG. 16D shows advancing delivery needle 2660. Delivery needle 2660 is advanced through the tissue wall W at distal side 2632 of side port 2630. Pushrod 2670 is also advanced, but is not moved relative to delivery needle 2660. Handle 2610 and needle control 2616 may be configured to preset the distance delivery needle 2660 is advanced to reduce the risk of penetrating the tissue wall W through proximal side 2631 of side port 2630.

Figure 16E:
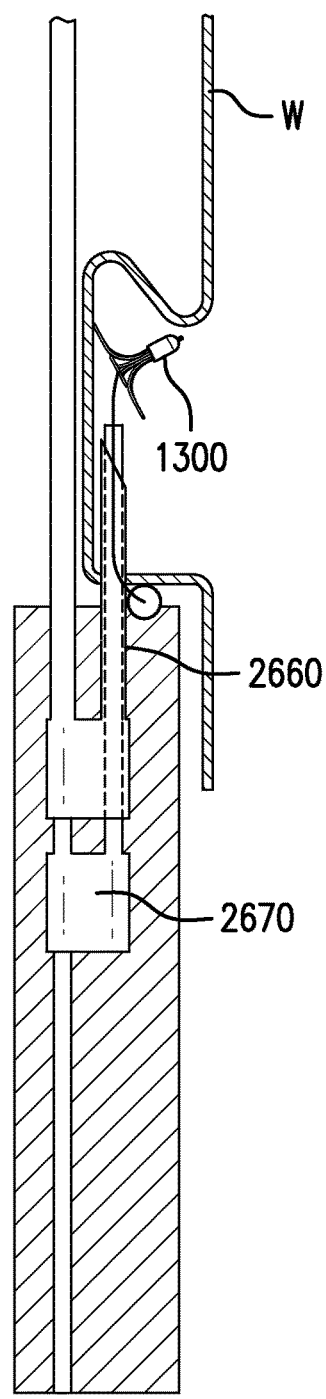

FIG. 16E shows retracting the delivery needle 2660. Delivery needle 2660 is retracted while keeping pushrod 2670 in place to deploy the distal retention element. The antibiotic gel may also be released.

Figure 16F:
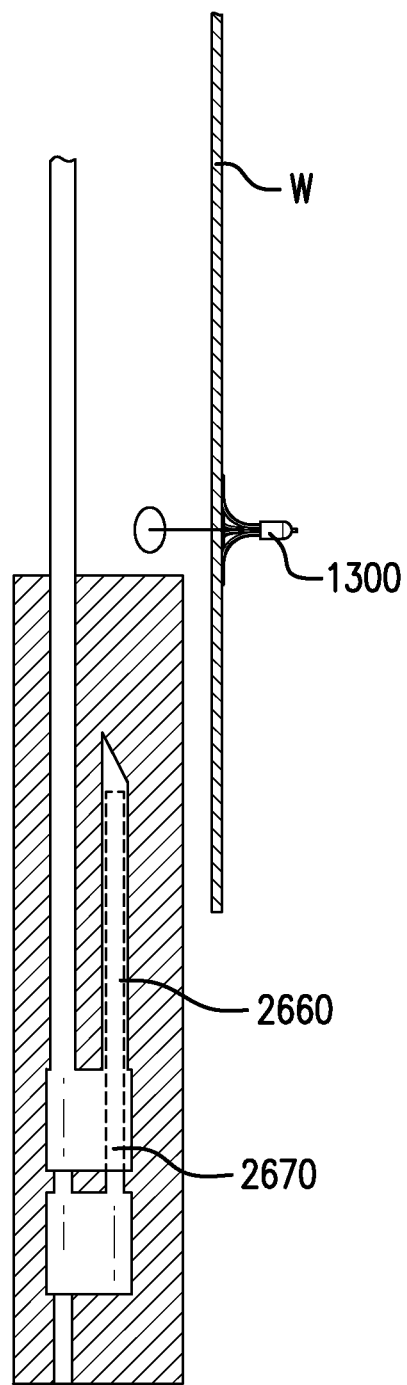

FIG. 16F shows stowing delivery needle 2660 and pushrod 2670. Delivery needle 2660 and pushrod 2670 are retracted into sheathing channel 2655. Anchor delivery device 2600 includes a delivery needle 2660 with a reverse throw, which makes it convenient for use with anchor holes on a proximal portion of a gastrointestinal cuff. The reverse throw avoids the need to draw more of the gastrointestinal cuff into side port 2630. This and other anchor delivery systems and methods used herein can be used to accurately deliver one or a plurality of tissue anchors through a single transmural wall or to create or reinforce one or a plurality of tissue plications. Furthermore, anchor delivery system 2600 may advantageously reduce the risk of puncturing other body structures in close proximity, e.g., the aorta. In some embodiments, anchor delivery systems as described herein can be used via a pure endoscopic approach, e.g., as illustrated in connection with FIGS. 18A-18J below, without necessarily requiring laparoscopic assistance.

FIGS. 17A-17H show one embodiment of a method for implanting a gastrointestinal bypass device 1000. The method may also be used with other gastrointestinal bypass devices such as gastrointestinal bypass device 2000 and gastrointestinal bypass device 3000.

Sleeve delivery device 1500 is mounted with cuff 1100 and sleeve 1200. Sleeve delivery device 2500 or sleeve delivery device 3500 may also be used. Stent 1690 is coupled to cuff 1100. Stent 1690 is cinched around sleeve delivery device 1500.

Figure 17A:
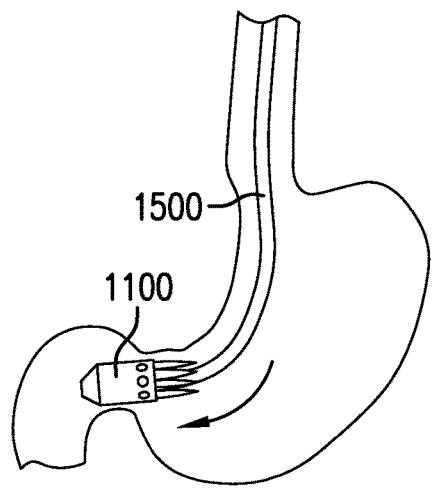
FIGS. 17A-17H show one embodiment of a method for implanting a gastrointestinal bypass device 1000.

FIG. 17A shows introducing sleeve delivery device 1500. Sleeve delivery device 1500 may position sleeve 1200 at or near the pylorus. Sleeve delivery device 1500 may be introduced with or without an overtube. An endoscope may be used for guidance and visualization.

Figure 17B:
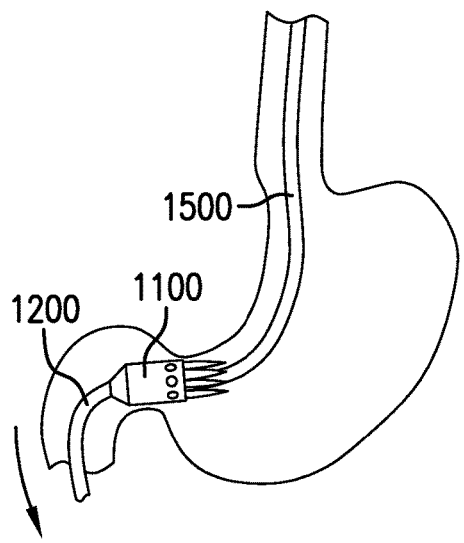

FIG. 17B shows deploying sleeve 1200. A fluid is pumped into delivery device 1500 to evert sleeve 1200 past the pylorus and into the intestine.

Figure 17C:
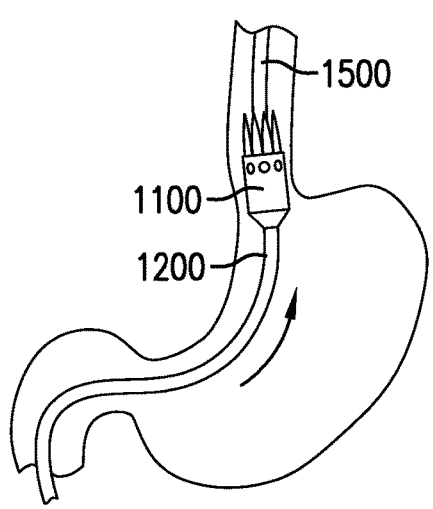

FIG. 17C shows positioning cuff 1100 and sleeve 1200 at the attachment point. Sleeve delivery device 1500 pulls cuff 1100 and sleeve 1200 proximally up to the gastroesophageal junction or other attachment points, some of which are described elsewhere in the application.

Figure 17D:
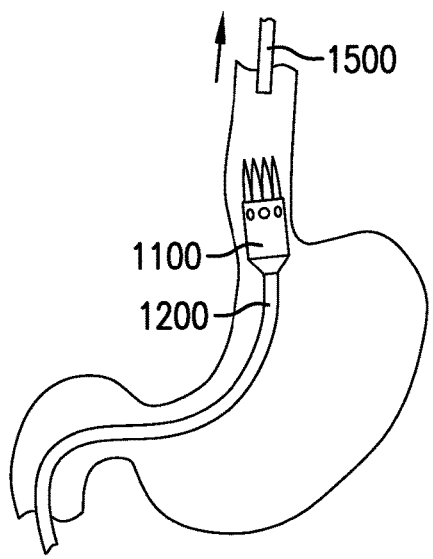

FIG. 17D shows releasing cuff 1100 and sleeve 1200 from sleeve delivery device 1500. Sleeve delivery device 1500 is then withdrawn.

Figure 17E:
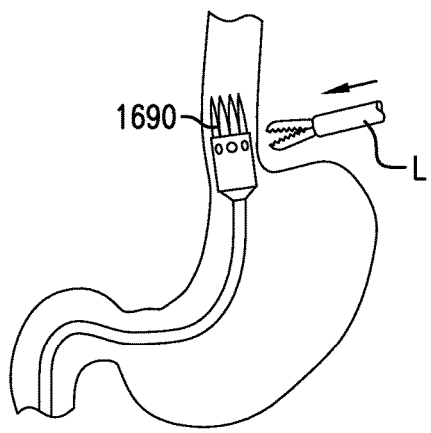

FIG. 17E shows introducing a laparoscopic tool L. Laparoscopic tool L is positioned on a distal side of the attachment point. Laparoscopic tool L may be used to clear tissue around the esophagus to create a working space.

Figure 17F:
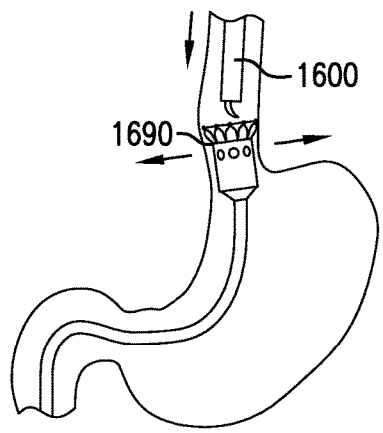

FIG. 17F shows introducing anchor delivery device 1600. Anchor delivery device 1600 may be used in the working lumen of an endoscope. Anchor delivery device 1600 may be introduced with or without an overtube. Anchor delivery device 1600 is positioned on a proximal side of the attachment point. Stent 1690 is opened to create a working space.

Figure 17G:
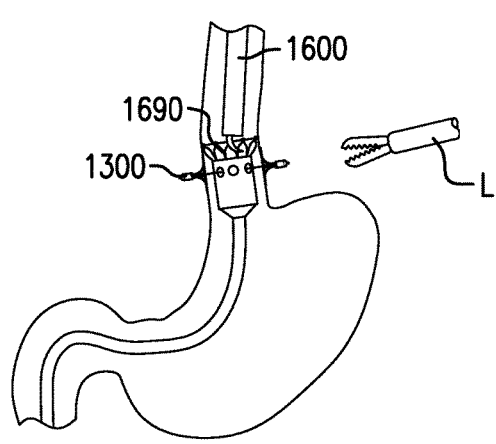

FIG. 17G shows delivering tissue anchors 1300. Anchor delivery device 1600 is delivers tissue anchors 1300 through cuff 1100 and the wall of the esophagus. Tissue anchor 1300A, tissue anchor 2300, tissue anchor 3300, tissue anchor 4300, and/or any other suitable tissue anchor may also be used. Tissue marks made earlier by tissue marking device 1400 may be used as a guide. Laparoscopic tool L may be held against the distal side of the attachment point to reduce tenting. Laparoscopic tool L may be used to flip over distal retention element 1320 of tissue anchor 1300.

Figure 17H:
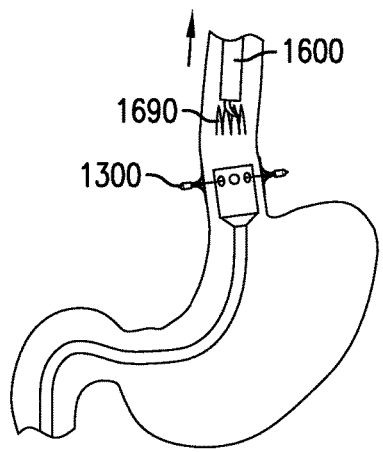

FIG. 17H shows removing stent 1690 from cuff 1100. The sutures used to couple stent 1690 to cuff 1100 may be cut and removed. Stent 1690 may be cinched using proximal drawstring 1695 and/or distal drawstring 1698 and removed. Stent 1690 may be removed with or without an overtube.

FIGS. 18A-18J show yet another embodiment of a method for implanting a gastrointestinal bypass device 3000. The method may also be used with gastrointestinal bypass device 1000 and gastrointestinal bypass device 2000.

Sleeve delivery device 1500 is mounted with cuff 3100 and sleeve 3200. Sleeve delivery device 2500 or sleeve delivery device 3500 may also be used.

Figure 18A:
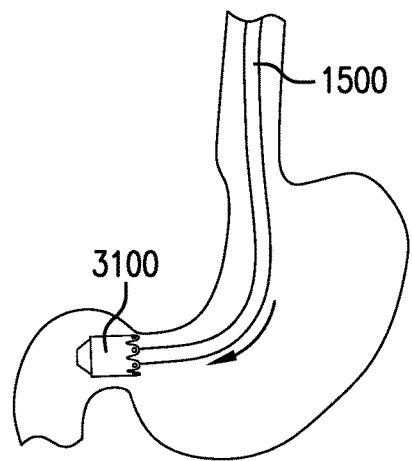
FIGS. 18A-18J show one embodiment of a method for implanting a gastrointestinal bypass device 3000.

FIG. 18A shows introducing sleeve delivery device 1500. Sleeve delivery device 1500 may position sleeve 3200 at or near the pylorus. Sleeve delivery device 1500 may be introduced with or without an overtube. An endoscope may be used for guidance and visualization.

Figure 18B:
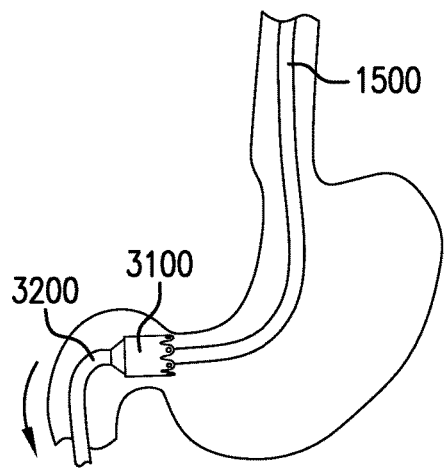

FIG. 18B shows deploying sleeve 3200. A fluid is pumped into delivery device 1500 to evert sleeve 3200 past the pylorus and into the intestine.

Figure 18C:
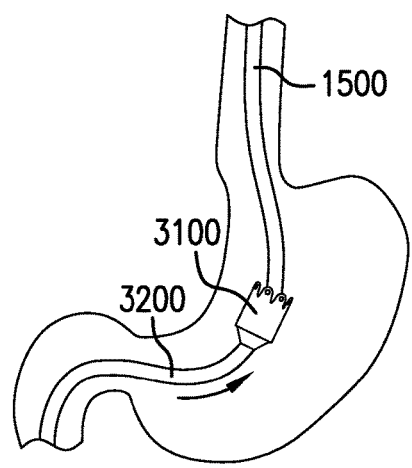

FIG. 18C shows positioning cuff 3100 and sleeve 3200 in the stomach. Sleeve delivery device 1500 pulls cuff 3100 and sleeve 3200 into the stomach.

Figure 18D:
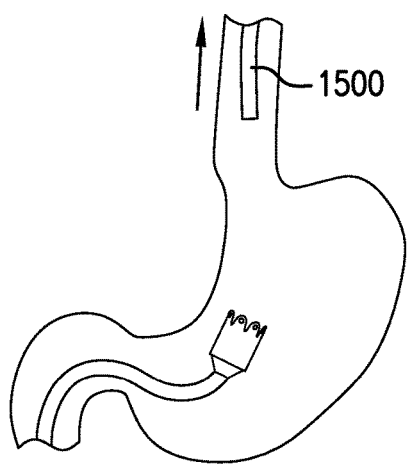

FIG. 18D shows releasing cuff 3100 and sleeve 3200 from sleeve delivery device 1500. Sleeve delivery device 1500 is then withdrawn.

Figure 18E:
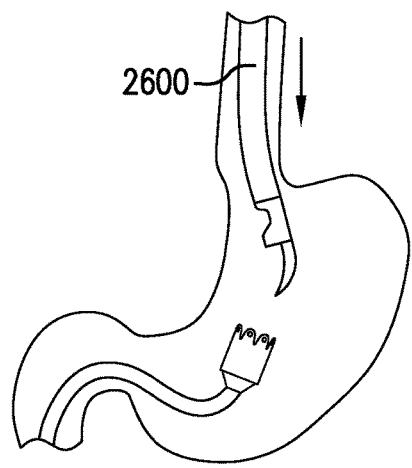

FIG. 18E shows introducing catheter 2620 of anchor delivery device 2600. Catheter 2260 of anchor delivery device 2600 is introduced through the esophagus. An endoscope may be used for guidance and visualization.

Figure 18F:
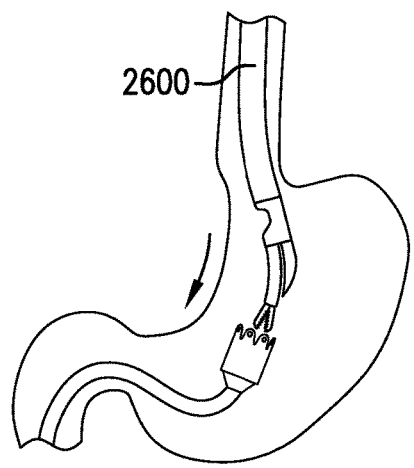

FIG. 18F shows grasping cuff 3100. A grasping tool is introduced through catheter 2260 to grasp cuff 3100 and pull cuff 3100 over catheter 2260. Sled 2650 is introduced into catheter 2260 and used to hold cuff 3100.

Figure 18G:
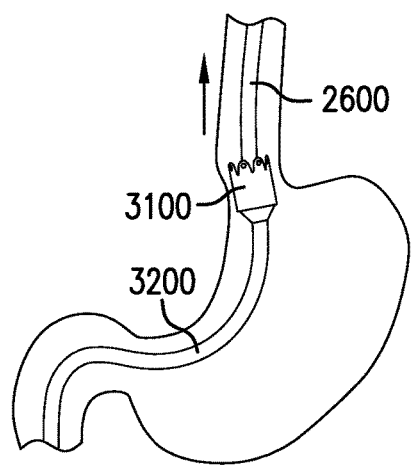

FIG. 18G shows positioning cuff 3100 and sleeve 3200 at an attachment point. Catheter 2620 pulls cuff 3100 and sleeve 3200 proximally up to the gastroesophageal junction or other attachment points, some of which are described elsewhere in the application.

Figure 18H:
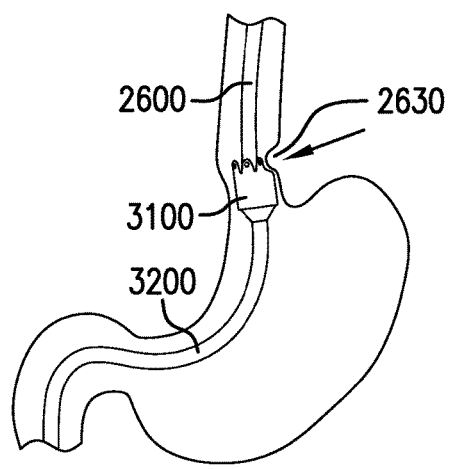

FIG. 18H shows drawing a portion of a tissue wall into side port 2630 of anchor delivery device 2620. A vacuum may be applied through the working lumen of an endoscope placed in central lumen 2625.

Figure 18I:
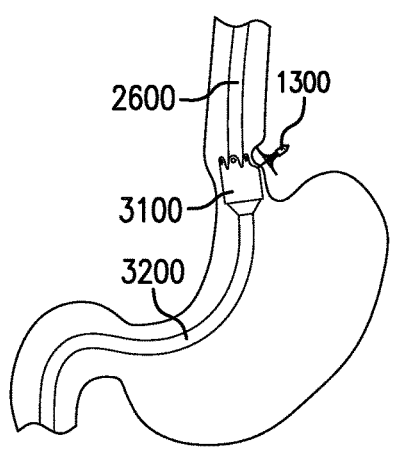

FIG. 18I shows delivering tissue anchor 1300. Anchor delivery device 2600 is used to deliver tissue anchors 1300 through cuff 3100 and the wall of the esophagus. Tissue anchor 1300A, tissue anchor 2300, tissue anchor 3300, tissue anchor 4300, and/or any other suitable tissue anchor may also be used. Tissue marks made earlier by tissue marking device 1400 may be used as a guide.

Figure 18J:
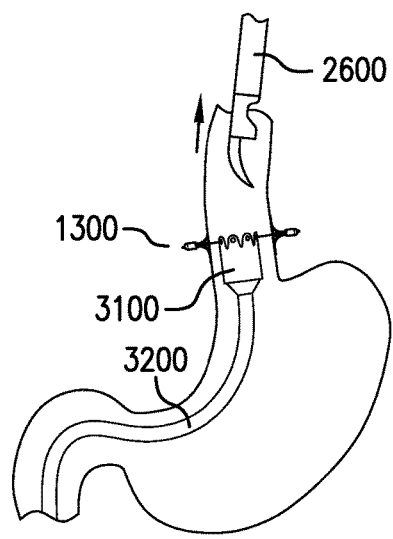

FIG. 18J shows removing anchor delivery device 2600.

Alternatively, the method may include first deploying sleeve 3200 without cuff 3100, then anchoring cuff 3100 at the attachment point, and then grasping sleeve 3200 to attach sleeve 3200 to cuff 3100.

FIGS. 25A-25D show various embodiments of attachment points which may be used with the devices and methods described above. Tissue anchors may be delivered through a wall of the esophagus at an attachment point to retain a gastrointestinal bypass device. The size and relative locations of the opening O of the stomach S, the squamocolumnar junction SCJ, the diaphragm D, and the lower esophageal sphincter LES may vary from patient to patient, and one or more of these anatomical features may be referenced separately or in combination to select an attachment point.

Figure 25A:
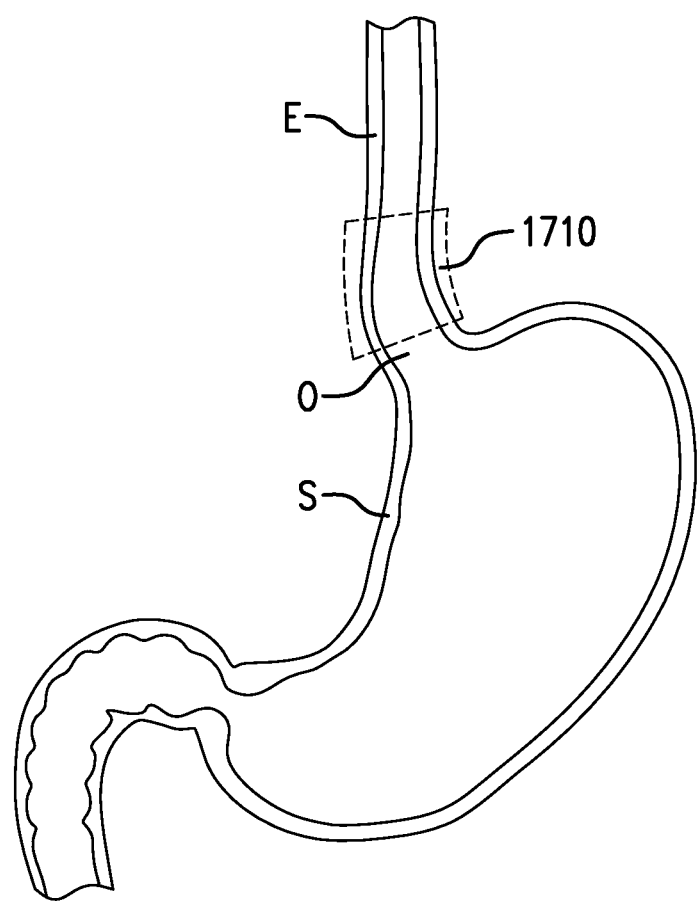
FIGS. 25A-25D show various embodiments of attachment points which may be used with the devices and methods described above. Tissue anchors may be passed through the attachment points to retain a gastrointestinal bypass device.

FIG. 25A shows one embodiment of an attachment point 1710. The esophagus E and the opening O of the stomach S are shown. Attachment point 1710 may be approximately 5 mm to approximately 25 mm above the opening O of the stomach S.

Figure 25B:
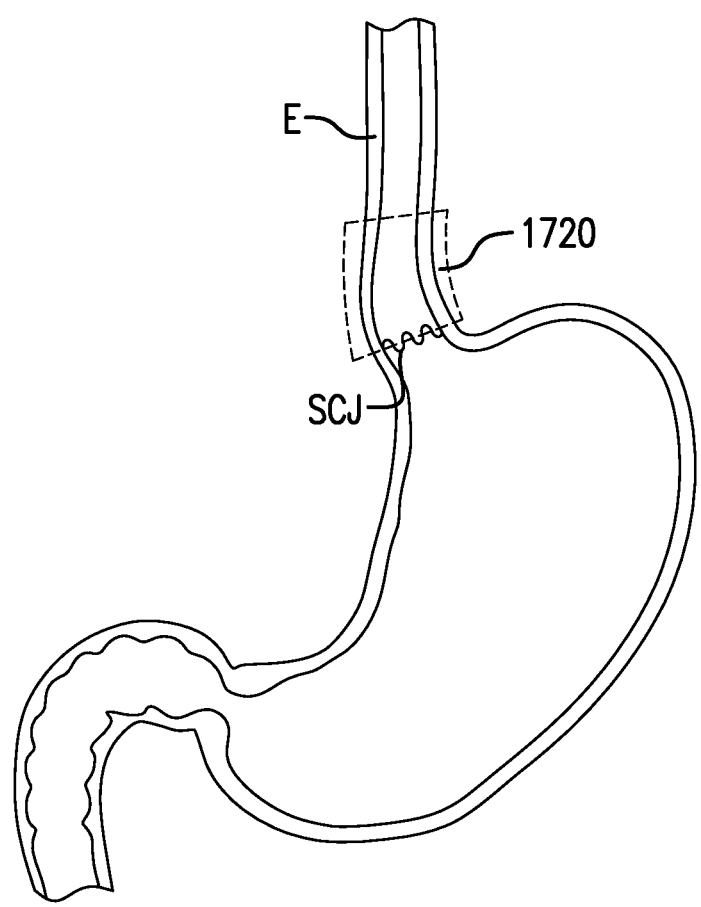

FIG. 25B shows another embodiment of an attachment point 1720. The esophagus E and the squamocolumnar junction SCJ, also known as the Z-line, are shown. Attachment point 1720 may be approximately 0 mm to approximately 20 mm above the squamocolumnar junction SCJ.

Figure 25C:
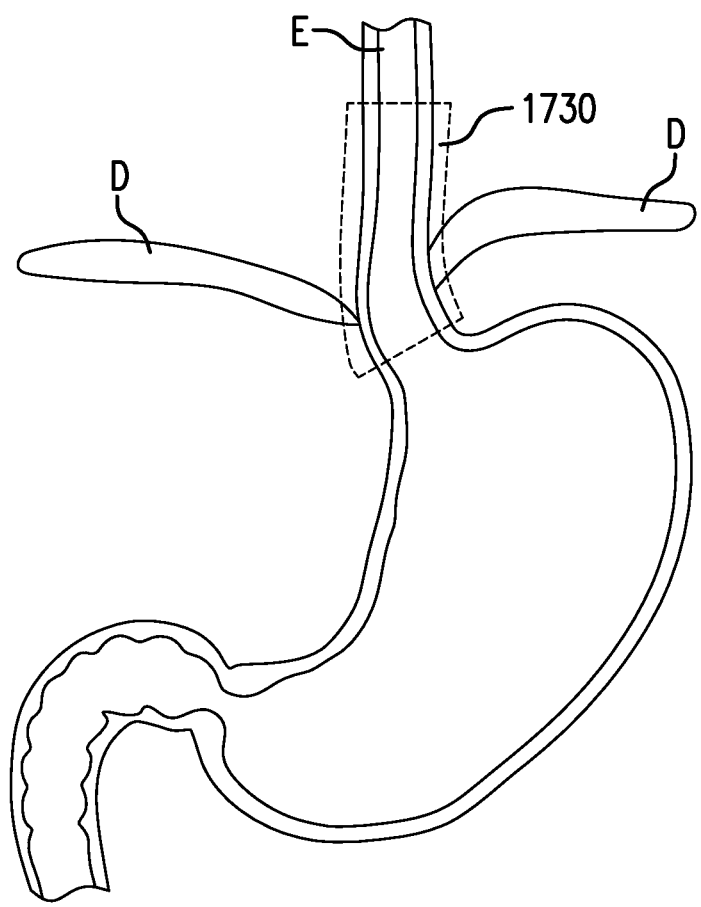

FIG. 25C shows yet another embodiment of an attachment point 1730. The esophagus E and the diaphragm D are shown. Attachment point 1730 may be approximately 20 mm below to approximately 50 mm above the diaphragm D. The diaphragm D may be located using imaging techniques and/or other methods before and/or during the delivery of the tissue anchors. The diaphragm D may be located by locating the diaphragmatic pinch in the esophagus E.

Figure 25D:
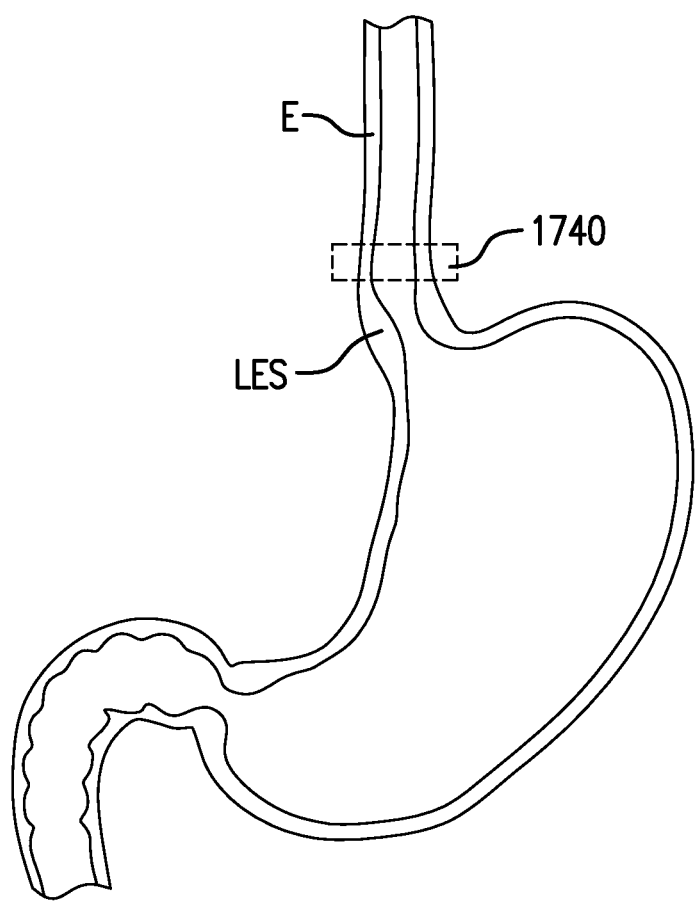

FIG. 25D shows still another embodiment of an attachment point 1740. The esophagus E and the lower esophageal sphincter LES are shown. Attachment point 1740 may be at an upper or proximal portion of the lower esophageal sphincter LES.

FIGS. 19A-19F show one embodiment of a method for exchanging a sleeve 2200. The method may also be used for exchanging a sleeve 3200. In some embodiments, anchor delivery device 2600 may be used to replace tissue anchors 1300, such as those that may have pulled out of tissue, without necessarily requiring exchange of sleeve 3200 and/or cuff 3100.

Figure 19A:
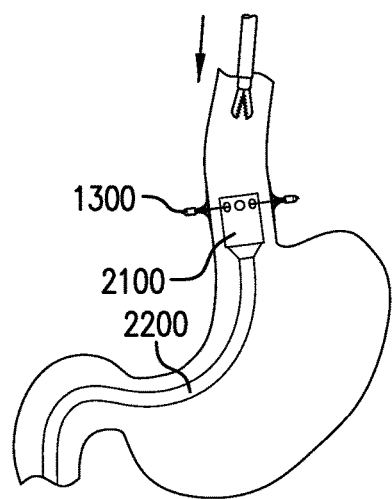
FIGS. 19A-19H show one embodiment of a method for exchanging a sleeve 2200 of a gastrointestinal bypass device 2000.

FIG. 19A shows a cuff 2100 and a sleeve 2200 implanted in an esophagus. A grasping tool is introduced into the esophagus.

Figure 19B:
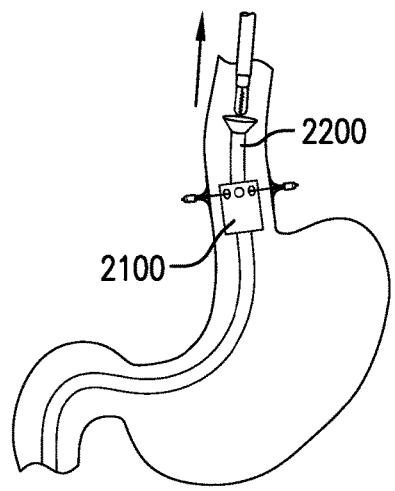

FIG. 19B shows removing sleeve 2200. The grasping tool passes through cuff 2100 to grasp sleeve 2200. The grasping tool may be configured to pull drawstring 2241 to cinch ring 2240 of sleeve 2200. Halo 2260 or attachment elements 3260 may be cut. Sleeve 2200 is pulled out.

Figure 19C:
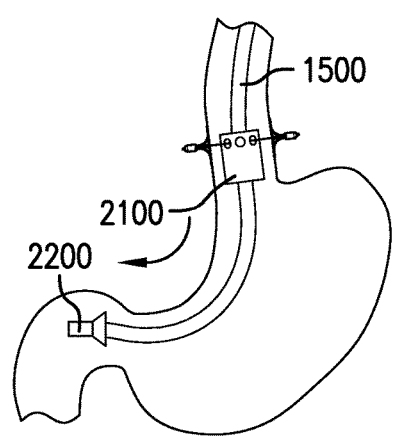

FIG. 19C shows introducing sleeve delivery device 1500. Sleeve delivery device 1500 passes through cuff 2100 and may position sleeve 2200 at or near the pylorus. Sleeve delivery device 1500 may be introduced with or without an overtube. Sleeve delivery device 2500 or sleeve delivery device 3500 may also be used. An endoscope may be used for guidance and visualization.

Figure 19D:
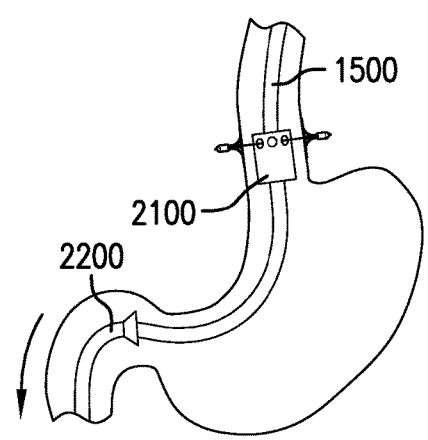

FIG. 19D shows deploying sleeve 2200. A fluid is pumped into delivery device 1500 to evert sleeve 2200 past the pylorus and into the intestine.

Figure 19E:
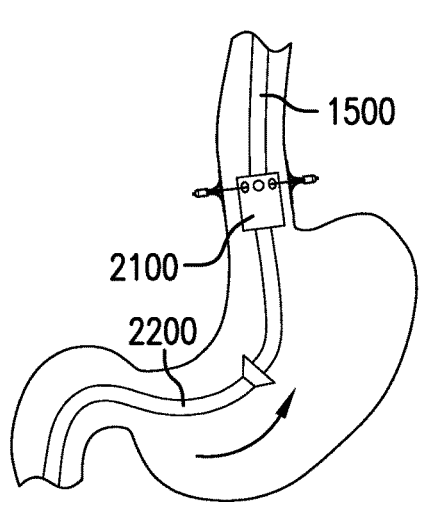

FIG. 19E shows positioning sleeve 2200 in the stomach. Sleeve delivery device 1500 pulls sleeve 2200 into the stomach.

Figure 19F:
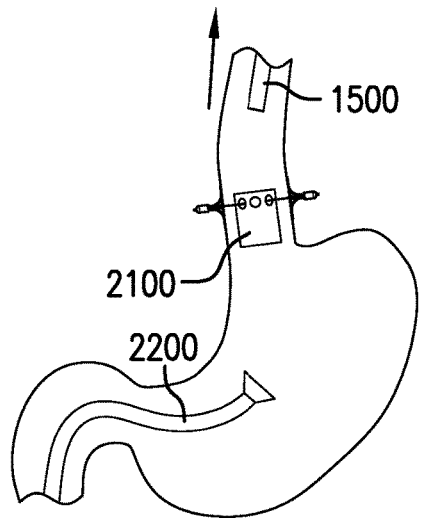

FIG. 19F shows releasing sleeve 2200 from sleeve delivery device 1500. Sleeve delivery device 1500 is then withdrawn.

Figure 19G:
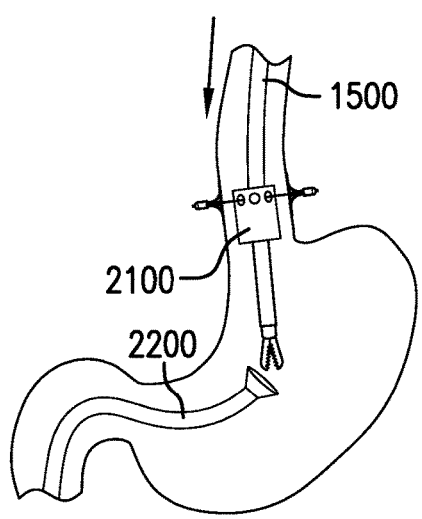

FIG. 19G shows grasping sleeve 2200. A grasping tool may be passed through cuff 2100 to grasp sleeve 2200. The grasping tool may be configured to pull drawstring 2241 to cinch ring 2240 of sleeve 2200.

Figure 19H:
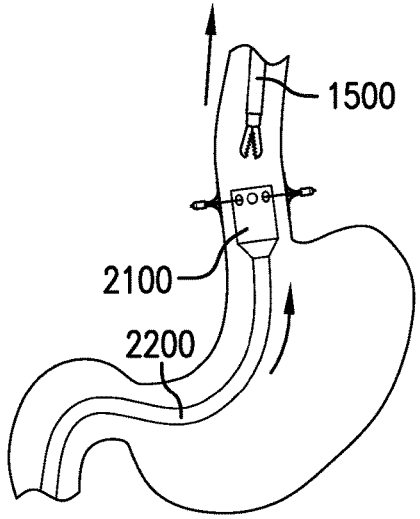

FIG. 19H shows attaching sleeve 2200 to cuff 2100. The grasping tool pulls ring 2240 of sleeve 2200 into cuff 2100 so that ring 2240 may be coupled to retainer 2140. Halo 2260 or attachment elements 3260 may be coupled to hooks 2160 or through attachment openings 3160, respectively.

While the foregoing has been with reference to particular embodiments of the invention, it will be appreciated by those skilled in the art that changes in these embodiments may be made without departing from the principles and spirit of the invention, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A method of treating a patient, the method comprising: anchoring a gastrointestinal bypass device in an esophagus of the patient by delivering one or more tissue anchors through the gastrointestinal bypass device and through a wall of the esophagus at an attachment point, wherein the attachment point is approximately 0 mm to approximately 50 mm above a diaphragm of the patient.

2. A method of treating a patient, the method comprising: anchoring a gastrointestinal bypass device in an esophagus of the patient by delivering one or more tissue anchors through the gastrointestinal bypass device and through a wall of the esophagus at an attachment point, wherein the attachment point is approximately 5 mm above to approximately 50 mm above a diaphragm of the patient.

3. A method of treating a patient, the method comprising: anchoring a gastrointestinal bypass device in an esophagus of the patient by delivering one or more tissue anchors through the gastrointestinal bypass device and through a wall of the esophagus at an attachment point, wherein the attachment point is approximately 20 mm above to approximately 50 mm above a diaphragm of the patient.

* * * * *